US010888433B2

(12) United States Patent
Frasier et al.

(10) Patent No.: US 10,888,433 B2
(45) Date of Patent: Jan. 12, 2021

(54) INTERVERTEBRAL IMPLANT INSERTER AND RELATED METHODS

(71) Applicant: DePuy Synthes Products, Inc., Raynham, MA (US)

(72) Inventors: William Frasier, New Bedford, MA (US); Sean Saidha, Franklin, MA (US); Thomas Martin, Riverside, RI (US); Paul S. Maguire, Hope Valley, RI (US)

(73) Assignee: DePuy Synthes Products, Inc., Raynham, MA (US)

( * ) Notice: Subject to any disclaimer, the term of this patent is extended or adjusted under 35 U.S.C. 154(b) by 10 days.

(21) Appl. No.: 15/478,305

(22) Filed: Apr. 4, 2017

(65) Prior Publication Data

US 2018/0161171 A1    Jun. 14, 2018

Related U.S. Application Data

(63) Continuation-in-part of application No. 15/378,724, filed on Dec. 14, 2016, now abandoned.

(51) Int. Cl.
| | | |
|---|---|---|
| *A61F 2/46* | (2006.01) |
| *A61F 2/44* | (2006.01) |
| *A61F 2/30* | (2006.01) |

(52) U.S. Cl.
CPC ............ *A61F 2/447* (2013.01); *A61F 2/4611* (2013.01); *A61F 2/4603* (2013.01); *A61F 2002/3039* (2013.01); *A61F 2002/30405* (2013.01); *A61F 2002/30411* (2013.01); *A61F 2002/30507* (2013.01); *A61F 2002/30515* (2013.01); *A61F 2002/30556* (2013.01); *A61F 2002/30904* (2013.01); *A61F 2002/4627* (2013.01)

(58) Field of Classification Search
CPC ............................... A61F 2/447; A61F 2/4611
See application file for complete search history.

(56) References Cited

U.S. PATENT DOCUMENTS

| | | |
|---|---|---|
| 1,802,560 A | 4/1931 | Kerwin |
| 1,924,695 A | 8/1933 | Olson |
| | (Continued) | |

FOREIGN PATENT DOCUMENTS

| | | |
|---|---|---|
| AU | 2005314079 A1 | 6/2006 |
| AU | 2006279558 A1 | 2/2007 |
| | (Continued) | |

OTHER PUBLICATIONS

Zucherman, "A Multicenter, Prospective, Randomized Trial Evaluating the X STOP Interspinous Process Decompression System for the Treatment of Neurogenic Intermittent Claudication", SPINE, vol. 30, No. 12, pp. 1351-1358, 2005.

(Continued)

*Primary Examiner* — Samuel S Hanna
(74) *Attorney, Agent, or Firm* — BakerHostetler

(57) ABSTRACT

An insertion instrument is configured to attach and secure to an expandable implant. The insertion instrument includes a securement member that is configured to be secured to the implant both when the implant is in a collapsed configuration and when the implant is in an expanded configuration. The insertion instrument further includes a drive member that is configured to actuate the implant to the expanded configuration.

23 Claims, 21 Drawing Sheets

(56) References Cited

U.S. PATENT DOCUMENTS

| | | | |
|---|---|---|---|
| 1,965,653 | A | 7/1934 | Kennedy |
| 2,077,804 | A | 4/1937 | Morrison |
| 2,115,250 | A | 4/1938 | Bruson |
| 2,121,193 | A | 6/1938 | Hanicke |
| 2,170,111 | A | 8/1939 | Bruson |
| 2,173,655 | A | 9/1939 | Neracher et al. |
| 2,229,024 | A | 1/1941 | Bruson |
| 2,243,717 | A | 5/1941 | Godoy Moreira |
| 2,381,050 | A | 8/1945 | Hardinge |
| 2,388,056 | A | 10/1945 | Hendricks |
| 2,485,531 | A | 10/1949 | William et al. |
| 2,489,870 | A | 11/1949 | Dzus |
| 2,570,465 | A | 10/1951 | Lundholm |
| 2,677,369 | A | 5/1954 | Knowles |
| 2,706,701 | A | 4/1955 | Hans et al. |
| 2,710,277 | A | 6/1955 | Shelanski et al. |
| 2,826,532 | A | 3/1958 | Hosmer |
| 2,900,305 | A | 8/1959 | Siggia |
| 2,977,315 | A | 3/1961 | Scheib et al. |
| 3,091,237 | A | 5/1963 | Skinner |
| 3,112,743 | A | 12/1963 | Cochran et al. |
| 3,115,804 | A | 12/1963 | Johnson |
| 3,228,828 | A | 1/1966 | Romano |
| 3,312,139 | A | 4/1967 | Di Cristina |
| 3,486,505 | A | 12/1969 | Morrison |
| 3,489,143 | A | 1/1970 | Halloran |
| 3,648,294 | A | 3/1972 | Shahrestani |
| 3,698,391 | A | 10/1972 | Mahony |
| 3,717,655 | A | 2/1973 | Godefroi et al. |
| 3,760,802 | A | 9/1973 | Fischer et al. |
| 3,800,788 | A | 4/1974 | White |
| 3,805,775 | A | 4/1974 | Fischer et al. |
| 3,811,449 | A | 5/1974 | Gravlee et al. |
| 3,842,825 | A | 10/1974 | Wagner |
| 3,848,601 | A | 11/1974 | Ma et al. |
| 3,855,638 | A | 12/1974 | Pilliar |
| 3,867,728 | A | 2/1975 | Stubstad et al. |
| 3,875,595 | A | 4/1975 | Froning |
| 3,889,665 | A | 6/1975 | Ling et al. |
| 3,964,480 | A | 6/1976 | Froning |
| 3,986,504 | A | 10/1976 | Avila |
| 4,013,071 | A | 3/1977 | Rosenberg |
| 4,052,988 | A | 10/1977 | Doddi et al. |
| 4,091,806 | A | 5/1978 | Aginsky |
| 4,175,555 | A | 11/1979 | Herbert |
| 4,236,512 | A | 12/1980 | Aginsky |
| 4,249,435 | A * | 2/1981 | Villeneuve .......... B25B 23/1427 81/477 |
| 4,262,665 | A | 4/1981 | Roalstad et al. |
| 4,262,676 | A | 4/1981 | Jamshidi |
| 4,274,163 | A | 6/1981 | Malcom et al. |
| 4,275,717 | A | 6/1981 | Bolesky |
| 4,312,337 | A | 1/1982 | Donohue |
| 4,312,353 | A | 1/1982 | Shahbabian |
| 4,313,434 | A | 2/1982 | Segal |
| 4,341,206 | A | 7/1982 | Perrett et al. |
| 4,349,921 | A | 9/1982 | Kuntz |
| 4,350,151 | A | 9/1982 | Scott |
| 4,351,069 | A | 9/1982 | Ballintyn et al. |
| 4,352,883 | A | 10/1982 | Lim |
| 4,369,790 | A | 1/1983 | McCarthy |
| 4,399,814 | A | 8/1983 | Pratt et al. |
| 4,401,112 | A | 8/1983 | Rezaian |
| 4,401,433 | A | 8/1983 | Luther |
| 4,409,974 | A | 10/1983 | Freedland |
| 4,440,921 | A | 4/1984 | Allcock et al. |
| 4,449,532 | A | 5/1984 | Storz |
| 4,451,256 | A | 5/1984 | Weikl et al. |
| 4,456,005 | A | 6/1984 | Lichty |
| 4,462,394 | A | 7/1984 | Jacobs |
| 4,463,753 | A | 8/1984 | Gustilo |
| 4,466,435 | A | 8/1984 | Murray |
| 4,467,479 | A | 8/1984 | Brody |
| 4,488,543 | A | 12/1984 | Tornier |
| 4,488,549 | A | 12/1984 | Lee et al. |
| 4,494,535 | A | 1/1985 | Haig |
| 4,495,174 | A | 1/1985 | Allcock et al. |
| 4,532,660 | A | 8/1985 | Field |
| 4,537,185 | A | 8/1985 | Stednitz |
| 4,542,539 | A | 9/1985 | Rowe et al. |
| 4,545,374 | A | 10/1985 | Jacobson |
| 4,562,598 | A | 1/1986 | Kranz |
| 4,573,448 | A | 3/1986 | Kambin |
| 4,595,006 | A | 6/1986 | Burke et al. |
| 4,601,710 | A | 7/1986 | Moll |
| 4,625,722 | A | 12/1986 | Murray |
| 4,625,725 | A | 12/1986 | Davison et al. |
| 4,627,434 | A | 12/1986 | Murray |
| 4,628,945 | A | 12/1986 | Johnson, Jr. |
| 4,629,450 | A | 12/1986 | Suzuki et al. |
| 4,630,616 | A | 12/1986 | Tretinyak |
| 4,632,101 | A | 12/1986 | Freedland |
| 4,640,271 | A | 2/1987 | Lower |
| 4,641,640 | A | 2/1987 | Griggs |
| 4,645,503 | A | 2/1987 | Lin et al. |
| 4,651,717 | A | 3/1987 | Jakubczak |
| 4,653,489 | A | 3/1987 | Tronzo |
| 4,665,906 | A | 5/1987 | Jervis |
| 4,667,663 | A | 5/1987 | Miyata |
| 4,686,973 | A | 8/1987 | Frisch |
| 4,686,984 | A | 8/1987 | Bonnet |
| 4,688,561 | A | 8/1987 | Reese |
| 4,697,584 | A | 10/1987 | Haynes |
| 4,706,670 | A | 11/1987 | Andersen et al. |
| 4,714,469 | A | 12/1987 | Kenna |
| 4,714,478 | A | 12/1987 | Fischer |
| 4,721,103 | A | 1/1988 | Freedland |
| 4,723,544 | A | 2/1988 | Moore et al. |
| 4,743,256 | A | 5/1988 | Brantigan |
| 4,743,257 | A | 5/1988 | Toermaelae et al. |
| 4,759,766 | A | 7/1988 | Buettner-Janz et al. |
| 4,760,843 | A | 8/1988 | Fischer et al. |
| 4,772,287 | A | 9/1988 | Ray et al. |
| 4,790,304 | A | 12/1988 | Rosenberg |
| 4,790,817 | A | 12/1988 | Luther |
| 4,796,612 | A | 1/1989 | Reese |
| 4,802,479 | A | 2/1989 | Haber et al. |
| 4,815,909 | A | 3/1989 | Simons |
| 4,827,917 | A | 5/1989 | Brumfield |
| 4,834,069 | A | 5/1989 | Umeda |
| 4,838,282 | A | 6/1989 | Strasser et al. |
| 4,858,601 | A | 8/1989 | Glisson |
| 4,862,891 | A | 9/1989 | Smith |
| 4,863,476 | A | 9/1989 | Shepperd |
| 4,870,153 | A | 9/1989 | Matzner et al. |
| 4,871,366 | A | 10/1989 | Von et al. |
| 4,873,976 | A | 10/1989 | Schreiber |
| 4,878,915 | A | 11/1989 | Brantigan |
| 4,880,622 | A | 11/1989 | Allcock et al. |
| 4,888,022 | A | 12/1989 | Huebsch |
| 4,888,024 | A | 12/1989 | Powlan |
| 4,892,550 | A | 1/1990 | Huebsch |
| 4,896,662 | A | 1/1990 | Noble |
| 4,898,186 | A | 2/1990 | Ikada et al. |
| 4,898,577 | A | 2/1990 | Badger et al. |
| 4,903,692 | A | 2/1990 | Reese |
| 4,904,261 | A | 2/1990 | Dove et al. |
| 4,911,718 | A | 3/1990 | Lee et al. |
| 4,917,554 | A | 4/1990 | Bronn |
| 4,932,969 | A | 6/1990 | Frey et al. |
| 4,940,467 | A | 7/1990 | Tronzo |
| 4,941,466 | A | 7/1990 | Romano |
| 4,946,378 | A | 8/1990 | Hirayama et al. |
| 4,959,064 | A | 9/1990 | Engelhardt |
| 4,961,740 | A | 10/1990 | Ray et al. |
| 4,963,144 | A | 10/1990 | Huene |
| 4,966,587 | A | 10/1990 | Baumgart |
| 4,968,317 | A | 11/1990 | Toermaelae et al. |
| 4,969,888 | A | 11/1990 | Scholten et al. |
| 4,978,334 | A | 12/1990 | Toye et al. |
| 4,978,349 | A | 12/1990 | Frigg |
| 4,981,482 | A | 1/1991 | Ichikawa |
| 4,988,351 | A | 1/1991 | Paulos et al. |
| 4,994,027 | A | 2/1991 | Farrell |

(56) References Cited

U.S. PATENT DOCUMENTS

| | | |
|---|---|---|
| 5,002,557 A | 3/1991 | Hasson |
| 5,011,484 A | 4/1991 | Breard |
| 5,013,315 A | 5/1991 | Barrows |
| 5,013,316 A | 5/1991 | Goble et al. |
| 5,015,247 A | 5/1991 | Michelson |
| 5,015,255 A | 5/1991 | Kuslich |
| 5,030,233 A | 7/1991 | Ducheyne |
| 5,051,189 A | 9/1991 | Farrah |
| 5,053,035 A | 10/1991 | McLaren |
| 5,055,104 A | 10/1991 | Ray |
| 5,059,193 A | 10/1991 | Kuslich |
| 5,062,849 A | 11/1991 | Schelhas |
| 5,071,435 A | 12/1991 | Fuchs et al. |
| 5,071,437 A | 12/1991 | Steffee |
| 5,080,662 A | 1/1992 | Paul |
| 5,084,043 A | 1/1992 | Hertzmann et al. |
| 5,092,891 A | 3/1992 | Kummer et al. |
| 5,098,241 A | 3/1992 | Aldridge et al. |
| 5,098,433 A | 3/1992 | Freedland |
| 5,098,435 A | 3/1992 | Stednitz et al. |
| 5,102,413 A | 4/1992 | Poddar |
| 5,108,404 A | 4/1992 | Scholten et al. |
| 5,114,407 A | 5/1992 | Burbank |
| 5,116,336 A | 5/1992 | Frigg |
| 5,120,171 A | 6/1992 | Lasner |
| 5,122,130 A | 6/1992 | Keller |
| 5,122,133 A | 6/1992 | Evans |
| 5,122,141 A | 6/1992 | Simpson et al. |
| 5,123,926 A | 6/1992 | Pisharodi |
| 5,133,755 A | 7/1992 | Brekke |
| 5,134,477 A | 7/1992 | Knauer et al. |
| 5,139,486 A | 8/1992 | Moss |
| 5,147,366 A | 9/1992 | Arroyo et al. |
| 5,158,543 A | 10/1992 | Lazarus |
| 5,163,989 A | 11/1992 | Campbell et al. |
| 5,167,663 A | 12/1992 | Brumfield |
| 5,167,664 A | 12/1992 | Hodorek |
| 5,167,665 A | 12/1992 | McKinney |
| 5,169,400 A | 12/1992 | Muehling et al. |
| 5,171,278 A | 12/1992 | Pisharodi |
| 5,171,279 A | 12/1992 | Mathews |
| 5,171,280 A | 12/1992 | Baumgartner |
| 5,176,651 A | 1/1993 | Allgood et al. |
| 5,176,683 A | 1/1993 | Kimsey et al. |
| 5,176,692 A | 1/1993 | Wilk et al. |
| 5,176,697 A | 1/1993 | Hasson et al. |
| 5,178,501 A | 1/1993 | Carstairs |
| 5,183,052 A | 2/1993 | Terwilliger |
| 5,183,464 A | 2/1993 | Dubrul et al. |
| 5,188,118 A | 2/1993 | Terwilliger |
| 5,192,327 A | 3/1993 | Brantigan |
| 5,195,506 A | 3/1993 | Hulfish |
| 5,201,742 A | 4/1993 | Hasson |
| 5,217,462 A | 6/1993 | Asnis et al. |
| 5,217,486 A | 6/1993 | Rice et al. |
| 5,224,952 A | 7/1993 | Deniega et al. |
| 5,228,441 A | 7/1993 | Lundquist |
| 5,234,431 A | 8/1993 | Keller |
| 5,241,972 A | 9/1993 | Bonati |
| 5,242,410 A | 9/1993 | Melker |
| 5,242,447 A | 9/1993 | Borzone |
| 5,242,448 A | 9/1993 | Pettine et al. |
| 5,242,879 A | 9/1993 | Abe et al. |
| 5,246,441 A | 9/1993 | Ross et al. |
| 5,250,049 A | 10/1993 | Michael |
| 5,257,632 A | 11/1993 | Turkel et al. |
| 5,263,953 A | 11/1993 | Bagby |
| 5,269,797 A | 12/1993 | Bonati et al. |
| 5,280,782 A | 1/1994 | Wilk |
| 5,285,795 A | 2/1994 | Ryan et al. |
| 5,286,001 A | 2/1994 | Rafeld |
| 5,290,243 A | 3/1994 | Chodorow et al. |
| 5,290,312 A | 3/1994 | Kojimoto et al. |
| 5,300,074 A | 4/1994 | Frigg |
| 5,303,718 A | 4/1994 | Krajicek |
| 5,304,142 A | 4/1994 | Liebl et al. |
| 5,306,307 A | 4/1994 | Senter et al. |
| 5,306,308 A | 4/1994 | Gross et al. |
| 5,306,309 A | 4/1994 | Wagner et al. |
| 5,306,310 A | 4/1994 | Siebels |
| 5,308,327 A | 5/1994 | Heaven et al. |
| 5,308,352 A | 5/1994 | Koutrouvelis |
| 5,312,410 A | 5/1994 | Miller et al. |
| 5,312,417 A | 5/1994 | Wilk |
| 5,314,477 A | 5/1994 | Marnay |
| 5,322,505 A | 6/1994 | Krause et al. |
| 5,324,261 A | 6/1994 | Amundson et al. |
| 5,330,429 A | 7/1994 | Noguchi et al. |
| 5,331,975 A | 7/1994 | Bonutti |
| 5,334,184 A | 8/1994 | Bimman |
| 5,334,204 A | 8/1994 | Clewett et al. |
| 5,342,365 A | 8/1994 | Waldman |
| 5,342,382 A | 8/1994 | Brinkerhoff et al. |
| 5,344,252 A | 9/1994 | Kakimoto |
| 5,354,298 A | 10/1994 | Lee et al. |
| 5,361,752 A | 11/1994 | Moll et al. |
| 5,364,398 A | 11/1994 | Chapman et al. |
| 5,370,646 A | 12/1994 | Reese et al. |
| 5,370,647 A | 12/1994 | Graber et al. |
| 5,370,661 A | 12/1994 | Branch |
| 5,370,697 A | 12/1994 | Baumgartner |
| 5,372,660 A | 12/1994 | Davidson et al. |
| 5,374,267 A | 12/1994 | Siegal |
| 5,382,248 A | 1/1995 | Jacobson et al. |
| 5,383,932 A | 1/1995 | Wilson et al. |
| 5,385,151 A | 1/1995 | Scarfone et al. |
| 5,387,213 A | 2/1995 | Breard et al. |
| 5,387,215 A | 2/1995 | Fisher |
| 5,390,683 A | 2/1995 | Pisharodi |
| 5,395,317 A | 3/1995 | Kambin |
| 5,395,371 A | 3/1995 | Miller et al. |
| 5,397,364 A | 3/1995 | Kozak et al. |
| 5,401,269 A | 3/1995 | Buettner-Janz et al. |
| 5,407,430 A | 4/1995 | Peters |
| 5,410,016 A | 4/1995 | Hubbell et al. |
| 5,415,661 A | 5/1995 | Holmes |
| 5,423,816 A | 6/1995 | Lin |
| 5,423,817 A | 6/1995 | Lin |
| 5,423,850 A | 6/1995 | Berger |
| 5,424,773 A | 6/1995 | Saito |
| 5,425,773 A | 6/1995 | Boyd et al. |
| 5,431,658 A | 7/1995 | Moskovich |
| 5,441,538 A | 8/1995 | Bonutti |
| 5,443,514 A | 8/1995 | Steffee |
| 5,449,359 A | 9/1995 | Groiso |
| 5,449,361 A | 9/1995 | Preissman |
| 5,452,748 A | 9/1995 | Simmons et al. |
| 5,454,365 A | 10/1995 | Bonutti |
| 5,454,790 A | 10/1995 | Dubrul |
| 5,454,827 A | 10/1995 | Aust et al. |
| 5,456,686 A | 10/1995 | Klapper et al. |
| 5,458,641 A | 10/1995 | Ramirez Jimenez |
| 5,458,643 A | 10/1995 | Oka et al. |
| 5,462,563 A | 10/1995 | Shearer et al. |
| 5,464,427 A | 11/1995 | Curtis et al. |
| 5,468,245 A | 11/1995 | Vargas, III |
| 5,470,333 A | 11/1995 | Ray |
| 5,472,426 A | 12/1995 | Bonati et al. |
| 5,474,539 A | 12/1995 | Costa et al. |
| 5,480,400 A | 1/1996 | Berger |
| 5,484,437 A | 1/1996 | Michelson |
| 5,486,190 A | 1/1996 | Green |
| 5,496,318 A | 3/1996 | Howland et al. |
| 5,498,265 A | 3/1996 | Asnis et al. |
| 5,501,695 A | 3/1996 | Anspach et al. |
| 5,505,710 A | 4/1996 | Dorsey, III |
| 5,507,816 A | 4/1996 | Bullivant |
| 5,509,923 A | 4/1996 | Middleman et al. |
| 5,512,037 A | 4/1996 | Russell et al. |
| 5,514,143 A | 5/1996 | Bonutti et al. |
| 5,514,153 A | 5/1996 | Bonutti |
| 5,514,180 A | 5/1996 | Heggeness et al. |
| 5,520,690 A | 5/1996 | Errico et al. |
| 5,520,896 A | 5/1996 | De et al. |

(56) References Cited

U.S. PATENT DOCUMENTS

| | | |
|---|---|---|
| 5,522,398 A | 6/1996 | Goldenberg et al. |
| 5,522,790 A | 6/1996 | Moll et al. |
| 5,522,846 A | 6/1996 | Bonutti |
| 5,522,895 A | 6/1996 | Mikos |
| 5,522,899 A | 6/1996 | Michelson |
| 5,527,312 A | 6/1996 | Ray |
| 5,527,343 A | 6/1996 | Bonutti |
| 5,527,624 A | 6/1996 | Higgins et al. |
| 5,531,856 A | 7/1996 | Moll et al. |
| 5,534,023 A | 7/1996 | Henley |
| 5,534,029 A | 7/1996 | Shima |
| 5,534,030 A | 7/1996 | Navarro et al. |
| 5,536,127 A | 7/1996 | Pennig |
| 5,538,009 A | 7/1996 | Byrne et al. |
| 5,540,688 A | 7/1996 | Navas |
| 5,540,693 A | 7/1996 | Fisher |
| 5,540,711 A | 7/1996 | Kieturakis et al. |
| 5,545,164 A | 8/1996 | Howland |
| 5,545,222 A | 8/1996 | Bonutti |
| 5,549,610 A | 8/1996 | Russell et al. |
| 5,549,679 A | 8/1996 | Kuslich |
| 5,554,191 A | 9/1996 | Lahille et al. |
| 5,556,431 A | 9/1996 | Buettner-Janz |
| 5,558,674 A | 9/1996 | Heggeness et al. |
| D374,287 S | 10/1996 | Goble et al. |
| 5,562,736 A | 10/1996 | Ray et al. |
| 5,562,738 A | 10/1996 | Boyd et al. |
| 5,564,926 A | 10/1996 | Braanemark |
| 5,569,248 A | 10/1996 | Mathews |
| 5,569,251 A | 10/1996 | Baker et al. |
| 5,569,290 A | 10/1996 | McAfee |
| 5,569,548 A | 10/1996 | Koike et al. |
| 5,571,109 A | 11/1996 | Bertagnoli |
| 5,571,189 A | 11/1996 | Kuslich |
| 5,571,190 A | 11/1996 | Ulrich et al. |
| 5,575,790 A | 11/1996 | Chen et al. |
| 5,591,168 A | 1/1997 | Judet et al. |
| 5,593,409 A | 1/1997 | Michelson |
| 5,601,556 A | 2/1997 | Pisharodi |
| 5,601,572 A | 2/1997 | Middleman et al. |
| 5,609,634 A | 3/1997 | Voydeville |
| 5,609,635 A | 3/1997 | Michelson |
| 5,613,950 A | 3/1997 | Yoon |
| 5,618,142 A | 4/1997 | Sonden et al. |
| 5,618,314 A | 4/1997 | Harwin et al. |
| 5,624,447 A | 4/1997 | Myers |
| 5,626,613 A | 5/1997 | Schmieding |
| 5,628,751 A | 5/1997 | Sander et al. |
| 5,628,752 A | 5/1997 | Asnis et al. |
| 5,632,746 A | 5/1997 | Middleman et al. |
| 5,639,276 A | 6/1997 | Weinstock et al. |
| 5,643,320 A | 7/1997 | Lower et al. |
| 5,645,589 A | 7/1997 | Li |
| 5,645,596 A | 7/1997 | Kim et al. |
| 5,645,597 A | 7/1997 | Krapiva |
| 5,645,599 A | 7/1997 | Samani |
| 5,647,857 A | 7/1997 | Anderson et al. |
| 5,649,931 A | 7/1997 | Bryant et al. |
| 5,653,763 A | 8/1997 | Errico et al. |
| 5,658,335 A | 8/1997 | Allen |
| 5,662,683 A | 9/1997 | Kay |
| 5,665,095 A | 9/1997 | Jacobson et al. |
| 5,665,122 A | 9/1997 | Kambin |
| 5,667,508 A | 9/1997 | Errico et al. |
| 5,669,915 A | 9/1997 | Caspar et al. |
| 5,669,926 A | 9/1997 | Aust et al. |
| 5,674,294 A | 10/1997 | Bainville et al. |
| 5,674,295 A | 10/1997 | Ray et al. |
| 5,674,296 A | 10/1997 | Bryan et al. |
| 5,676,701 A | 10/1997 | Yuan et al. |
| 5,679,723 A | 10/1997 | Cooper et al. |
| 5,681,263 A | 10/1997 | Flesch |
| 5,683,465 A | 11/1997 | Shinn et al. |
| 5,693,100 A | 12/1997 | Pisharodi |
| 5,695,513 A | 12/1997 | Johnson et al. |
| 5,697,977 A | 12/1997 | Pisharodi |
| 5,700,239 A | 12/1997 | Yoon |
| 5,702,391 A | 12/1997 | Lin |
| 5,702,449 A | 12/1997 | McKay |
| 5,702,450 A | 12/1997 | Bisserie |
| 5,702,453 A | 12/1997 | Rabbe et al. |
| 5,702,454 A | 12/1997 | Baumgartner |
| 5,707,359 A | 1/1998 | Bufalini |
| 5,713,870 A | 2/1998 | Yoon |
| 5,713,903 A | 2/1998 | Sander et al. |
| 5,716,415 A | 2/1998 | Steffee |
| 5,716,416 A | 2/1998 | Lin |
| 5,720,753 A | 2/1998 | Sander et al. |
| 5,725,541 A | 3/1998 | Anspach et al. |
| 5,725,588 A | 3/1998 | Errico et al. |
| 5,728,097 A | 3/1998 | Mathews |
| 5,728,116 A | 3/1998 | Rosenman |
| 5,735,853 A | 4/1998 | Olerud |
| 5,741,253 A | 4/1998 | Michelson |
| 5,741,282 A | 4/1998 | Anspach et al. |
| 5,743,881 A | 4/1998 | Demco |
| 5,743,912 A | 4/1998 | Lahille et al. |
| 5,743,914 A | 4/1998 | Skiba |
| 5,749,879 A | 5/1998 | Middleman et al. |
| 5,749,889 A | 5/1998 | Bacich et al. |
| 5,752,969 A | 5/1998 | Cunci et al. |
| 5,755,797 A | 5/1998 | Baumgartner |
| 5,755,798 A | 5/1998 | Papavero et al. |
| 5,756,127 A | 5/1998 | Grisoni et al. |
| 5,762,500 A | 6/1998 | Lazarof |
| 5,762,629 A | 6/1998 | Kambin |
| 5,766,252 A | 6/1998 | Henry et al. |
| 5,772,661 A | 6/1998 | Michelson |
| 5,772,662 A | 6/1998 | Chapman et al. |
| 5,772,678 A | 6/1998 | Thomason et al. |
| 5,776,156 A | 7/1998 | Shikhman |
| 5,782,800 A | 7/1998 | Yoon |
| 5,782,832 A | 7/1998 | Larsen et al. |
| 5,782,865 A | 7/1998 | Grotz |
| 5,788,703 A | 8/1998 | Mittelmeier et al. |
| 5,792,044 A | 8/1998 | Foley et al. |
| 5,797,909 A | 8/1998 | Michelson |
| 5,800,549 A | 9/1998 | Bao et al. |
| 5,807,275 A | 9/1998 | Jamshidi |
| 5,807,327 A | 9/1998 | Green et al. |
| 5,810,721 A | 9/1998 | Mueller et al. |
| 5,810,821 A | 9/1998 | Vandewalle |
| 5,810,866 A | 9/1998 | Yoon |
| 5,814,084 A | 9/1998 | Grivas et al. |
| 5,820,628 A | 10/1998 | Middleman et al. |
| 5,823,979 A | 10/1998 | Mezo |
| 5,824,084 A | 10/1998 | Muschler |
| 5,824,093 A | 10/1998 | Ray et al. |
| 5,824,094 A | 10/1998 | Serhan et al. |
| 5,827,289 A | 10/1998 | Reiley et al. |
| 5,833,657 A | 11/1998 | Reinhardt et al. |
| 5,836,948 A | 11/1998 | Zucherman et al. |
| 5,837,752 A | 11/1998 | Shastri et al. |
| 5,846,259 A | 12/1998 | Berthiaume |
| 5,848,986 A | 12/1998 | Lundquist et al. |
| 5,849,004 A | 12/1998 | Bramlet |
| 5,851,212 A | 12/1998 | Zirps et al. |
| 5,851,216 A | 12/1998 | Allen |
| 5,860,973 A | 1/1999 | Michelson |
| 5,860,977 A | 1/1999 | Zucherman et al. |
| 5,865,846 A | 2/1999 | Bryan et al. |
| 5,865,848 A | 2/1999 | Baker |
| 5,871,485 A | 2/1999 | Rao et al. |
| 5,873,854 A | 2/1999 | Wolvek |
| 5,876,404 A | 3/1999 | Zucherman et al. |
| 5,888,220 A | 3/1999 | Felt et al. |
| 5,888,223 A | 3/1999 | Bray, Jr. |
| 5,888,224 A | 3/1999 | Beckers et al. |
| 5,888,226 A | 3/1999 | Rogozinski |
| 5,888,227 A | 3/1999 | Cottle |
| 5,888,228 A | 3/1999 | Knothe et al. |
| 5,893,850 A | 4/1999 | Cachia |
| 5,893,889 A | 4/1999 | Harrington |
| 5,893,890 A | 4/1999 | Pisharodi |

(56) References Cited

U.S. PATENT DOCUMENTS

| | | |
|---|---|---|
| 5,895,428 A | 4/1999 | Berry |
| 5,902,231 A | 5/1999 | Foley et al. |
| 5,904,690 A | 5/1999 | Middleman et al. |
| 5,904,696 A | 5/1999 | Rosenman |
| 5,908,422 A | 6/1999 | Bresina |
| 5,919,235 A | 7/1999 | Husson et al. |
| 5,925,074 A | 7/1999 | Gingras et al. |
| 5,928,235 A | 7/1999 | Friedl |
| 5,928,244 A | 7/1999 | Tovey et al. |
| 5,928,422 A | 7/1999 | Uchiyama et al. |
| 5,931,870 A | 8/1999 | Cuckler et al. |
| 5,935,129 A | 8/1999 | McDevitt et al. |
| 5,947,999 A | 9/1999 | Groiso |
| 5,948,000 A | 9/1999 | Larsen et al. |
| 5,954,722 A | 9/1999 | Bono |
| 5,954,747 A | 9/1999 | Clark |
| 5,957,902 A | 9/1999 | Teves |
| 5,957,924 A | 9/1999 | Toermaelae et al. |
| 5,961,554 A | 10/1999 | Janson et al. |
| 5,964,730 A | 10/1999 | Williams et al. |
| 5,964,761 A | 10/1999 | Kambin |
| 5,967,783 A | 10/1999 | Ura |
| 5,967,970 A | 10/1999 | Cowan et al. |
| 5,968,044 A | 10/1999 | Nicholson et al. |
| 5,968,098 A | 10/1999 | Winslow |
| 5,972,015 A | 10/1999 | Scribner et al. |
| 5,972,385 A | 10/1999 | Liu et al. |
| 5,976,139 A | 11/1999 | Bramlet |
| 5,976,146 A | 11/1999 | Ogawa et al. |
| 5,976,186 A | 11/1999 | Bao et al. |
| 5,980,522 A | 11/1999 | Koros et al. |
| 5,984,927 A | 11/1999 | Wenstrom et al. |
| 5,984,966 A | 11/1999 | Kiema et al. |
| 5,985,307 A | 11/1999 | Hanson et al. |
| 5,989,255 A | 11/1999 | Pepper et al. |
| 5,989,291 A | 11/1999 | Ralph et al. |
| 5,993,459 A | 11/1999 | Larsen et al. |
| 5,997,510 A | 12/1999 | Schwemberger |
| 5,997,538 A | 12/1999 | Asnis et al. |
| 5,997,541 A | 12/1999 | Schenk |
| 6,001,100 A | 12/1999 | Sherman et al. |
| 6,001,101 A | 12/1999 | Augagneur et al. |
| 6,004,327 A | 12/1999 | Asnis et al. |
| 6,005,161 A | 12/1999 | Brekke |
| 6,007,519 A | 12/1999 | Rosselli |
| 6,007,566 A | 12/1999 | Wenstrom, Jr. |
| 6,007,580 A | 12/1999 | Lehto et al. |
| 6,010,508 A * | 1/2000 | Bradley ............... A61B 17/151 606/86 R |
| 6,010,513 A | 1/2000 | Toermaelae et al. |
| 6,012,494 A | 1/2000 | Balazs |
| 6,015,410 A | 1/2000 | Toermaelae et al. |
| 6,015,436 A | 1/2000 | Schoenhoeffer |
| 6,019,762 A | 2/2000 | Cole |
| 6,019,792 A | 2/2000 | Cauthen |
| 6,019,793 A | 2/2000 | Perren et al. |
| 6,022,350 A | 2/2000 | Ganem |
| 6,022,352 A | 2/2000 | Vandewalle |
| 6,030,162 A | 2/2000 | Huebner |
| 6,030,364 A | 2/2000 | Durgin et al. |
| 6,030,401 A | 2/2000 | Marino |
| 6,033,406 A | 3/2000 | Mathews |
| 6,033,412 A | 3/2000 | Losken et al. |
| 6,036,701 A | 3/2000 | Rosenman |
| 6,039,740 A | 3/2000 | Olerud |
| 6,039,761 A | 3/2000 | Li et al. |
| 6,039,763 A | 3/2000 | Shelokov |
| 6,045,552 A | 4/2000 | Zucherman et al. |
| 6,045,579 A | 4/2000 | Hochschuler et al. |
| 6,048,309 A | 4/2000 | Flom et al. |
| 6,048,342 A | 4/2000 | Zucherman et al. |
| 6,048,346 A | 4/2000 | Reiley et al. |
| 6,048,360 A | 4/2000 | Khosravi et al. |
| 6,053,935 A | 4/2000 | Brenneman et al. |
| 6,063,121 A | 5/2000 | Xavier et al. |
| 6,066,142 A | 5/2000 | Serbousek et al. |
| 6,066,154 A | 5/2000 | Reiley et al. |
| 6,068,630 A | 5/2000 | Zucherman et al. |
| 6,068,648 A | 5/2000 | Cole et al. |
| 6,071,982 A | 6/2000 | Wise et al. |
| 6,073,051 A | 6/2000 | Sharkey et al. |
| 6,074,390 A | 6/2000 | Zucherman et al. |
| 6,080,155 A | 6/2000 | Michelson |
| 6,080,193 A | 6/2000 | Hochschuler et al. |
| 6,083,225 A | 7/2000 | Winslow et al. |
| 6,083,244 A | 7/2000 | Lubbers et al. |
| 6,090,112 A | 7/2000 | Zucherman et al. |
| 6,090,143 A | 7/2000 | Meriwether et al. |
| 6,096,038 A | 8/2000 | Michelson |
| 6,096,080 A | 8/2000 | Nicholson et al. |
| 6,099,531 A | 8/2000 | Bonutti |
| 6,102,914 A | 8/2000 | Bulstra et al. |
| 6,102,950 A | 8/2000 | Vaccaro |
| 6,106,557 A | 8/2000 | Robioneck et al. |
| 6,110,210 A | 8/2000 | Norton et al. |
| 6,113,624 A | 9/2000 | Bezwada et al. |
| 6,113,636 A | 9/2000 | Ogle |
| 6,113,637 A | 9/2000 | Gill et al. |
| 6,113,638 A | 9/2000 | Williams et al. |
| 6,113,640 A | 9/2000 | Toermaelae et al. |
| 6,117,174 A | 9/2000 | Nolan |
| 6,119,044 A | 9/2000 | Kuzma |
| 6,123,705 A | 9/2000 | Michelson |
| 6,123,711 A | 9/2000 | Winters |
| 6,126,660 A | 10/2000 | Dietz |
| 6,126,661 A | 10/2000 | Faccioli et al. |
| 6,126,663 A | 10/2000 | Hair |
| 6,126,686 A | 10/2000 | Badylak et al. |
| 6,126,689 A | 10/2000 | Brett |
| 6,127,597 A | 10/2000 | Beyar et al. |
| 6,129,762 A | 10/2000 | Li |
| 6,129,763 A | 10/2000 | Chauvin et al. |
| 6,132,435 A * | 10/2000 | Young ............... A61B 17/8875 192/56.54 |
| 6,136,031 A | 10/2000 | Middleton |
| 6,139,579 A | 10/2000 | Steffee et al. |
| 6,146,384 A | 11/2000 | Lee et al. |
| 6,146,387 A | 11/2000 | Trott et al. |
| 6,146,420 A | 11/2000 | McKay |
| 6,146,421 A | 11/2000 | Gordon et al. |
| 6,147,135 A | 11/2000 | Yuan et al. |
| 6,149,652 A | 11/2000 | Zucherman et al. |
| 6,152,926 A | 11/2000 | Zucherman et al. |
| 6,156,038 A | 12/2000 | Zucherman et al. |
| 6,159,179 A | 12/2000 | Simonson |
| 6,159,211 A | 12/2000 | Boriani et al. |
| 6,159,244 A | 12/2000 | Suddaby |
| 6,161,350 A | 12/2000 | Espinosa |
| 6,162,234 A | 12/2000 | Freedland et al. |
| 6,162,236 A | 12/2000 | Osada |
| 6,162,252 A | 12/2000 | Kuras et al. |
| 6,165,218 A | 12/2000 | Husson et al. |
| 6,165,486 A | 12/2000 | Marra et al. |
| 6,168,595 B1 | 1/2001 | Durham et al. |
| 6,168,597 B1 | 1/2001 | Biedermann et al. |
| 6,171,610 B1 | 1/2001 | Vacanti et al. |
| 6,174,337 B1 | 1/2001 | Keenan |
| 6,175,758 B1 | 1/2001 | Kambin |
| 6,176,882 B1 | 1/2001 | Biedermann et al. |
| 6,179,794 B1 | 1/2001 | Burras |
| 6,179,873 B1 | 1/2001 | Zientek |
| 6,183,471 B1 | 2/2001 | Zucherman et al. |
| 6,183,472 B1 | 2/2001 | Lutz |
| 6,183,474 B1 | 2/2001 | Bramlet et al. |
| 6,183,517 B1 | 2/2001 | Suddaby |
| 6,187,043 B1 | 2/2001 | Ledergerber |
| 6,187,048 B1 | 2/2001 | Milner et al. |
| 6,190,387 B1 | 2/2001 | Zucherman et al. |
| 6,190,414 B1 | 2/2001 | Young et al. |
| 6,193,757 B1 | 2/2001 | Foley et al. |
| 6,197,033 B1 | 3/2001 | Haid et al. |
| 6,197,041 B1 | 3/2001 | Shichman et al. |
| 6,197,065 B1 | 3/2001 | Martin et al. |
| 6,197,325 B1 | 3/2001 | MacPhee et al. |

(56) References Cited

U.S. PATENT DOCUMENTS

| | | |
|---|---|---|
| 6,200,322 B1 | 3/2001 | Branch et al. |
| 6,203,565 B1 | 3/2001 | Bonutti et al. |
| 6,206,826 B1 | 3/2001 | Mathews et al. |
| 6,206,922 B1 | 3/2001 | Zdeblick et al. |
| D439,980 S | 4/2001 | Reiley et al. |
| 6,213,957 B1 | 4/2001 | Milliman et al. |
| 6,214,368 B1 | 4/2001 | Lee et al. |
| 6,217,509 B1 | 4/2001 | Foley et al. |
| 6,217,579 B1 | 4/2001 | Koros |
| 6,221,082 B1 | 4/2001 | Marino et al. |
| 6,224,603 B1 | 5/2001 | Marino |
| 6,224,631 B1 | 5/2001 | Kohrs |
| 6,224,894 B1 | 5/2001 | Jamiolkowski et al. |
| 6,228,058 B1 | 5/2001 | Dennis et al. |
| 6,231,606 B1 | 5/2001 | Graf et al. |
| 6,235,030 B1 | 5/2001 | Zucherman et al. |
| 6,235,043 B1 | 5/2001 | Reiley et al. |
| 6,238,397 B1 | 5/2001 | Zucherman et al. |
| 6,238,491 B1 | 5/2001 | Davidson et al. |
| 6,241,734 B1 | 6/2001 | Scribner et al. |
| 6,241,769 B1 | 6/2001 | Nicholson et al. |
| 6,245,107 B1 | 6/2001 | Ferree |
| 6,248,108 B1 | 6/2001 | Toermaelae et al. |
| 6,248,110 B1 | 6/2001 | Reiley et al. |
| 6,248,131 B1 | 6/2001 | Felt et al. |
| 6,251,111 B1 | 6/2001 | Barker et al. |
| 6,251,140 B1 | 6/2001 | Marino et al. |
| 6,261,289 B1 | 7/2001 | Levy |
| 6,264,676 B1 | 7/2001 | Gellman et al. |
| 6,264,695 B1 | 7/2001 | Stoy |
| 6,267,763 B1 | 7/2001 | Castro |
| 6,267,765 B1 | 7/2001 | Taylor et al. |
| 6,267,767 B1 | 7/2001 | Strobel et al. |
| 6,277,149 B1 | 8/2001 | Boyle et al. |
| 6,280,444 B1 | 8/2001 | Zucherman et al. |
| 6,280,456 B1 | 8/2001 | Scribner et al. |
| 6,280,474 B1 | 8/2001 | Cassidy et al. |
| 6,280,475 B1 | 8/2001 | Bao et al. |
| 6,287,313 B1 | 9/2001 | Sasso |
| 6,290,724 B1 | 9/2001 | Marino |
| 6,293,909 B1 | 9/2001 | Chu et al. |
| 6,293,952 B1 | 9/2001 | Brosens et al. |
| D449,691 S | 10/2001 | Reiley et al. |
| 6,296,647 B1 | 10/2001 | Robioneck et al. |
| 6,302,914 B1 | 10/2001 | Michelson |
| 6,306,136 B1 | 10/2001 | Baccelli |
| 6,306,177 B1 | 10/2001 | Felt et al. |
| 6,312,443 B1 | 11/2001 | Stone |
| 6,319,254 B1 | 11/2001 | Giet et al. |
| 6,319,272 B1 | 11/2001 | Brenneman et al. |
| 6,331,312 B1 | 12/2001 | Lee et al. |
| 6,332,882 B1 | 12/2001 | Zucherman et al. |
| 6,332,883 B1 | 12/2001 | Zucherman et al. |
| 6,332,894 B1 | 12/2001 | Stalcup et al. |
| 6,332,895 B1 | 12/2001 | Suddaby |
| 6,346,092 B1 | 2/2002 | Leschinsky |
| 6,348,053 B1 | 2/2002 | Cachia |
| 6,355,043 B1 | 3/2002 | Adam |
| 6,361,537 B1 | 3/2002 | Anderson |
| 6,361,538 B1 | 3/2002 | Fenaroli et al. |
| 6,361,557 B1 | 3/2002 | Gittings et al. |
| 6,364,828 B1 | 4/2002 | Yeung et al. |
| 6,364,897 B1 | 4/2002 | Bonutti |
| 6,368,325 B1 | 4/2002 | McKinley et al. |
| 6,368,350 B1 | 4/2002 | Erickson et al. |
| 6,368,351 B1 | 4/2002 | Glenn et al. |
| 6,371,971 B1 | 4/2002 | Tsugita et al. |
| 6,371,989 B1 | 4/2002 | Chauvin et al. |
| 6,375,681 B1 | 4/2002 | Truscott |
| 6,375,682 B1 | 4/2002 | Fleischmann et al. |
| 6,379,355 B1 | 4/2002 | Zucherman et al. |
| 6,379,363 B1 | 4/2002 | Herrington et al. |
| 6,387,130 B1 | 5/2002 | Stone et al. |
| 6,402,750 B1 | 6/2002 | Atkinson et al. |
| 6,409,766 B1 | 6/2002 | Brett |
| 6,409,767 B1 | 6/2002 | Perice et al. |
| 6,413,278 B1 | 7/2002 | Marchosky |
| 6,416,551 B1 | 7/2002 | Keller |
| 6,419,641 B1 | 7/2002 | Mark et al. |
| 6,419,676 B1 | 7/2002 | Zucherman et al. |
| 6,419,677 B2 | 7/2002 | Zucherman et al. |
| 6,419,704 B1 | 7/2002 | Ferree |
| 6,419,705 B1 | 7/2002 | Erickson |
| 6,419,706 B1 | 7/2002 | Graf |
| 6,423,061 B1 | 7/2002 | Bryant |
| 6,423,067 B1 | 7/2002 | Eisermann |
| 6,423,071 B1 | 7/2002 | Lawson |
| 6,423,083 B2 | 7/2002 | Reiley et al. |
| 6,423,089 B1 | 7/2002 | Gingras et al. |
| 6,425,887 B1 | 7/2002 | McGuckin et al. |
| 6,425,919 B1 | 7/2002 | Lambrecht |
| 6,425,920 B1 | 7/2002 | Hamada |
| 6,428,541 B1 | 8/2002 | Boyd et al. |
| 6,428,556 B1 | 8/2002 | Chin |
| 6,436,140 B1 | 8/2002 | Liu et al. |
| 6,436,143 B1 | 8/2002 | Ross et al. |
| 6,440,138 B1 | 8/2002 | Reiley et al. |
| 6,440,154 B2 | 8/2002 | Gellman et al. |
| 6,440,169 B1 | 8/2002 | Elberg et al. |
| 6,443,989 B1 | 9/2002 | Jackson |
| 6,447,527 B1 | 9/2002 | Thompson et al. |
| 6,447,540 B1 | 9/2002 | Fontaine et al. |
| 6,450,989 B2 | 9/2002 | Dubrul et al. |
| 6,451,019 B1 | 9/2002 | Zucherman et al. |
| 6,451,020 B1 | 9/2002 | Zucherman et al. |
| 6,454,806 B1 | 9/2002 | Cohen et al. |
| 6,454,807 B1 | 9/2002 | Jackson |
| 6,458,134 B1 | 10/2002 | Songer et al. |
| 6,468,277 B1 | 10/2002 | Justin et al. |
| 6,468,279 B1 | 10/2002 | Reo |
| 6,468,309 B1 | 10/2002 | Lieberman |
| 6,468,310 B1 | 10/2002 | Ralph et al. |
| 6,471,724 B2 | 10/2002 | Zdeblick et al. |
| 6,475,226 B1 | 11/2002 | Belef et al. |
| 6,478,029 B1 | 11/2002 | Boyd et al. |
| 6,478,796 B2 | 11/2002 | Zucherman et al. |
| 6,478,805 B1 | 11/2002 | Marino et al. |
| 6,482,235 B1 | 11/2002 | Lambrecht et al. |
| 6,485,491 B1 | 11/2002 | Farris et al. |
| 6,485,518 B1 | 11/2002 | Cornwall et al. |
| D467,657 S | 12/2002 | Scribner |
| 6,488,693 B2 | 12/2002 | Gannoe et al. |
| 6,488,710 B2 | 12/2002 | Besselink |
| 6,489,309 B1 | 12/2002 | Singh et al. |
| 6,491,626 B1 | 12/2002 | Stone et al. |
| 6,491,695 B1 | 12/2002 | Roggenbuck |
| 6,491,714 B1 | 12/2002 | Bennett |
| 6,491,724 B1 | 12/2002 | Ferree |
| 6,494,860 B2 | 12/2002 | Rocamora et al. |
| 6,494,883 B1 | 12/2002 | Ferree |
| 6,494,893 B2 | 12/2002 | Dubrul et al. |
| 6,498,421 B1 | 12/2002 | Oh et al. |
| 6,500,178 B2 | 12/2002 | Zucherman et al. |
| 6,500,205 B1 | 12/2002 | Michelson |
| 6,506,192 B1 | 1/2003 | Gertzman et al. |
| 6,508,839 B1 | 1/2003 | Lambrecht et al. |
| 6,511,471 B2 | 1/2003 | Rosenman et al. |
| 6,511,481 B2 | 1/2003 | Von et al. |
| 6,512,958 B1 | 1/2003 | Swoyer et al. |
| D469,871 S | 2/2003 | Sand |
| 6,514,256 B2 | 2/2003 | Zucherman et al. |
| 6,517,543 B1 | 2/2003 | Berrevoets et al. |
| 6,517,580 B1 | 2/2003 | Ramadan et al. |
| 6,520,907 B1 | 2/2003 | Foley et al. |
| 6,520,991 B2 | 2/2003 | Huene |
| D472,323 S | 3/2003 | Sand |
| 6,527,772 B2 | 3/2003 | Enayati |
| 6,527,774 B2 | 3/2003 | Lieberman |
| 6,527,803 B1 | 3/2003 | Crozet et al. |
| 6,527,804 B1 | 3/2003 | Gauchet et al. |
| 6,530,930 B1 | 3/2003 | Marino et al. |
| 6,533,791 B1 | 3/2003 | Betz et al. |
| 6,533,797 B1 | 3/2003 | Stone et al. |
| 6,533,818 B1 | 3/2003 | Weber et al. |

(56) References Cited

U.S. PATENT DOCUMENTS

| | | |
|---|---|---|
| 6,540,747 B1 | 4/2003 | Marino |
| 6,544,265 B2 | 4/2003 | Lieberman |
| 6,547,793 B1 | 4/2003 | McGuire |
| 6,547,795 B2 | 4/2003 | Schneiderman |
| 6,547,823 B2 | 4/2003 | Scarborough et al. |
| 6,551,319 B2 | 4/2003 | Lieberman |
| 6,551,322 B1 | 4/2003 | Lieberman |
| 6,554,831 B1 | 4/2003 | Rivard et al. |
| 6,554,833 B2 | 4/2003 | Levy et al. |
| 6,554,852 B1 | 4/2003 | Oberlander |
| 6,558,389 B2 | 5/2003 | Clark et al. |
| 6,558,390 B2 | 5/2003 | Cragg |
| 6,558,424 B2 | 5/2003 | Thalgott |
| 6,562,046 B2 | 5/2003 | Sasso |
| 6,562,049 B1 | 5/2003 | Norlander et al. |
| 6,562,072 B1 | 5/2003 | Fuss et al. |
| 6,562,074 B2 | 5/2003 | Gerbec et al. |
| 6,575,919 B1 | 6/2003 | Reiley et al. |
| 6,575,979 B1 | 6/2003 | Cragg |
| 6,576,016 B1 | 6/2003 | Hochshuler et al. |
| 6,579,291 B1 | 6/2003 | Keith et al. |
| 6,579,293 B1 | 6/2003 | Chandran |
| 6,579,320 B1 | 6/2003 | Gauchet et al. |
| 6,582,390 B1 | 6/2003 | Sanderson |
| 6,582,431 B1 | 6/2003 | Ray |
| 6,582,433 B2 | 6/2003 | Yun |
| 6,582,437 B2 | 6/2003 | Dorchak et al. |
| 6,582,441 B1 | 6/2003 | He et al. |
| 6,582,453 B1 | 6/2003 | Tran et al. |
| 6,582,466 B1 | 6/2003 | Gauchet |
| 6,582,467 B1 | 6/2003 | Teitelbaum et al. |
| 6,582,468 B1 | 6/2003 | Gauchet |
| 6,585,730 B1 | 7/2003 | Foerster |
| 6,585,740 B2 | 7/2003 | Schlapfer et al. |
| 6,589,240 B2 | 7/2003 | Hinchliffe |
| 6,589,244 B1 | 7/2003 | Sevrain et al. |
| 6,589,249 B2 | 7/2003 | Sater et al. |
| 6,592,553 B2 | 7/2003 | Zhang et al. |
| 6,592,624 B1 | 7/2003 | Fraser et al. |
| 6,592,625 B2 | 7/2003 | Cauthen |
| 6,595,998 B2 | 7/2003 | Johnson et al. |
| 6,596,008 B1 | 7/2003 | Kambin |
| 6,599,294 B2 | 7/2003 | Fuss et al. |
| 6,599,297 B1 | 7/2003 | Carlsson et al. |
| 6,602,293 B1 | 8/2003 | Biermann et al. |
| 6,607,530 B1 | 8/2003 | Carl et al. |
| 6,607,544 B1 | 8/2003 | Boucher et al. |
| 6,607,558 B2 | 8/2003 | Kuras |
| 6,610,091 B1 | 8/2003 | Reiley |
| 6,610,094 B2 | 8/2003 | Husson |
| 6,613,050 B1 | 9/2003 | Wagner et al. |
| 6,613,054 B2 | 9/2003 | Scribner et al. |
| 6,616,678 B2 | 9/2003 | Nishtala et al. |
| 6,620,196 B1 | 9/2003 | Trieu |
| 6,623,505 B2 | 9/2003 | Scribner et al. |
| 6,626,943 B2 | 9/2003 | Eberlein et al. |
| 6,626,944 B1 | 9/2003 | Taylor |
| 6,632,224 B2 | 10/2003 | Cachia et al. |
| 6,632,235 B2 | 10/2003 | Weikel et al. |
| 6,635,059 B2 | 10/2003 | Randall et al. |
| 6,635,362 B2 | 10/2003 | Zheng |
| D482,787 S | 11/2003 | Reiss |
| 6,641,564 B1 | 11/2003 | Kraus |
| 6,641,587 B2 | 11/2003 | Scribner et al. |
| 6,641,614 B1 | 11/2003 | Wagner et al. |
| 6,645,213 B2 | 11/2003 | Sand et al. |
| 6,645,248 B2 | 11/2003 | Casutt |
| 6,648,890 B2 | 11/2003 | Culbert et al. |
| 6,648,893 B2 | 11/2003 | Dudasik |
| 6,648,917 B2 | 11/2003 | Gerbec et al. |
| 6,652,527 B2 | 11/2003 | Zucherman et al. |
| 6,652,592 B1 | 11/2003 | Grooms et al. |
| D483,495 S | 12/2003 | Sand |
| 6,655,962 B1 | 12/2003 | Kennard |
| 6,656,178 B1 | 12/2003 | Veldhuizen et al. |
| 6,656,180 B2 | 12/2003 | Stahurski |
| 6,660,037 B1 | 12/2003 | Husson et al. |
| 6,663,647 B2 | 12/2003 | Reiley et al. |
| 6,666,890 B2 | 12/2003 | Michelson |
| 6,666,891 B2 | 12/2003 | Boehm et al. |
| 6,669,698 B1 | 12/2003 | Tromanhauser et al. |
| 6,669,729 B2 | 12/2003 | Chin |
| 6,669,732 B2 | 12/2003 | Serhan et al. |
| 6,673,074 B2 | 1/2004 | Shluzas |
| 6,676,663 B2 | 1/2004 | Higueras et al. |
| 6,676,664 B1 | 1/2004 | Al-Assir |
| 6,676,665 B2 | 1/2004 | Foley et al. |
| 6,679,833 B2 | 1/2004 | Smith et al. |
| 6,682,535 B2 | 1/2004 | Hoogland |
| 6,682,561 B2 | 1/2004 | Songer et al. |
| 6,682,562 B2 | 1/2004 | Viart et al. |
| 6,685,706 B2 | 2/2004 | Padget et al. |
| 6,685,742 B1 | 2/2004 | Jackson |
| 6,689,125 B1 | 2/2004 | Keith et al. |
| 6,689,152 B2 | 2/2004 | Balceta et al. |
| 6,689,168 B2 | 2/2004 | Lieberman |
| 6,692,499 B2 | 2/2004 | Toermaelae et al. |
| 6,692,563 B2 | 2/2004 | Zimmermann |
| 6,695,842 B2 | 2/2004 | Zucherman et al. |
| 6,695,851 B2 | 2/2004 | Zdeblick et al. |
| 6,699,246 B2 | 3/2004 | Zucherman et al. |
| 6,699,247 B2 | 3/2004 | Zucherman et al. |
| 6,706,070 B1 | 3/2004 | Wagner et al. |
| 6,709,458 B2 | 3/2004 | Michelson |
| 6,712,819 B2 | 3/2004 | Zucherman et al. |
| 6,716,216 B1 | 4/2004 | Boucher et al. |
| 6,716,247 B2 | 4/2004 | Michelson |
| 6,716,957 B2 | 4/2004 | Tunc |
| 6,719,760 B2 | 4/2004 | Dorchak et al. |
| 6,719,761 B1 | 4/2004 | Reiley et al. |
| 6,719,773 B1 | 4/2004 | Boucher et al. |
| 6,719,796 B2 | 4/2004 | Cohen et al. |
| 6,723,096 B1 | 4/2004 | Dorchak et al. |
| 6,723,126 B1 | 4/2004 | Berry |
| 6,723,127 B2 | 4/2004 | Ralph et al. |
| 6,723,128 B2 | 4/2004 | Uk |
| 6,726,691 B2 | 4/2004 | Osorio et al. |
| D490,159 S | 5/2004 | Sand |
| 6,730,126 B2 | 5/2004 | Boehm et al. |
| 6,733,093 B2 | 5/2004 | Deland et al. |
| 6,733,460 B2 | 5/2004 | Ogura |
| 6,733,532 B1 | 5/2004 | Gauchet et al. |
| 6,733,534 B2 | 5/2004 | Sherman |
| 6,733,535 B2 | 5/2004 | Michelson |
| 6,733,635 B1 | 5/2004 | Ozawa et al. |
| 6,740,090 B1 | 5/2004 | Cragg et al. |
| 6,740,093 B2 | 5/2004 | Hochshuler et al. |
| 6,740,117 B2 | 5/2004 | Ralph et al. |
| D492,032 S | 6/2004 | Muller et al. |
| 6,743,166 B2 | 6/2004 | Berci et al. |
| 6,743,255 B2 | 6/2004 | Ferree |
| 6,746,451 B2 | 6/2004 | Middleton et al. |
| 6,749,560 B1 | 6/2004 | Konstorum et al. |
| 6,752,831 B2 | 6/2004 | Sybert et al. |
| 6,755,841 B2 | 6/2004 | Fraser et al. |
| D492,775 S | 7/2004 | Doelling et al. |
| D493,533 S | 7/2004 | Blain |
| 6,758,673 B2 | 7/2004 | Fromovich et al. |
| 6,758,861 B2 | 7/2004 | Ralph et al. |
| 6,758,862 B2 | 7/2004 | Berry et al. |
| 6,761,720 B1 | 7/2004 | Senegas |
| 6,764,514 B1 | 7/2004 | Li et al. |
| D495,417 S | 8/2004 | Doelling et al. |
| 6,770,075 B2 | 8/2004 | Howland |
| 6,773,460 B2 | 8/2004 | Jackson |
| 6,780,151 B2 | 8/2004 | Grabover et al. |
| 6,783,530 B1 | 8/2004 | Levy |
| 6,790,210 B1 | 9/2004 | Cragg et al. |
| 6,793,656 B1 | 9/2004 | Mathews |
| 6,793,678 B2 | 9/2004 | Hawkins |
| 6,793,679 B2 | 9/2004 | Michelson |
| 6,796,983 B1 | 9/2004 | Zucherman et al. |
| 6,805,685 B2 | 10/2004 | Taylor |
| 6,805,695 B2 | 10/2004 | Keith et al. |

(56) References Cited

U.S. PATENT DOCUMENTS

| | | |
|---|---|---|
| 6,805,697 B1 | 10/2004 | Helm et al. |
| 6,805,714 B2 | 10/2004 | Sutcliffe |
| 6,808,526 B1 | 10/2004 | Magerl et al. |
| 6,808,537 B2 | 10/2004 | Michelson |
| 6,814,736 B2 | 11/2004 | Reiley et al. |
| 6,814,756 B1 | 11/2004 | Michelson |
| 6,821,298 B1 | 11/2004 | Jackson |
| 6,830,589 B2 | 12/2004 | Erickson |
| 6,835,205 B2 | 12/2004 | Atkinson et al. |
| 6,835,206 B2 | 12/2004 | Jackson |
| 6,835,208 B2 | 12/2004 | Marchosky |
| 6,840,944 B2 | 1/2005 | Suddaby |
| 6,852,126 B2 | 2/2005 | Ahlgren |
| 6,852,129 B2 | 2/2005 | Gerbec et al. |
| 6,855,167 B2 | 2/2005 | Shimp et al. |
| 6,863,668 B2 | 3/2005 | Gillespie et al. |
| 6,863,672 B2 | 3/2005 | Reiley et al. |
| 6,863,673 B2 | 3/2005 | Gerbec et al. |
| 6,866,682 B1 | 3/2005 | An et al. |
| 6,875,215 B2 | 4/2005 | Taras et al. |
| 6,881,228 B2 | 4/2005 | Zdeblick et al. |
| 6,881,229 B2 | 4/2005 | Khandkar et al. |
| 6,883,520 B2 | 4/2005 | Lambrecht et al. |
| 6,887,243 B2 | 5/2005 | Culbert |
| 6,887,248 B2 | 5/2005 | McKinley et al. |
| 6,890,333 B2 | 5/2005 | Von et al. |
| 6,893,464 B2 | 5/2005 | Kiester |
| 6,893,466 B2 | 5/2005 | Trieu |
| 6,899,716 B2 | 5/2005 | Cragg |
| 6,899,719 B2 | 5/2005 | Reiley et al. |
| 6,899,735 B2 | 5/2005 | Coates et al. |
| D506,828 S | 6/2005 | Layne et al. |
| 6,902,566 B2 | 6/2005 | Zucherman et al. |
| 6,905,512 B2 | 6/2005 | Paes et al. |
| 6,908,465 B2 | 6/2005 | Von et al. |
| 6,908,506 B2 | 6/2005 | Zimmermann |
| 6,916,323 B2 | 7/2005 | Kitchens |
| 6,921,403 B2 | 7/2005 | Cragg et al. |
| 6,923,810 B1 | 8/2005 | Michelson |
| 6,923,811 B1 | 8/2005 | Carl et al. |
| 6,923,813 B1 | 8/2005 | Phillips et al. |
| 6,923,814 B1 | 8/2005 | Hildebrand et al. |
| 6,929,606 B2 | 8/2005 | Ritland |
| 6,929,647 B2 | 8/2005 | Cohen |
| 6,936,071 B1 | 8/2005 | Marnay et al. |
| 6,936,072 B2 | 8/2005 | Lambrecht et al. |
| 6,942,668 B2 | 9/2005 | Padget et al. |
| 6,945,973 B2 | 9/2005 | Bray |
| 6,945,975 B2 | 9/2005 | Dalton |
| 6,946,000 B2 | 9/2005 | Senegas et al. |
| 6,949,100 B1 | 9/2005 | Venturini |
| 6,951,561 B2 | 10/2005 | Warren et al. |
| 6,952,129 B2 | 10/2005 | Lin et al. |
| 6,953,477 B2 | 10/2005 | Berry |
| 6,955,691 B2 | 10/2005 | Chae et al. |
| 6,962,606 B2 | 11/2005 | Michelson |
| 6,964,674 B1 | 11/2005 | Matsuura et al. |
| 6,964,686 B2 | 11/2005 | Gordon |
| 6,966,910 B2 | 11/2005 | Ritland |
| 6,969,404 B2 | 11/2005 | Ferree |
| 6,969,405 B2 | 11/2005 | Suddaby |
| D512,506 S | 12/2005 | Layne et al. |
| 6,972,035 B2 | 12/2005 | Michelson |
| 6,974,479 B2 | 12/2005 | Trieu |
| 6,979,341 B2 | 12/2005 | Scribner et al. |
| 6,979,352 B2 | 12/2005 | Reynolds |
| 6,979,353 B2 | 12/2005 | Bresina |
| 6,981,981 B2 | 1/2006 | Reiley et al. |
| 6,997,929 B2 | 2/2006 | Manzi et al. |
| 7,004,945 B2 | 2/2006 | Boyd et al. |
| 7,004,971 B2 | 2/2006 | Serhan et al. |
| 7,008,431 B2 | 3/2006 | Simonson |
| 7,008,453 B1 | 3/2006 | Michelson |
| 7,014,633 B2 | 3/2006 | Cragg |
| 7,018,089 B2 | 3/2006 | Wenz et al. |
| 7,018,412 B2 | 3/2006 | Ferreira et al. |
| 7,018,415 B1 | 3/2006 | McKay |
| 7,018,416 B2 | 3/2006 | Hanson et al. |
| 7,018,453 B2 | 3/2006 | Klein et al. |
| 7,022,138 B2 | 4/2006 | Mashburn |
| 7,025,746 B2 | 4/2006 | Tal |
| 7,025,787 B2 | 4/2006 | Bryan et al. |
| 7,029,473 B2 | 4/2006 | Zucherman et al. |
| 7,029,498 B2 | 4/2006 | Boehm et al. |
| 7,037,339 B2 | 5/2006 | Houfburg |
| 7,041,107 B2 | 5/2006 | Pohjonen et al. |
| 7,044,954 B2 | 5/2006 | Reiley et al. |
| 7,048,694 B2 | 5/2006 | Mark et al. |
| 7,048,736 B2 | 5/2006 | Robinson et al. |
| 7,060,068 B2 | 6/2006 | Tromanhauser et al. |
| 7,063,701 B2 | 6/2006 | Michelson |
| 7,063,702 B2 | 6/2006 | Michelson |
| 7,063,703 B2 | 6/2006 | Reo |
| 7,066,960 B1 | 6/2006 | Dickman |
| 7,066,961 B2 | 6/2006 | Michelson |
| 7,069,087 B2 | 6/2006 | Sharkey et al. |
| 7,070,598 B2 | 7/2006 | Lim et al. |
| 7,070,601 B2 | 7/2006 | Culbert et al. |
| 7,074,203 B1 | 7/2006 | Johanson et al. |
| 7,074,226 B2 | 7/2006 | Roehm et al. |
| 7,081,120 B2 | 7/2006 | Li et al. |
| 7,081,122 B1 | 7/2006 | Reiley et al. |
| 7,083,650 B2 | 8/2006 | Moskowitz et al. |
| 7,087,055 B2 | 8/2006 | Lim et al. |
| 7,087,083 B2 | 8/2006 | Pasquet et al. |
| 7,094,239 B1 | 8/2006 | Michelson |
| 7,094,257 B2 | 8/2006 | Mujwid et al. |
| 7,094,258 B2 | 8/2006 | Lambrecht et al. |
| 7,101,375 B2 | 9/2006 | Zucherman et al. |
| 7,114,501 B2 | 10/2006 | Johnson et al. |
| 7,115,128 B2 | 10/2006 | Michelson |
| 7,115,163 B2 | 10/2006 | Zimmermann |
| 7,118,572 B2 | 10/2006 | Bramlet et al. |
| 7,118,579 B2 | 10/2006 | Michelson |
| 7,118,580 B1 | 10/2006 | Beyersdorff et al. |
| 7,118,598 B2 | 10/2006 | Michelson |
| 7,124,761 B2 | 10/2006 | Lambrecht et al. |
| 7,128,760 B2 | 10/2006 | Michelson |
| 7,135,424 B2 | 11/2006 | Worley et al. |
| 7,153,304 B2 | 12/2006 | Robie et al. |
| 7,153,305 B2 | 12/2006 | Johnson et al. |
| 7,153,306 B2 | 12/2006 | Ralph et al. |
| 7,153,307 B2 | 12/2006 | Scribner et al. |
| D536,096 S | 1/2007 | Hoogland et al. |
| 7,156,874 B2 | 1/2007 | Paponneau et al. |
| 7,156,875 B2 | 1/2007 | Michelson |
| 7,156,876 B2 | 1/2007 | Moumene et al. |
| 7,163,558 B2 | 1/2007 | Senegas et al. |
| 7,166,107 B2 | 1/2007 | Anderson |
| 7,172,612 B2 | 2/2007 | Ishikawa |
| 7,179,293 B2 | 2/2007 | McKay |
| 7,179,294 B2 | 2/2007 | Eisermann et al. |
| 7,189,242 B2 | 3/2007 | Boyd et al. |
| 7,201,751 B2 | 4/2007 | Zucherman et al. |
| 7,204,851 B2 | 4/2007 | Trieu et al. |
| 7,207,991 B2 | 4/2007 | Michelson |
| 7,211,112 B2 | 5/2007 | Baynham et al. |
| 7,214,227 B2 | 5/2007 | Colleran et al. |
| 7,217,293 B2 | 5/2007 | Branch, Jr. |
| 7,220,280 B2 | 5/2007 | Kast et al. |
| 7,220,281 B2 | 5/2007 | Lambrecht et al. |
| 7,223,227 B2 | 5/2007 | Pflueger |
| 7,223,292 B2 | 5/2007 | Messerli et al. |
| 7,226,481 B2 | 6/2007 | Kuslich |
| 7,226,483 B2 | 6/2007 | Gerber et al. |
| 7,235,101 B2 | 6/2007 | Berry et al. |
| 7,238,204 B2 | 7/2007 | Le et al. |
| 7,241,297 B2 | 7/2007 | Shaolian et al. |
| 7,244,273 B2 | 7/2007 | Pedersen et al. |
| 7,250,060 B2 | 7/2007 | Trieu |
| 7,252,671 B2 | 8/2007 | Scribner et al. |
| 7,267,683 B2 | 9/2007 | Sharkey et al. |
| 7,267,687 B2 | 9/2007 | McGuckin, Jr. |
| 7,270,679 B2 | 9/2007 | Istephanous et al. |

(56) References Cited

U.S. PATENT DOCUMENTS

| | | |
|---|---|---|
| 7,276,062 B2 | 10/2007 | McDaniel et al. |
| 7,282,061 B2 | 10/2007 | Sharkey et al. |
| 7,291,173 B2 | 11/2007 | Richelsoph et al. |
| 7,300,440 B2 | 11/2007 | Zdeblick et al. |
| 7,306,628 B2 | 12/2007 | Zucherman et al. |
| 7,309,357 B2 | 12/2007 | Kim |
| 7,311,713 B2 | 12/2007 | Johnson et al. |
| 7,316,714 B2 | 1/2008 | Gordon et al. |
| 7,318,840 B2 | 1/2008 | McKay |
| 7,320,689 B2 | 1/2008 | Keller |
| 7,320,708 B1 | 1/2008 | Bernstein |
| 7,322,962 B2 | 1/2008 | Forrest |
| 7,326,211 B2 | 2/2008 | Padget et al. |
| 7,326,248 B2 | 2/2008 | Michelson |
| 7,335,203 B2 | 2/2008 | Winslow et al. |
| 7,361,140 B2 | 4/2008 | Ries et al. |
| 7,371,238 B2 | 5/2008 | Soboleski et al. |
| 7,377,942 B2 | 5/2008 | Berry |
| 7,383,639 B2 | 6/2008 | Malandain |
| 7,400,930 B2 | 7/2008 | Sharkey et al. |
| 7,410,501 B2 | 8/2008 | Michelson |
| 7,413,576 B2 | 8/2008 | Sybert et al. |
| 7,422,594 B2 | 9/2008 | Zander |
| 7,434,325 B2 | 10/2008 | Foley et al. |
| 7,442,211 B2 | 10/2008 | De et al. |
| 7,445,636 B2 | 11/2008 | Michelson |
| 7,445,637 B2 | 11/2008 | Taylor |
| D584,812 S | 1/2009 | Ries |
| 7,473,256 B2 | 1/2009 | Assell et al. |
| 7,473,268 B2 | 1/2009 | Zucherman et al. |
| 7,476,251 B2 | 1/2009 | Zucherman et al. |
| 7,485,134 B2 | 2/2009 | Simonson |
| 7,488,326 B2 | 2/2009 | Elliott |
| 7,500,991 B2 | 3/2009 | Bartish et al. |
| 7,503,920 B2 | 3/2009 | Siegal |
| 7,503,933 B2 | 3/2009 | Michelson |
| 7,507,241 B2 | 3/2009 | Levy et al. |
| 7,517,363 B2 | 4/2009 | Rogers et al. |
| 7,520,888 B2 | 4/2009 | Trieu |
| 7,547,317 B2 | 6/2009 | Cragg |
| 7,556,629 B2 | 7/2009 | Von et al. |
| 7,556,651 B2 | 7/2009 | Humphreys et al. |
| 7,569,054 B2 | 8/2009 | Michelson |
| 7,569,074 B2 | 8/2009 | Eisermann et al. |
| 7,575,599 B2 | 8/2009 | Villiers et al. |
| 7,588,574 B2 | 9/2009 | Assell et al. |
| 7,608,083 B2 | 10/2009 | Lee et al. |
| 7,618,458 B2 | 11/2009 | Biedermann et al. |
| 7,621,950 B1 | 11/2009 | Globerman et al. |
| 7,621,960 B2 | 11/2009 | Boyd et al. |
| 7,625,378 B2 | 12/2009 | Foley |
| 7,637,905 B2 | 12/2009 | Saadat et al. |
| 7,641,657 B2 | 1/2010 | Cragg |
| 7,641,670 B2 | 1/2010 | Davison et al. |
| 7,641,692 B2 | 1/2010 | Bryan et al. |
| 7,647,123 B2 | 1/2010 | Sharkey et al. |
| 7,648,523 B2 | 1/2010 | Mirkovic et al. |
| 7,655,010 B2 | 2/2010 | Serhan et al. |
| 7,666,266 B2 | 2/2010 | Izawa et al. |
| 7,670,354 B2 | 3/2010 | Davison et al. |
| 7,670,374 B2 | 3/2010 | Schaller |
| 7,674,273 B2 | 3/2010 | Davison et al. |
| 7,682,370 B2 | 3/2010 | Pagliuca et al. |
| 7,691,120 B2 | 4/2010 | Shluzas et al. |
| 7,691,147 B2 | 4/2010 | Guetlin et al. |
| 7,699,878 B2 | 4/2010 | Pavlov et al. |
| 7,703,727 B2 | 4/2010 | Selness |
| 7,717,944 B2 | 5/2010 | Foley et al. |
| 7,722,530 B2 | 5/2010 | Davison |
| 7,722,612 B2 | 5/2010 | Sala et al. |
| 7,722,674 B1 | 5/2010 | Grotz |
| 7,727,263 B2 | 6/2010 | Cragg |
| 7,740,633 B2 | 6/2010 | Assell et al. |
| 7,744,599 B2 | 6/2010 | Cragg |
| 7,744,650 B2 | 6/2010 | Lindner et al. |
| 7,749,270 B2 | 7/2010 | Peterman |
| 7,762,995 B2 | 7/2010 | Eversull et al. |
| 7,763,025 B2 | 7/2010 | Ainsworth et al. |
| 7,763,055 B2 | 7/2010 | Foley |
| 7,766,930 B2 | 8/2010 | Dipoto et al. |
| 7,771,473 B2 | 8/2010 | Thramann |
| 7,771,479 B2 | 8/2010 | Humphreys et al. |
| 7,785,368 B2 | 8/2010 | Schaller |
| 7,789,914 B2 | 9/2010 | Michelson |
| 7,794,463 B2 | 9/2010 | Cragg |
| 7,799,032 B2 | 9/2010 | Assell et al. |
| 7,799,033 B2 | 9/2010 | Assell et al. |
| 7,799,036 B2 | 9/2010 | Davison et al. |
| 7,799,080 B2 | 9/2010 | Doty |
| 7,799,081 B2 | 9/2010 | McKinley |
| 7,799,083 B2 | 9/2010 | Smith et al. |
| D626,233 S | 10/2010 | Cipoletti et al. |
| 7,814,429 B2 | 10/2010 | Buffet et al. |
| 7,819,921 B2 | 10/2010 | Grotz |
| 7,824,410 B2 | 11/2010 | Simonson et al. |
| 7,824,429 B2 | 11/2010 | Culbert et al. |
| 7,824,445 B2 | 11/2010 | Biro et al. |
| 7,828,807 B2 | 11/2010 | Lehuec et al. |
| 7,837,734 B2 | 11/2010 | Zucherman et al. |
| 7,846,183 B2 | 12/2010 | Blain |
| 7,846,206 B2 | 12/2010 | Oglaza et al. |
| 7,850,695 B2 | 12/2010 | Pagliuca et al. |
| 7,850,733 B2 | 12/2010 | Baynham et al. |
| 7,854,766 B2 | 12/2010 | Moskowitz et al. |
| 7,857,832 B2 | 12/2010 | Culbert et al. |
| 7,857,840 B2 | 12/2010 | Krebs et al. |
| 7,862,590 B2 | 1/2011 | Lim et al. |
| 7,862,595 B2 | 1/2011 | Foley et al. |
| 7,867,259 B2 | 1/2011 | Foley et al. |
| 7,874,980 B2 | 1/2011 | Sonnenschein et al. |
| 7,875,077 B2 | 1/2011 | Humphreys et al. |
| 7,879,098 B1 | 2/2011 | Simmons, Jr. |
| 7,887,589 B2 | 2/2011 | Glenn et al. |
| 7,892,171 B2 | 2/2011 | Davison et al. |
| 7,892,249 B2 | 2/2011 | Davison et al. |
| 7,901,438 B2 | 3/2011 | Culbert et al. |
| 7,901,459 B2 | 3/2011 | Hodges et al. |
| 7,909,870 B2 | 3/2011 | Kraus |
| 7,918,874 B2 | 4/2011 | Siegal |
| 7,922,729 B2 | 4/2011 | Michelson |
| 7,931,689 B2 | 4/2011 | Hochschuler et al. |
| 7,935,051 B2 | 5/2011 | Miles et al. |
| 7,938,832 B2 | 5/2011 | Culbert et al. |
| 7,942,903 B2 | 5/2011 | Moskowitz et al. |
| 7,947,078 B2 | 5/2011 | Siegal |
| 7,951,199 B2 | 5/2011 | Miller |
| 7,955,391 B2 | 6/2011 | Schaller |
| 7,959,675 B2 | 6/2011 | Gately |
| 7,963,993 B2 | 6/2011 | Schaller |
| 7,967,864 B2 | 6/2011 | Schaller |
| 7,967,865 B2 | 6/2011 | Schaller |
| 7,985,231 B2 | 7/2011 | Sankaran |
| 7,993,403 B2 | 8/2011 | Foley et al. |
| 7,998,176 B2 | 8/2011 | Culbert |
| 8,007,535 B2 | 8/2011 | Hudgins et al. |
| 8,021,424 B2 | 9/2011 | Beger et al. |
| 8,021,426 B2 | 9/2011 | Segal et al. |
| 8,025,697 B2 | 9/2011 | McClellan et al. |
| 8,034,109 B2 | 10/2011 | Zwirkoski |
| 8,043,381 B2 | 10/2011 | Hestad et al. |
| 8,052,754 B2 | 11/2011 | Froehlich |
| 8,057,544 B2 | 11/2011 | Schaller |
| 8,057,545 B2 | 11/2011 | Hughes et al. |
| 8,062,375 B2 | 11/2011 | Glerum et al. |
| 8,075,621 B2 | 12/2011 | Michelson |
| 8,097,036 B2 | 1/2012 | Cordaro et al. |
| 8,105,382 B2 | 1/2012 | Olmos et al. |
| 8,109,977 B2 | 2/2012 | Culbert et al. |
| 8,114,088 B2 | 2/2012 | Miller |
| 8,118,871 B2 | 2/2012 | Gordon |
| 8,128,700 B2 | 3/2012 | Delurio et al. |
| 8,133,232 B2 | 3/2012 | Levy et al. |
| 8,177,812 B2 | 5/2012 | Sankaran |
| 8,187,327 B2 | 5/2012 | Edidin et al. |

(56) References Cited

U.S. PATENT DOCUMENTS

| | | |
|---|---|---|
| 8,192,495 B2 | 6/2012 | Simpson et al. |
| 8,202,322 B2 | 6/2012 | Doty |
| 8,206,423 B2 | 6/2012 | Siegal |
| 8,216,312 B2 | 7/2012 | Gray |
| 8,216,314 B2 | 7/2012 | Richelsoph |
| 8,221,501 B2 | 7/2012 | Eisermann et al. |
| 8,221,502 B2 | 7/2012 | Branch, Jr. |
| 8,221,503 B2 | 7/2012 | Garcia et al. |
| 8,231,681 B2 | 7/2012 | Castleman et al. |
| 8,236,029 B2 | 8/2012 | Siegal |
| 8,236,058 B2 | 8/2012 | Fabian et al. |
| 8,241,328 B2 | 8/2012 | Siegal |
| 8,241,358 B2 | 8/2012 | Butler et al. |
| 8,241,361 B2 | 8/2012 | Link |
| 8,246,622 B2 | 8/2012 | Siegal et al. |
| 8,257,440 B2 | 9/2012 | Gordon |
| 8,257,442 B2 | 9/2012 | Edie et al. |
| 8,262,666 B2 | 9/2012 | Baynham et al. |
| 8,262,736 B2 | 9/2012 | Michelson |
| 8,267,939 B2 | 9/2012 | Cipoletti et al. |
| 8,267,965 B2 | 9/2012 | Gimbel et al. |
| 8,273,128 B2 | 9/2012 | Oh et al. |
| 8,273,129 B2 | 9/2012 | Baynham et al. |
| 8,287,599 B2 | 10/2012 | McGuckin, Jr. |
| 8,292,959 B2 | 10/2012 | Webb et al. |
| 8,303,663 B2 | 11/2012 | Jimenez et al. |
| 8,317,866 B2 | 11/2012 | Palmatier et al. |
| 8,323,345 B2 | 12/2012 | Sledge |
| 8,328,812 B2 | 12/2012 | Siegal et al. |
| 8,328,852 B2 | 12/2012 | Zehavi et al. |
| 8,337,559 B2 | 12/2012 | Hansell et al. |
| 8,343,193 B2 | 1/2013 | Johnson et al. |
| 8,353,961 B2 | 1/2013 | McClintock et al. |
| 8,361,154 B2 | 1/2013 | Reo |
| 8,366,777 B2 | 2/2013 | Matthis et al. |
| 8,377,098 B2 | 2/2013 | Landry et al. |
| 8,382,842 B2 | 2/2013 | Greenhalgh et al. |
| 8,394,129 B2 | 3/2013 | Morgenstern et al. |
| 8,398,712 B2 | 3/2013 | De et al. |
| 8,398,713 B2 | 3/2013 | Weiman |
| 8,403,990 B2 | 3/2013 | Dryer et al. |
| 8,409,290 B2 | 4/2013 | Zamani et al. |
| 8,409,291 B2 | 4/2013 | Blackwell et al. |
| 8,414,650 B2 | 4/2013 | Bertele et al. |
| 8,435,298 B2 | 5/2013 | Weiman |
| 8,454,617 B2 | 6/2013 | Schaller et al. |
| 8,454,698 B2 | 6/2013 | De et al. |
| 8,465,524 B2 | 6/2013 | Siegal |
| 8,480,715 B2 | 7/2013 | Gray |
| 8,480,742 B2 | 7/2013 | Pisharodi |
| 8,486,109 B2 | 7/2013 | Siegal |
| 8,486,148 B2 | 7/2013 | Butler et al. |
| 8,491,591 B2 | 7/2013 | Fuerderer |
| 8,491,657 B2 | 7/2013 | Attia et al. |
| 8,491,659 B2 | 7/2013 | Weiman |
| 8,506,635 B2 | 8/2013 | Palmatier et al. |
| 8,518,087 B2 | 8/2013 | Lopez et al. |
| 8,518,120 B2 | 8/2013 | Glerum et al. |
| 8,535,380 B2 | 9/2013 | Greenhalgh et al. |
| 8,545,567 B1 | 10/2013 | Krueger |
| 8,551,173 B2 | 10/2013 | Lechmann et al. |
| 8,556,978 B2 | 10/2013 | Schaller |
| 8,556,979 B2 | 10/2013 | Glerum et al. |
| 8,568,481 B2 | 10/2013 | Olmos et al. |
| 8,579,977 B2 | 11/2013 | Fabian |
| 8,579,981 B2 | 11/2013 | Lim et al. |
| 8,591,583 B2 | 11/2013 | Schaller et al. |
| 8,591,585 B2 | 11/2013 | McLaughlin et al. |
| 8,597,330 B2 | 12/2013 | Siegal |
| 8,597,333 B2 | 12/2013 | Morgenstern et al. |
| 8,597,360 B2 | 12/2013 | McLuen et al. |
| 8,603,168 B2 | 12/2013 | Gordon et al. |
| 8,603,170 B2 | 12/2013 | Cipoletti et al. |
| 8,603,177 B2 | 12/2013 | Gray |
| 8,623,091 B2 | 1/2014 | Suedkamp et al. |
| 8,628,576 B2 | 1/2014 | Triplett et al. |
| 8,628,578 B2 | 1/2014 | Miller et al. |
| 8,632,595 B2 | 1/2014 | Weiman |
| 8,641,764 B2 | 2/2014 | Gately |
| 8,663,329 B2 | 3/2014 | Ernst |
| 8,668,740 B2 | 3/2014 | Rhoda et al. |
| 8,672,977 B2 | 3/2014 | Siegal et al. |
| 8,679,183 B2 | 3/2014 | Glerum et al. |
| 8,685,095 B2 | 4/2014 | Miller et al. |
| 8,685,098 B2 | 4/2014 | Glerum et al. |
| 8,696,751 B2 | 4/2014 | Ashley et al. |
| 8,709,086 B2 | 4/2014 | Glerum |
| 8,715,351 B1 | 5/2014 | Pinto |
| 8,721,723 B2 | 5/2014 | Hansell et al. |
| 8,728,160 B2 | 5/2014 | Globerman et al. |
| 8,728,166 B2 | 5/2014 | Schwab |
| 8,753,398 B2 | 6/2014 | Gordon et al. |
| 8,758,441 B2 | 6/2014 | Hovda et al. |
| 8,764,806 B2 | 7/2014 | Abdou |
| 8,771,360 B2 | 7/2014 | Jimenez et al. |
| 8,777,993 B2 | 7/2014 | Siegal et al. |
| 8,778,025 B2 | 7/2014 | Ragab et al. |
| 8,795,366 B2 | 8/2014 | Varela |
| 8,795,374 B2 | 8/2014 | Chee |
| 8,801,787 B2 | 8/2014 | Schaller |
| 8,801,792 B2 | 8/2014 | De et al. |
| 8,808,376 B2 | 8/2014 | Schaller |
| 8,828,085 B1 | 9/2014 | Jensen |
| 8,845,638 B2 | 9/2014 | Siegal et al. |
| 8,845,728 B1 | 9/2014 | Abdou |
| 8,845,731 B2 | 9/2014 | Weiman |
| 8,845,732 B2 | 9/2014 | Weiman |
| 8,845,734 B2 | 9/2014 | Weiman |
| 8,852,242 B2 | 10/2014 | Morgenstern et al. |
| 8,852,243 B2 | 10/2014 | Morgenstern et al. |
| 8,852,279 B2 | 10/2014 | Weiman |
| 8,864,833 B2 | 10/2014 | Glerum et al. |
| 8,888,853 B2 | 11/2014 | Glerum et al. |
| 8,888,854 B2 | 11/2014 | Glerum et al. |
| 8,900,235 B2 | 12/2014 | Siegal |
| 8,900,307 B2 | 12/2014 | Hawkins et al. |
| 8,906,098 B2 | 12/2014 | Siegal |
| 8,926,704 B2 | 1/2015 | Glerum et al. |
| 8,936,641 B2 | 1/2015 | Cain |
| 8,940,052 B2 | 1/2015 | Lechmann et al. |
| 8,961,609 B2 | 2/2015 | Schaller |
| 8,979,929 B2 | 3/2015 | Schaller |
| 8,986,387 B1 | 3/2015 | To et al. |
| 8,986,388 B2 | 3/2015 | Siegal et al. |
| 9,005,291 B2 | 4/2015 | Loebl et al. |
| 9,017,408 B2 | 4/2015 | Siegal et al. |
| 9,017,413 B2 | 4/2015 | Siegal et al. |
| 9,039,767 B2 | 5/2015 | Raymond et al. |
| 9,039,771 B2 | 5/2015 | Glerum et al. |
| 9,044,334 B2 | 6/2015 | Siegal et al. |
| 9,044,338 B2 | 6/2015 | Schaller |
| 9,060,876 B1 | 6/2015 | To et al. |
| 9,066,808 B2 | 6/2015 | Schaller |
| 9,078,767 B1 | 7/2015 | McLean |
| 9,089,428 B2 | 7/2015 | Bertele et al. |
| 9,095,446 B2 | 8/2015 | Landry et al. |
| 9,095,447 B2 | 8/2015 | Barreiro et al. |
| 9,101,488 B2 | 8/2015 | Malandain |
| 9,101,489 B2 | 8/2015 | Protopsaltis et al. |
| 9,107,766 B1 | 8/2015 | McLean et al. |
| 9,254,138 B2 | 2/2016 | Siegal et al. |
| 9,259,326 B2 | 2/2016 | Schaller |
| 9,277,928 B2 | 3/2016 | Morgenstern Lopez |
| 9,283,092 B2 | 3/2016 | Siegal et al. |
| 9,295,562 B2 | 3/2016 | Lechmann et al. |
| 9,326,866 B2 | 5/2016 | Schaller et al. |
| 9,333,091 B2 | 5/2016 | Dimauro |
| 9,387,087 B2 | 7/2016 | Tyber |
| 9,402,739 B2 | 8/2016 | Weiman et al. |
| 9,408,712 B2 | 8/2016 | Siegal et al. |
| 9,414,923 B2 | 8/2016 | Studer et al. |
| 9,414,934 B2 | 8/2016 | Cain |
| 9,433,510 B2 | 9/2016 | Lechmann et al. |
| 9,439,776 B2 | 9/2016 | Dimauro et al. |

(56) References Cited

U.S. PATENT DOCUMENTS

| | | |
|---|---|---|
| 9,439,777 B2 | 9/2016 | Dimauro |
| 9,463,099 B2 | 10/2016 | Levy et al. |
| 9,510,954 B2 | 12/2016 | Glerum et al. |
| 9,592,129 B2 | 3/2017 | Slivka et al. |
| 9,597,197 B2 | 3/2017 | Lechmann et al. |
| 9,724,207 B2 | 8/2017 | Dimauro et al. |
| 9,730,803 B2 | 8/2017 | Dimauro et al. |
| 9,788,963 B2 | 10/2017 | Aquino et al. |
| 9,801,729 B2 | 10/2017 | Dimauro et al. |
| 9,808,351 B2 | 11/2017 | Kelly et al. |
| 9,814,589 B2 | 11/2017 | Dimauro |
| 9,814,590 B2 | 11/2017 | Serhan et al. |
| 9,833,334 B2 | 12/2017 | Voellmicke et al. |
| 9,925,060 B2 | 3/2018 | Dimauro et al. |
| 9,949,769 B2 | 4/2018 | Serhan et al. |
| 10,085,843 B2 | 10/2018 | Dimauro |
| 10,238,500 B2 | 3/2019 | Rogers et al. |
| 10,307,254 B2 | 6/2019 | Levy et al. |
| 10,376,372 B2 | 8/2019 | Serhan et al. |
| 10,398,563 B2 | 9/2019 | Engstrom |
| 10,405,986 B2 | 9/2019 | Kelly et al. |
| 10,420,651 B2 | 9/2019 | Serhan et al. |
| 10,433,971 B2 | 10/2019 | Dimauro et al. |
| 10,433,974 B2 | 10/2019 | O'Neil |
| 10,492,918 B2 | 12/2019 | Dimauro |
| 10,512,489 B2 | 12/2019 | Serhan et al. |
| 10,555,817 B2 | 2/2020 | Dimauro et al. |
| 10,575,959 B2 | 3/2020 | Dimauro et al. |
| 10,583,013 B2 | 3/2020 | Dimauro et al. |
| 10,639,164 B2 | 5/2020 | Dimauro et al. |
| 2001/0011174 A1 | 8/2001 | Reiley et al. |
| 2001/0012950 A1 | 8/2001 | Nishtala et al. |
| 2001/0016741 A1 | 8/2001 | Burkus et al. |
| 2001/0027320 A1 | 10/2001 | Sasso |
| 2001/0037126 A1 | 11/2001 | Stack et al. |
| 2001/0039452 A1 | 11/2001 | Zucherman et al. |
| 2001/0039453 A1 | 11/2001 | Gresser et al. |
| 2001/0049529 A1 | 12/2001 | Cachia et al. |
| 2001/0049530 A1 | 12/2001 | Culbert et al. |
| 2001/0049531 A1 | 12/2001 | Reiley et al. |
| 2001/0056302 A1 | 12/2001 | Boyer et al. |
| 2002/0001476 A1 | 1/2002 | Nagamine et al. |
| 2002/0010070 A1 | 1/2002 | Cales et al. |
| 2002/0016583 A1 | 2/2002 | Cragg |
| 2002/0026195 A1 | 2/2002 | Layne et al. |
| 2002/0026244 A1 | 2/2002 | Trieu |
| 2002/0029084 A1 | 3/2002 | Paul et al. |
| 2002/0032462 A1 | 3/2002 | Houser et al. |
| 2002/0032483 A1 | 3/2002 | Nicholson et al. |
| 2002/0035400 A1 | 3/2002 | Bryan et al. |
| 2002/0037799 A1 | 3/2002 | Li et al. |
| 2002/0045904 A1 | 4/2002 | Fuss et al. |
| 2002/0045942 A1 | 4/2002 | Ham |
| 2002/0055740 A1 | 5/2002 | Lieberman |
| 2002/0055781 A1 | 5/2002 | Sazy |
| 2002/0058947 A1 | 5/2002 | Hochschuler et al. |
| 2002/0068974 A1 | 6/2002 | Kuslich et al. |
| 2002/0068976 A1 | 6/2002 | Jackson |
| 2002/0068977 A1 | 6/2002 | Jackson |
| 2002/0077700 A1 | 6/2002 | Varga et al. |
| 2002/0077701 A1 | 6/2002 | Kuslich |
| 2002/0082584 A1 | 6/2002 | Rosenman et al. |
| 2002/0082608 A1 | 6/2002 | Reiley et al. |
| 2002/0087152 A1 | 7/2002 | Mikus et al. |
| 2002/0087163 A1 | 7/2002 | Dixon et al. |
| 2002/0091387 A1 | 7/2002 | Hoogland |
| 2002/0091390 A1 | 7/2002 | Michelson |
| 2002/0099385 A1 | 7/2002 | Ralph et al. |
| 2002/0107519 A1 | 8/2002 | Dixon et al. |
| 2002/0107573 A1 | 8/2002 | Steinberg |
| 2002/0120335 A1 | 8/2002 | Angelucci et al. |
| 2002/0128713 A1 | 9/2002 | Ferree |
| 2002/0128715 A1 | 9/2002 | Bryan et al. |
| 2002/0128716 A1 | 9/2002 | Cohen et al. |
| 2002/0138146 A1 | 9/2002 | Jackson |
| 2002/0143331 A1 | 10/2002 | Zucherman et al. |
| 2002/0143334 A1 | 10/2002 | Hoffmann et al. |
| 2002/0143335 A1 | 10/2002 | Von et al. |
| 2002/0151895 A1 | 10/2002 | Soboleski et al. |
| 2002/0151976 A1 | 10/2002 | Foley et al. |
| 2002/0156482 A1 | 10/2002 | Scribner et al. |
| 2002/0161444 A1 | 10/2002 | Choi |
| 2002/0165612 A1 | 11/2002 | Gerber et al. |
| 2002/0169471 A1 | 11/2002 | Ferdinand |
| 2002/0172851 A1 | 11/2002 | Corey et al. |
| 2002/0173796 A1 | 11/2002 | Cragg |
| 2002/0173841 A1 | 11/2002 | Ortiz et al. |
| 2002/0173851 A1 | 11/2002 | McKay |
| 2002/0183761 A1 | 12/2002 | Johnson et al. |
| 2002/0183778 A1 | 12/2002 | Reiley et al. |
| 2002/0183848 A1 | 12/2002 | Ray et al. |
| 2002/0191487 A1 | 12/2002 | Sand |
| 2002/0193883 A1 | 12/2002 | Wironen |
| 2002/0198526 A1 | 12/2002 | Shaolian et al. |
| 2003/0004575 A1 | 1/2003 | Erickson |
| 2003/0004576 A1 | 1/2003 | Thalgott |
| 2003/0006942 A1 | 1/2003 | Searls et al. |
| 2003/0014112 A1 | 1/2003 | Ralph et al. |
| 2003/0014116 A1 | 1/2003 | Ralph et al. |
| 2003/0018390 A1 | 1/2003 | Husson |
| 2003/0023305 A1 | 1/2003 | McKay |
| 2003/0028250 A1 | 2/2003 | Reiley et al. |
| 2003/0028251 A1 | 2/2003 | Mathews |
| 2003/0032963 A1 | 2/2003 | Reiss et al. |
| 2003/0040796 A1 | 2/2003 | Ferree |
| 2003/0040799 A1 | 2/2003 | Boyd et al. |
| 2003/0045937 A1 | 3/2003 | Ginn |
| 2003/0045939 A1 | 3/2003 | Casutt |
| 2003/0050644 A1 | 3/2003 | Boucher et al. |
| 2003/0063582 A1 | 4/2003 | Mizell et al. |
| 2003/0065330 A1 | 4/2003 | Zucherman et al. |
| 2003/0065396 A1 | 4/2003 | Michelson |
| 2003/0069582 A1 | 4/2003 | Culbert |
| 2003/0069593 A1 | 4/2003 | Tremulis et al. |
| 2003/0069642 A1 | 4/2003 | Ralph et al. |
| 2003/0073998 A1 | 4/2003 | Pagliuca et al. |
| 2003/0074075 A1 | 4/2003 | Thomas et al. |
| 2003/0078667 A1 | 4/2003 | Manasas et al. |
| 2003/0083642 A1 | 5/2003 | Boyd et al. |
| 2003/0083688 A1 | 5/2003 | Simonson |
| 2003/0108588 A1 | 6/2003 | Chen et al. |
| 2003/0130664 A1 | 7/2003 | Boucher et al. |
| 2003/0130739 A1 | 7/2003 | Gerbec et al. |
| 2003/0135275 A1 | 7/2003 | Garcia et al. |
| 2003/0139648 A1 | 7/2003 | Foley et al. |
| 2003/0139812 A1 | 7/2003 | Garcia et al. |
| 2003/0139813 A1 | 7/2003 | Messerli et al. |
| 2003/0153874 A1 | 8/2003 | Tal |
| 2003/0171812 A1 | 9/2003 | Grunberg et al. |
| 2003/0187431 A1 | 10/2003 | Simonson |
| 2003/0187445 A1 | 10/2003 | Keith et al. |
| 2003/0187506 A1 | 10/2003 | Ross et al. |
| 2003/0191414 A1 | 10/2003 | Reiley et al. |
| 2003/0191489 A1 | 10/2003 | Reiley et al. |
| 2003/0195518 A1 | 10/2003 | Cragg |
| 2003/0195547 A1 | 10/2003 | Scribner et al. |
| 2003/0195630 A1 | 10/2003 | Ferree |
| 2003/0199979 A1 | 10/2003 | McGuckin |
| 2003/0204261 A1 | 10/2003 | Eisermann et al. |
| 2003/0208122 A1 | 11/2003 | Melkent et al. |
| 2003/0208136 A1 | 11/2003 | Mark et al. |
| 2003/0208220 A1 | 11/2003 | Worley et al. |
| 2003/0215344 A1 | 11/2003 | Condon et al. |
| 2003/0220643 A1 | 11/2003 | Ferree |
| 2003/0220648 A1 | 11/2003 | Osorio et al. |
| 2003/0220695 A1 | 11/2003 | Sevrain |
| 2003/0229350 A1 | 12/2003 | Kay |
| 2003/0229372 A1 | 12/2003 | Reiley et al. |
| 2003/0233096 A1 | 12/2003 | Osorio et al. |
| 2003/0233102 A1 | 12/2003 | Nakamura et al. |
| 2003/0233145 A1 | 12/2003 | Landry et al. |
| 2003/0233146 A1 | 12/2003 | Grinberg et al. |
| 2004/0002761 A1 | 1/2004 | Rogers et al. |
| 2004/0006391 A1 | 1/2004 | Reiley |

(56) References Cited

U.S. PATENT DOCUMENTS

| | | |
|---|---|---|
| 2004/0008949 A1 | 1/2004 | Liu et al. |
| 2004/0010251 A1 | 1/2004 | Pitaru et al. |
| 2004/0010260 A1 | 1/2004 | Scribner et al. |
| 2004/0010263 A1 | 1/2004 | Boucher et al. |
| 2004/0010318 A1 | 1/2004 | Ferree |
| 2004/0019354 A1 | 1/2004 | Johnson et al. |
| 2004/0019359 A1 | 1/2004 | Worley et al. |
| 2004/0024408 A1 | 2/2004 | Burkus et al. |
| 2004/0024409 A1 | 2/2004 | Sand et al. |
| 2004/0024410 A1 | 2/2004 | Olson et al. |
| 2004/0024463 A1 | 2/2004 | Thomas et al. |
| 2004/0024465 A1 | 2/2004 | Lambrecht et al. |
| 2004/0030387 A1 | 2/2004 | Landry et al. |
| 2004/0034343 A1 | 2/2004 | Gillespie et al. |
| 2004/0034429 A1 | 2/2004 | Lambrecht et al. |
| 2004/0049190 A1 | 3/2004 | Biedermann et al. |
| 2004/0049203 A1 | 3/2004 | Scribner et al. |
| 2004/0049223 A1 | 3/2004 | Nishtala et al. |
| 2004/0049270 A1 | 3/2004 | Gewirtz |
| 2004/0054412 A1 | 3/2004 | Gerbec et al. |
| 2004/0059333 A1 | 3/2004 | Carl et al. |
| 2004/0059339 A1 | 3/2004 | Roehm et al. |
| 2004/0059350 A1 | 3/2004 | Gordon et al. |
| 2004/0059418 A1 | 3/2004 | McKay et al. |
| 2004/0064144 A1 | 4/2004 | Johnson et al. |
| 2004/0073308 A1 | 4/2004 | Kuslich et al. |
| 2004/0073310 A1 | 4/2004 | Moumene et al. |
| 2004/0082953 A1 | 4/2004 | Petit |
| 2004/0087947 A1 | 5/2004 | Lim et al. |
| 2004/0088055 A1 | 5/2004 | Hanson et al. |
| 2004/0092933 A1 | 5/2004 | Shaolian et al. |
| 2004/0092948 A1 | 5/2004 | Stevens et al. |
| 2004/0092988 A1 | 5/2004 | Shaolian et al. |
| 2004/0093083 A1 | 5/2004 | Branch |
| 2004/0097924 A1 | 5/2004 | Lambrecht et al. |
| 2004/0097930 A1 | 5/2004 | Justis et al. |
| 2004/0097932 A1 | 5/2004 | Ray et al. |
| 2004/0097941 A1 | 5/2004 | Weiner et al. |
| 2004/0097973 A1 | 5/2004 | Loshakove et al. |
| 2004/0098131 A1 | 5/2004 | Bryan et al. |
| 2004/0102774 A1 | 5/2004 | Trieu |
| 2004/0106925 A1 | 6/2004 | Culbert |
| 2004/0106940 A1 | 6/2004 | Shaolian et al. |
| 2004/0111161 A1 | 6/2004 | Trieu |
| 2004/0116997 A1 | 6/2004 | Taylor et al. |
| 2004/0117019 A1 | 6/2004 | Trieu et al. |
| 2004/0117022 A1 | 6/2004 | Marnay et al. |
| 2004/0127906 A1 | 7/2004 | Culbert et al. |
| 2004/0127990 A1 | 7/2004 | Bartish et al. |
| 2004/0127991 A1 | 7/2004 | Ferree |
| 2004/0133124 A1 | 7/2004 | Bates et al. |
| 2004/0133229 A1 | 7/2004 | Lambrecht et al. |
| 2004/0133279 A1 | 7/2004 | Krueger et al. |
| 2004/0133280 A1 | 7/2004 | Trieu |
| 2004/0138748 A1 | 7/2004 | Boyer et al. |
| 2004/0143284 A1 | 7/2004 | Chin |
| 2004/0143332 A1 | 7/2004 | Krueger et al. |
| 2004/0143734 A1 | 7/2004 | Buer et al. |
| 2004/0147877 A1 | 7/2004 | Heuser |
| 2004/0147950 A1 | 7/2004 | Mueller et al. |
| 2004/0148027 A1 | 7/2004 | Errico et al. |
| 2004/0153064 A1 | 8/2004 | Foley et al. |
| 2004/0153065 A1 | 8/2004 | Lim |
| 2004/0153115 A1 | 8/2004 | Reiley et al. |
| 2004/0153156 A1 | 8/2004 | Cohen et al. |
| 2004/0153160 A1 | 8/2004 | Carrasco |
| 2004/0158206 A1 | 8/2004 | Aboul-Hosn et al. |
| 2004/0158258 A1 | 8/2004 | Bonati et al. |
| 2004/0162617 A1 | 8/2004 | Zucherman et al. |
| 2004/0162618 A1 | 8/2004 | Mujwid et al. |
| 2004/0167561 A1 | 8/2004 | Boucher et al. |
| 2004/0167562 A1 | 8/2004 | Osorio et al. |
| 2004/0167625 A1 | 8/2004 | Beyar et al. |
| 2004/0172133 A1 | 9/2004 | Gerber et al. |
| 2004/0172134 A1 | 9/2004 | Berry |
| 2004/0176775 A1 | 9/2004 | Burkus et al. |
| 2004/0186052 A1 | 9/2004 | Iyer et al. |
| 2004/0186471 A1 | 9/2004 | Trieu |
| 2004/0186482 A1 | 9/2004 | Kolb et al. |
| 2004/0186528 A1 | 9/2004 | Ries et al. |
| 2004/0186570 A1 | 9/2004 | Rapp |
| 2004/0186573 A1 | 9/2004 | Ferree |
| 2004/0186577 A1 | 9/2004 | Ferree |
| 2004/0193277 A1 | 9/2004 | Long et al. |
| 2004/0199162 A1 | 10/2004 | Von et al. |
| 2004/0210231 A1 | 10/2004 | Boucher et al. |
| 2004/0210310 A1 | 10/2004 | Trieu |
| 2004/0215343 A1 | 10/2004 | Hochschuler et al. |
| 2004/0215344 A1 | 10/2004 | Hochschuler et al. |
| 2004/0220580 A1 | 11/2004 | Johnson et al. |
| 2004/0220669 A1 | 11/2004 | Studer |
| 2004/0220672 A1 | 11/2004 | Shadduck |
| 2004/0225292 A1 | 11/2004 | Sasso et al. |
| 2004/0225296 A1 | 11/2004 | Reiss et al. |
| 2004/0225361 A1 | 11/2004 | Glenn et al. |
| 2004/0230191 A1 | 11/2004 | Frey et al. |
| 2004/0230309 A1 | 11/2004 | Dimauro et al. |
| 2004/0243229 A1 | 12/2004 | Vidlund et al. |
| 2004/0243239 A1 | 12/2004 | Taylor |
| 2004/0243241 A1 | 12/2004 | Istephanous et al. |
| 2004/0249377 A1 | 12/2004 | Kaes et al. |
| 2004/0249466 A1 | 12/2004 | Liu et al. |
| 2004/0254520 A1 | 12/2004 | Porteous et al. |
| 2004/0254575 A1 | 12/2004 | Obenchain et al. |
| 2004/0254644 A1 | 12/2004 | Taylor |
| 2004/0260297 A1 | 12/2004 | Padget et al. |
| 2004/0260300 A1 | 12/2004 | Gorensek et al. |
| 2004/0260397 A1 | 12/2004 | Lambrecht et al. |
| 2004/0266257 A1 | 12/2004 | Ries et al. |
| 2004/0267271 A9 | 12/2004 | Scribner et al. |
| 2004/0267367 A1 | 12/2004 | O'Neil |
| 2005/0004578 A1 | 1/2005 | Lambrecht et al. |
| 2005/0010293 A1 | 1/2005 | Zucherman et al. |
| 2005/0010298 A1 | 1/2005 | Zucherman et al. |
| 2005/0015148 A1 | 1/2005 | Jansen et al. |
| 2005/0015152 A1 | 1/2005 | Sweeney |
| 2005/0019365 A1 | 1/2005 | Frauchiger et al. |
| 2005/0021041 A1 | 1/2005 | Michelson |
| 2005/0033289 A1 | 2/2005 | Warren et al. |
| 2005/0033295 A1 | 2/2005 | Wisnewski |
| 2005/0033434 A1 | 2/2005 | Berry |
| 2005/0033440 A1 | 2/2005 | Lambrecht et al. |
| 2005/0038515 A1 | 2/2005 | Kunzler |
| 2005/0038517 A1 | 2/2005 | Carrison et al. |
| 2005/0043737 A1 | 2/2005 | Reiley et al. |
| 2005/0043796 A1 | 2/2005 | Grant et al. |
| 2005/0054948 A1 | 3/2005 | Goldenberg |
| 2005/0055097 A1 | 3/2005 | Grunberg et al. |
| 2005/0060036 A1 | 3/2005 | Schultz et al. |
| 2005/0060038 A1 | 3/2005 | Lambrecht et al. |
| 2005/0065519 A1 | 3/2005 | Michelson |
| 2005/0065609 A1 | 3/2005 | Wardlaw |
| 2005/0065610 A1 | 3/2005 | Pisharodi |
| 2005/0069571 A1 | 3/2005 | Slivka et al. |
| 2005/0070908 A1 | 3/2005 | Cragg |
| 2005/0070911 A1 | 3/2005 | Carrison et al. |
| 2005/0070913 A1 | 3/2005 | Milbocker et al. |
| 2005/0071011 A1 | 3/2005 | Ralph et al. |
| 2005/0080488 A1 | 4/2005 | Schultz |
| 2005/0085912 A1 | 4/2005 | Arnin et al. |
| 2005/0090443 A1 | 4/2005 | Michael John |
| 2005/0090833 A1 | 4/2005 | Dipoto |
| 2005/0090852 A1 | 4/2005 | Layne et al. |
| 2005/0090899 A1 | 4/2005 | Dipoto |
| 2005/0102202 A1 | 5/2005 | Linden et al. |
| 2005/0107880 A1 | 5/2005 | Shimp et al. |
| 2005/0113916 A1 | 5/2005 | Branch, Jr. |
| 2005/0113917 A1 | 5/2005 | Chae et al. |
| 2005/0113918 A1 | 5/2005 | Messerli et al. |
| 2005/0113919 A1 | 5/2005 | Cragg et al. |
| 2005/0113927 A1 | 5/2005 | Malek |
| 2005/0113928 A1 | 5/2005 | Cragg et al. |
| 2005/0118228 A1 | 6/2005 | Trieu |
| 2005/0118550 A1 | 6/2005 | Turri |

(56) References Cited

U.S. PATENT DOCUMENTS

| | | |
|---|---|---|
| 2005/0119657 A1 | 6/2005 | Goldsmith |
| 2005/0119662 A1 | 6/2005 | Reiley et al. |
| 2005/0119750 A1 | 6/2005 | Studer |
| 2005/0119751 A1 | 6/2005 | Lawson |
| 2005/0119752 A1 | 6/2005 | Williams et al. |
| 2005/0119754 A1 | 6/2005 | Trieu et al. |
| 2005/0124989 A1 | 6/2005 | Suddaby |
| 2005/0124992 A1 | 6/2005 | Ferree |
| 2005/0124999 A1 | 6/2005 | Teitelbaum et al. |
| 2005/0125062 A1 | 6/2005 | Biedermann et al. |
| 2005/0125066 A1 | 6/2005 | McAfee |
| 2005/0130929 A1 | 6/2005 | Boyd |
| 2005/0131267 A1 | 6/2005 | Talmadge |
| 2005/0131268 A1 | 6/2005 | Talmadge |
| 2005/0131269 A1 | 6/2005 | Talmadge |
| 2005/0131406 A1 | 6/2005 | Reiley et al. |
| 2005/0131409 A1 | 6/2005 | Chervitz et al. |
| 2005/0131411 A1 | 6/2005 | Culbert |
| 2005/0131536 A1 | 6/2005 | Eisermann et al. |
| 2005/0131538 A1 | 6/2005 | Chervitz et al. |
| 2005/0131540 A1 | 6/2005 | Trieu |
| 2005/0131541 A1 | 6/2005 | Trieu |
| 2005/0137595 A1 | 6/2005 | Hoffmann et al. |
| 2005/0137602 A1 | 6/2005 | Assell et al. |
| 2005/0142211 A1 | 6/2005 | Wenz |
| 2005/0143734 A1 | 6/2005 | Cachia et al. |
| 2005/0143763 A1 | 6/2005 | Ortiz et al. |
| 2005/0143827 A1 | 6/2005 | Globerman et al. |
| 2005/0149022 A1 | 7/2005 | Shaolian et al. |
| 2005/0149030 A1 | 7/2005 | Serhan et al. |
| 2005/0149191 A1 | 7/2005 | Cragg et al. |
| 2005/0149194 A1 | 7/2005 | Ahlgren |
| 2005/0149197 A1 | 7/2005 | Cauthen |
| 2005/0154396 A1 | 7/2005 | Foley et al. |
| 2005/0154463 A1 | 7/2005 | Trieu |
| 2005/0154467 A1 | 7/2005 | Peterman et al. |
| 2005/0165398 A1 | 7/2005 | Reiley |
| 2005/0165406 A1 | 7/2005 | Assell et al. |
| 2005/0165485 A1 | 7/2005 | Trieu |
| 2005/0171539 A1 | 8/2005 | Braun et al. |
| 2005/0171552 A1 | 8/2005 | Johnson et al. |
| 2005/0171608 A1 | 8/2005 | Peterman et al. |
| 2005/0171610 A1 | 8/2005 | Humphreys et al. |
| 2005/0177235 A1 | 8/2005 | Baynham et al. |
| 2005/0177240 A1 | 8/2005 | Blain |
| 2005/0182412 A1 | 8/2005 | Johnson et al. |
| 2005/0182413 A1 | 8/2005 | Johnson et al. |
| 2005/0182414 A1 | 8/2005 | Manzi et al. |
| 2005/0182418 A1 | 8/2005 | Boyd et al. |
| 2005/0187556 A1 | 8/2005 | Stack et al. |
| 2005/0187558 A1 | 8/2005 | Johnson et al. |
| 2005/0187559 A1 | 8/2005 | Raymond et al. |
| 2005/0187564 A1 | 8/2005 | Jayaraman |
| 2005/0197702 A1 | 9/2005 | Coppes et al. |
| 2005/0197707 A1 | 9/2005 | Trieu et al. |
| 2005/0203512 A1 | 9/2005 | Hawkins et al. |
| 2005/0216018 A1 | 9/2005 | Sennett |
| 2005/0216026 A1 | 9/2005 | Culbert |
| 2005/0216087 A1 | 9/2005 | Zucherman et al. |
| 2005/0222681 A1 | 10/2005 | Richley et al. |
| 2005/0222684 A1 | 10/2005 | Ferree |
| 2005/0228383 A1 | 10/2005 | Zucherman et al. |
| 2005/0228391 A1 | 10/2005 | Levy et al. |
| 2005/0228397 A1 | 10/2005 | Malandain et al. |
| 2005/0234425 A1 | 10/2005 | Miller et al. |
| 2005/0234451 A1 | 10/2005 | Markworth |
| 2005/0234452 A1 | 10/2005 | Malandain |
| 2005/0234456 A1 | 10/2005 | Malandain |
| 2005/0240182 A1 | 10/2005 | Zucherman et al. |
| 2005/0240189 A1 | 10/2005 | Rousseau et al. |
| 2005/0240193 A1 | 10/2005 | Layne et al. |
| 2005/0240269 A1 | 10/2005 | Lambrecht et al. |
| 2005/0251142 A1 | 11/2005 | Hoffmann et al. |
| 2005/0251149 A1 | 11/2005 | Wenz |
| 2005/0251260 A1 | 11/2005 | Gerber et al. |
| 2005/0256525 A1 | 11/2005 | Culbert et al. |
| 2005/0256576 A1 | 11/2005 | Moskowitz et al. |
| 2005/0261682 A1 | 11/2005 | Ferree |
| 2005/0261684 A1 | 11/2005 | Shaolian et al. |
| 2005/0261695 A1 | 11/2005 | Cragg et al. |
| 2005/0261769 A1 | 11/2005 | Moskowitz et al. |
| 2005/0261781 A1 | 11/2005 | Sennett et al. |
| 2005/0267471 A1 | 12/2005 | Biedermann et al. |
| 2005/0273166 A1 | 12/2005 | Sweeney |
| 2005/0273173 A1 | 12/2005 | Gordon et al. |
| 2005/0278023 A1 | 12/2005 | Zwirkoski |
| 2005/0278026 A1 | 12/2005 | Gordon et al. |
| 2005/0278027 A1 | 12/2005 | Hyde, Jr. |
| 2005/0278029 A1 | 12/2005 | Trieu |
| 2005/0283238 A1 | 12/2005 | Reiley |
| 2005/0283244 A1 | 12/2005 | Gordon et al. |
| 2005/0287071 A1 | 12/2005 | Wenz |
| 2006/0004326 A1 | 1/2006 | Collins et al. |
| 2006/0004456 A1 | 1/2006 | McKay |
| 2006/0004457 A1 | 1/2006 | Collins et al. |
| 2006/0004458 A1 | 1/2006 | Collins et al. |
| 2006/0009778 A1 | 1/2006 | Collins et al. |
| 2006/0009779 A1 | 1/2006 | Collins et al. |
| 2006/0009851 A1 | 1/2006 | Collins et al. |
| 2006/0015105 A1 | 1/2006 | Warren et al. |
| 2006/0015119 A1 | 1/2006 | Plassky et al. |
| 2006/0020284 A1 | 1/2006 | Foley et al. |
| 2006/0030850 A1 | 2/2006 | Keegan et al. |
| 2006/0030872 A1 | 2/2006 | Culbert et al. |
| 2006/0030933 A1 | 2/2006 | Delegge et al. |
| 2006/0030943 A1 | 2/2006 | Peterman |
| 2006/0036241 A1 | 2/2006 | Siegal |
| 2006/0036246 A1 | 2/2006 | Carl et al. |
| 2006/0036256 A1 | 2/2006 | Carl et al. |
| 2006/0036259 A1 | 2/2006 | Carl et al. |
| 2006/0036261 A1 | 2/2006 | McDonnell |
| 2006/0036273 A1 | 2/2006 | Siegal |
| 2006/0036323 A1 | 2/2006 | Carl et al. |
| 2006/0036324 A1 | 2/2006 | Sachs et al. |
| 2006/0041258 A1 | 2/2006 | Galea |
| 2006/0041314 A1 | 2/2006 | Millard |
| 2006/0045904 A1 | 3/2006 | Aronson |
| 2006/0058790 A1 | 3/2006 | Carl et al. |
| 2006/0058807 A1 | 3/2006 | Landry et al. |
| 2006/0058876 A1 | 3/2006 | McKinley |
| 2006/0058880 A1 | 3/2006 | Wysocki et al. |
| 2006/0064171 A1 | 3/2006 | Trieu |
| 2006/0064172 A1 | 3/2006 | Trieu |
| 2006/0069439 A1 | 3/2006 | Zucherman et al. |
| 2006/0069440 A1 | 3/2006 | Zucherman et al. |
| 2006/0079908 A1 | 4/2006 | Lieberman |
| 2006/0084867 A1 | 4/2006 | Tremblay et al. |
| 2006/0084977 A1 | 4/2006 | Lieberman |
| 2006/0084988 A1 | 4/2006 | Kim |
| 2006/0085002 A1 | 4/2006 | Trieu et al. |
| 2006/0085009 A1 | 4/2006 | Truckai et al. |
| 2006/0085010 A1 | 4/2006 | Lieberman |
| 2006/0089642 A1 | 4/2006 | Diaz et al. |
| 2006/0089646 A1 | 4/2006 | Bonutti |
| 2006/0089654 A1 | 4/2006 | Lins et al. |
| 2006/0089715 A1 | 4/2006 | Truckai et al. |
| 2006/0089718 A1 | 4/2006 | Zucherman et al. |
| 2006/0089719 A1 | 4/2006 | Trieu |
| 2006/0095045 A1 | 5/2006 | Trieu |
| 2006/0095046 A1 | 5/2006 | Trieu et al. |
| 2006/0095134 A1 | 5/2006 | Trieu et al. |
| 2006/0095138 A1 | 5/2006 | Truckai et al. |
| 2006/0100706 A1 | 5/2006 | Shadduck et al. |
| 2006/0100707 A1 | 5/2006 | Stinson et al. |
| 2006/0106381 A1 | 5/2006 | Ferree et al. |
| 2006/0106397 A1 | 5/2006 | Lins |
| 2006/0106459 A1 | 5/2006 | Truckai et al. |
| 2006/0111785 A1 | 5/2006 | O'Neil |
| 2006/0119629 A1 | 6/2006 | An et al. |
| 2006/0122609 A1 | 6/2006 | Mirkovic et al. |
| 2006/0122610 A1 | 6/2006 | Culbert et al. |
| 2006/0122701 A1 | 6/2006 | Kiester |
| 2006/0122703 A1 | 6/2006 | Aebi et al. |
| 2006/0122704 A1 | 6/2006 | Vresilovic et al. |

(56) References Cited

U.S. PATENT DOCUMENTS

| | | |
|---|---|---|
| 2006/0129244 A1 | 6/2006 | Ensign |
| 2006/0136062 A1 | 6/2006 | Dinello et al. |
| 2006/0136064 A1 | 6/2006 | Sherman |
| 2006/0142759 A1 | 6/2006 | Arnin et al. |
| 2006/0142765 A9 | 6/2006 | Dixon et al. |
| 2006/0142776 A1 | 6/2006 | Iwanari |
| 2006/0142858 A1 | 6/2006 | Colleran et al. |
| 2006/0142864 A1 | 6/2006 | Cauthen |
| 2006/0149136 A1 | 7/2006 | Seto et al. |
| 2006/0149237 A1 | 7/2006 | Markworth et al. |
| 2006/0149252 A1 | 7/2006 | Markworth et al. |
| 2006/0149379 A1 | 7/2006 | Kuslich et al. |
| 2006/0149380 A1 | 7/2006 | Lotz et al. |
| 2006/0155379 A1 | 7/2006 | Heneveld et al. |
| 2006/0161162 A1 | 7/2006 | Lambrecht et al. |
| 2006/0161166 A1 | 7/2006 | Johnson et al. |
| 2006/0167553 A1 | 7/2006 | Cauthen et al. |
| 2006/0173545 A1 | 8/2006 | Cauthen et al. |
| 2006/0178743 A1 | 8/2006 | Carter |
| 2006/0178746 A1 | 8/2006 | Bartish et al. |
| 2006/0184192 A1 | 8/2006 | Markworth et al. |
| 2006/0184247 A1 | 8/2006 | Edidin et al. |
| 2006/0184248 A1 | 8/2006 | Edidin et al. |
| 2006/0189999 A1 | 8/2006 | Zwirkoski |
| 2006/0190083 A1 | 8/2006 | Arnin et al. |
| 2006/0190085 A1 | 8/2006 | Cauthen |
| 2006/0195102 A1 | 8/2006 | Malandain |
| 2006/0195103 A1 | 8/2006 | Padget et al. |
| 2006/0195191 A1 | 8/2006 | Sweeney et al. |
| 2006/0200139 A1 | 9/2006 | Michelson |
| 2006/0200164 A1 | 9/2006 | Michelson |
| 2006/0200239 A1 | 9/2006 | Rothman et al. |
| 2006/0200240 A1 | 9/2006 | Rothman et al. |
| 2006/0200241 A1 | 9/2006 | Rothman et al. |
| 2006/0200242 A1 | 9/2006 | Rothman et al. |
| 2006/0200243 A1 | 9/2006 | Rothman et al. |
| 2006/0206116 A1 | 9/2006 | Yeung |
| 2006/0206207 A1 | 9/2006 | Dryer et al. |
| 2006/0217711 A1 | 9/2006 | Stevens et al. |
| 2006/0229629 A1 | 10/2006 | Manzi et al. |
| 2006/0235403 A1 | 10/2006 | Blain |
| 2006/0235412 A1 | 10/2006 | Blain |
| 2006/0235423 A1 | 10/2006 | Cantu |
| 2006/0235521 A1 | 10/2006 | Zucherman et al. |
| 2006/0235531 A1 | 10/2006 | Buettner-Janz |
| 2006/0241663 A1 | 10/2006 | Rice et al. |
| 2006/0241770 A1 | 10/2006 | Rhoda et al. |
| 2006/0247634 A1 | 11/2006 | Warner et al. |
| 2006/0247770 A1 | 11/2006 | Peterman |
| 2006/0247771 A1 | 11/2006 | Peterman et al. |
| 2006/0247781 A1 | 11/2006 | Francis |
| 2006/0253201 A1 | 11/2006 | McLuen |
| 2006/0264896 A1 | 11/2006 | Palmer |
| 2006/0264939 A1 | 11/2006 | Zucherman et al. |
| 2006/0264945 A1 | 11/2006 | Edidin et al. |
| 2006/0265067 A1 | 11/2006 | Zucherman et al. |
| 2006/0265075 A1 | 11/2006 | Baumgartner et al. |
| 2006/0265077 A1 | 11/2006 | Zwirkoski |
| 2006/0271049 A1 | 11/2006 | Zucherman et al. |
| 2006/0271061 A1 | 11/2006 | Beyar et al. |
| 2006/0276897 A1 | 12/2006 | Winslow et al. |
| 2006/0276899 A1 | 12/2006 | Zipnick et al. |
| 2006/0276901 A1 | 12/2006 | Zipnick et al. |
| 2006/0276902 A1 | 12/2006 | Zipnick et al. |
| 2006/0282167 A1 | 12/2006 | Lambrecht et al. |
| 2006/0287726 A1 | 12/2006 | Segal et al. |
| 2006/0287727 A1 | 12/2006 | Segal et al. |
| 2006/0293662 A1 | 12/2006 | Boyer et al. |
| 2006/0293663 A1 | 12/2006 | Walkenhorst et al. |
| 2006/0293753 A1 | 12/2006 | Thramann |
| 2007/0006692 A1 | 1/2007 | Phan |
| 2007/0010716 A1 | 1/2007 | Malandain et al. |
| 2007/0010717 A1 | 1/2007 | Cragg |
| 2007/0010824 A1 | 1/2007 | Malandain et al. |
| 2007/0010826 A1 | 1/2007 | Rhoda et al. |
| 2007/0010844 A1 | 1/2007 | Gong et al. |
| 2007/0010845 A1 | 1/2007 | Gong et al. |
| 2007/0010846 A1 | 1/2007 | Leung et al. |
| 2007/0010848 A1 | 1/2007 | Leung et al. |
| 2007/0010886 A1 | 1/2007 | Banick et al. |
| 2007/0010889 A1 | 1/2007 | Francis |
| 2007/0016191 A1 | 1/2007 | Culbert et al. |
| 2007/0032703 A1 | 2/2007 | Sankaran et al. |
| 2007/0032790 A1 | 2/2007 | Aschmann et al. |
| 2007/0032791 A1 | 2/2007 | Greenhalgh |
| 2007/0043361 A1 | 2/2007 | Malandain et al. |
| 2007/0043362 A1 | 2/2007 | Malandain et al. |
| 2007/0043363 A1 | 2/2007 | Malandain et al. |
| 2007/0043440 A1 | 2/2007 | William et al. |
| 2007/0048382 A1 | 3/2007 | Meyer et al. |
| 2007/0049849 A1 | 3/2007 | Schwardt et al. |
| 2007/0049934 A1 | 3/2007 | Edidin et al. |
| 2007/0049935 A1 | 3/2007 | Edidin et al. |
| 2007/0050034 A1 | 3/2007 | Schwardt et al. |
| 2007/0050035 A1 | 3/2007 | Schwardt et al. |
| 2007/0055201 A1 | 3/2007 | Seto et al. |
| 2007/0055236 A1 | 3/2007 | Hudgins et al. |
| 2007/0055237 A1 | 3/2007 | Edidin et al. |
| 2007/0055246 A1 | 3/2007 | Zucherman et al. |
| 2007/0055265 A1 | 3/2007 | Schaller |
| 2007/0055266 A1 | 3/2007 | Osorio et al. |
| 2007/0055267 A1 | 3/2007 | Osorio et al. |
| 2007/0055271 A1 | 3/2007 | Schaller |
| 2007/0055272 A1 | 3/2007 | Schaller |
| 2007/0055273 A1 | 3/2007 | Schaller |
| 2007/0055274 A1 | 3/2007 | Appenzeller et al. |
| 2007/0055275 A1 | 3/2007 | Schaller |
| 2007/0055276 A1 | 3/2007 | Edidin |
| 2007/0055277 A1 | 3/2007 | Osorio et al. |
| 2007/0055278 A1 | 3/2007 | Osorio et al. |
| 2007/0055281 A1 | 3/2007 | Osorio et al. |
| 2007/0055284 A1 | 3/2007 | Osorio et al. |
| 2007/0055300 A1 | 3/2007 | Osorio et al. |
| 2007/0055377 A1 | 3/2007 | Hanson et al. |
| 2007/0060933 A1 | 3/2007 | Sankaran et al. |
| 2007/0060935 A1 | 3/2007 | Schwardt et al. |
| 2007/0067034 A1 | 3/2007 | Chirico et al. |
| 2007/0067035 A1 | 3/2007 | Falahee |
| 2007/0068329 A1 | 3/2007 | Phan et al. |
| 2007/0073292 A1 | 3/2007 | Kohm et al. |
| 2007/0073399 A1 | 3/2007 | Zipnick et al. |
| 2007/0078436 A1 | 4/2007 | Leung et al. |
| 2007/0078463 A1 | 4/2007 | Malandain |
| 2007/0093689 A1 | 4/2007 | Steinberg |
| 2007/0093899 A1 | 4/2007 | Dutoit et al. |
| 2007/0093906 A1 | 4/2007 | Hudgins et al. |
| 2007/0118132 A1 | 5/2007 | Culbert et al. |
| 2007/0118222 A1 | 5/2007 | Lang |
| 2007/0118223 A1 | 5/2007 | Allard et al. |
| 2007/0123868 A1 | 5/2007 | Culbert et al. |
| 2007/0123891 A1 | 5/2007 | Ries et al. |
| 2007/0123892 A1 | 5/2007 | Ries et al. |
| 2007/0123986 A1 | 5/2007 | Schaller |
| 2007/0129730 A1 | 6/2007 | Woods et al. |
| 2007/0135922 A1 | 6/2007 | Trieu |
| 2007/0149978 A1 | 6/2007 | Sheziti et al. |
| 2007/0150059 A1 | 6/2007 | Ruberte et al. |
| 2007/0150060 A1 | 6/2007 | Trieu |
| 2007/0150061 A1 | 6/2007 | Trieu |
| 2007/0150063 A1 | 6/2007 | Ruberte et al. |
| 2007/0150064 A1 | 6/2007 | Ruberte et al. |
| 2007/0162005 A1 | 7/2007 | Peterson et al. |
| 2007/0162127 A1 | 7/2007 | Peterman et al. |
| 2007/0162138 A1 | 7/2007 | Heinz |
| 2007/0167945 A1 | 7/2007 | Lange et al. |
| 2007/0168036 A1 | 7/2007 | Ainsworth et al. |
| 2007/0168038 A1 | 7/2007 | Trieu |
| 2007/0173939 A1 | 7/2007 | Kim et al. |
| 2007/0173940 A1 | 7/2007 | Hestad et al. |
| 2007/0178222 A1 | 8/2007 | Storey et al. |
| 2007/0179612 A1 | 8/2007 | Johnson et al. |
| 2007/0179615 A1 | 8/2007 | Heinz et al. |
| 2007/0179616 A1 | 8/2007 | Braddock et al. |
| 2007/0179618 A1 | 8/2007 | Trieu et al. |

(56) References Cited

U.S. PATENT DOCUMENTS

| | | |
|---|---|---|
| 2007/0185578 A1 | 8/2007 | O'Neil et al. |
| 2007/0191953 A1 | 8/2007 | Trieu |
| 2007/0191954 A1 | 8/2007 | Hansell et al. |
| 2007/0191959 A1 | 8/2007 | Hartmann et al. |
| 2007/0197935 A1 | 8/2007 | Reiley et al. |
| 2007/0198023 A1 | 8/2007 | Sand et al. |
| 2007/0198025 A1 | 8/2007 | Trieu et al. |
| 2007/0198089 A1 | 8/2007 | Moskowitz et al. |
| 2007/0203491 A1 | 8/2007 | Pasquet et al. |
| 2007/0208423 A1 | 9/2007 | Messerli et al. |
| 2007/0208426 A1 | 9/2007 | Trieu |
| 2007/0213717 A1 | 9/2007 | Trieu et al. |
| 2007/0219634 A1 | 9/2007 | Greenhalgh et al. |
| 2007/0233074 A1 | 10/2007 | Anderson et al. |
| 2007/0233083 A1 | 10/2007 | Abdou |
| 2007/0233089 A1 | 10/2007 | Dipoto et al. |
| 2007/0233244 A1 | 10/2007 | Lopez et al. |
| 2007/0260255 A1 | 11/2007 | Haddock et al. |
| 2007/0270954 A1 | 11/2007 | Wu |
| 2007/0270957 A1 | 11/2007 | Heinz |
| 2007/0270968 A1 | 11/2007 | Baynham et al. |
| 2007/0276375 A1 | 11/2007 | Rapp |
| 2007/0282443 A1 | 12/2007 | Globerman et al. |
| 2007/0282449 A1 | 12/2007 | De et al. |
| 2007/0299521 A1 | 12/2007 | Glenn et al. |
| 2008/0009877 A1 | 1/2008 | Sankaran et al. |
| 2008/0015701 A1 | 1/2008 | Garcia et al. |
| 2008/0021556 A1 | 1/2008 | Edie |
| 2008/0021557 A1 | 1/2008 | Trieu |
| 2008/0021558 A1 | 1/2008 | Thramann |
| 2008/0027437 A1 | 1/2008 | Johnson et al. |
| 2008/0027453 A1 | 1/2008 | Johnson et al. |
| 2008/0027454 A1 | 1/2008 | Johnson et al. |
| 2008/0027550 A1 | 1/2008 | Link et al. |
| 2008/0033440 A1 | 2/2008 | Moskowitz et al. |
| 2008/0051897 A1 | 2/2008 | Lopez et al. |
| 2008/0051902 A1 | 2/2008 | Dwyer |
| 2008/0058598 A1 | 3/2008 | Ries et al. |
| 2008/0058944 A1 | 3/2008 | Duplessis et al. |
| 2008/0065219 A1 | 3/2008 | Dye |
| 2008/0071356 A1 | 3/2008 | Greenhalgh et al. |
| 2008/0077148 A1 | 3/2008 | Ries et al. |
| 2008/0082172 A1 | 4/2008 | Jackson |
| 2008/0082173 A1 | 4/2008 | Delurio et al. |
| 2008/0097436 A1 | 4/2008 | Culbert et al. |
| 2008/0097611 A1 | 4/2008 | Mastrorio et al. |
| 2008/0103601 A1 | 5/2008 | Biro et al. |
| 2008/0108996 A1 | 5/2008 | Padget et al. |
| 2008/0125865 A1 | 5/2008 | Abdelgany |
| 2008/0132934 A1 | 6/2008 | Reiley et al. |
| 2008/0133017 A1 | 6/2008 | Beyar et al. |
| 2008/0140085 A1 | 6/2008 | Gately et al. |
| 2008/0140207 A1 | 6/2008 | Olmos et al. |
| 2008/0147193 A1 | 6/2008 | Matthis et al. |
| 2008/0161927 A1 | 7/2008 | Savage et al. |
| 2008/0167657 A1 | 7/2008 | Greenhalgh |
| 2008/0177306 A1 | 7/2008 | Lamborne et al. |
| 2008/0177388 A1 | 7/2008 | Patterson et al. |
| 2008/0183204 A1 | 7/2008 | Greenhalgh et al. |
| 2008/0188945 A1 | 8/2008 | Boyce et al. |
| 2008/0195096 A1 | 8/2008 | Frei |
| 2008/0195209 A1 | 8/2008 | Garcia et al. |
| 2008/0195210 A1 | 8/2008 | Milijasevic et al. |
| 2008/0208255 A1 | 8/2008 | Siegal |
| 2008/0221687 A1 | 9/2008 | Viker |
| 2008/0228225 A1 | 9/2008 | Trautwein et al. |
| 2008/0229597 A1 | 9/2008 | Malandain |
| 2008/0243251 A1 | 10/2008 | Stad et al. |
| 2008/0243254 A1 | 10/2008 | Butler |
| 2008/0249622 A1 | 10/2008 | Gray |
| 2008/0255618 A1 | 10/2008 | Fisher et al. |
| 2008/0262619 A1 | 10/2008 | Ray |
| 2008/0269904 A1 | 10/2008 | Voorhies |
| 2008/0281346 A1 | 11/2008 | Greenhalgh et al. |
| 2008/0281364 A1 | 11/2008 | Chirico et al. |
| 2008/0281425 A1 | 11/2008 | Thalgott et al. |
| 2008/0287981 A1 | 11/2008 | Culbert et al. |
| 2008/0287997 A1 | 11/2008 | Altarac et al. |
| 2008/0300685 A1 | 12/2008 | Carls et al. |
| 2008/0306537 A1 | 12/2008 | Culbert |
| 2008/0319477 A1* | 12/2008 | Justis .................. A61B 17/7089 606/232 |
| 2009/0005870 A1 | 1/2009 | Hawkins et al. |
| 2009/0005873 A1 | 1/2009 | Slivka et al. |
| 2009/0018524 A1 | 1/2009 | Greenhalgh et al. |
| 2009/0030423 A1 | 1/2009 | Puno |
| 2009/0048631 A1 | 2/2009 | Bhatnagar et al. |
| 2009/0048678 A1 | 2/2009 | Saal et al. |
| 2009/0054991 A1 | 2/2009 | Biyani et al. |
| 2009/0069813 A1 | 3/2009 | Von et al. |
| 2009/0069895 A1 | 3/2009 | Gittings et al. |
| 2009/0074538 A1 | 3/2009 | Richie |
| 2009/0076610 A1 | 3/2009 | Afzal |
| 2009/0099568 A1 | 4/2009 | Lowry et al. |
| 2009/0105712 A1 | 4/2009 | Dauster et al. |
| 2009/0105745 A1 | 4/2009 | Culbert |
| 2009/0112320 A1 | 4/2009 | Kraus |
| 2009/0112324 A1 | 4/2009 | Refai et al. |
| 2009/0131986 A1 | 5/2009 | Lee et al. |
| 2009/0149857 A1 | 6/2009 | Culbert et al. |
| 2009/0164020 A1 | 6/2009 | Janowski et al. |
| 2009/0177281 A1 | 7/2009 | Swanson et al. |
| 2009/0177284 A1 | 7/2009 | Rogers et al. |
| 2009/0182429 A1 | 7/2009 | Humphreys et al. |
| 2009/0192614 A1 | 7/2009 | Beger et al. |
| 2009/0222096 A1 | 9/2009 | Trieu |
| 2009/0222099 A1 | 9/2009 | Liu et al. |
| 2009/0222100 A1 | 9/2009 | Cipoletti et al. |
| 2009/0234398 A1 | 9/2009 | Chirico et al. |
| 2009/0240334 A1 | 9/2009 | Richelsoph |
| 2009/0240335 A1 | 9/2009 | Arcenio et al. |
| 2009/0248159 A1 | 10/2009 | Aflatoon |
| 2009/0248163 A1 | 10/2009 | King et al. |
| 2009/0275890 A1 | 11/2009 | Leibowitz et al. |
| 2009/0276051 A1 | 11/2009 | Arramon et al. |
| 2009/0281580 A1 | 11/2009 | Emannuel |
| 2009/0292361 A1 | 11/2009 | Lopez |
| 2010/0016905 A1 | 1/2010 | Greenhalgh et al. |
| 2010/0040332 A1 | 2/2010 | Van et al. |
| 2010/0042218 A1 | 2/2010 | Nebosky et al. |
| 2010/0076492 A1 | 3/2010 | Warner et al. |
| 2010/0076559 A1 | 3/2010 | Bagga et al. |
| 2010/0082109 A1 | 4/2010 | Greenhalgh et al. |
| 2010/0094424 A1 | 4/2010 | Woodburn et al. |
| 2010/0094426 A1 | 4/2010 | Grohowski et al. |
| 2010/0114105 A1 | 5/2010 | Butters et al. |
| 2010/0114147 A1 | 5/2010 | Biyani |
| 2010/0174314 A1 | 7/2010 | Mirkovic et al. |
| 2010/0179594 A1 | 7/2010 | Theofilos et al. |
| 2010/0191336 A1 | 7/2010 | Greenhalgh |
| 2010/0204795 A1 | 8/2010 | Greenhalgh |
| 2010/0211176 A1 | 8/2010 | Greenhalgh |
| 2010/0211182 A1 | 8/2010 | Zimmermann |
| 2010/0234956 A1 | 9/2010 | Attia et al. |
| 2010/0262240 A1 | 10/2010 | Chavatte et al. |
| 2010/0268231 A1 | 10/2010 | Kuslich et al. |
| 2010/0268338 A1 | 10/2010 | Melkent et al. |
| 2010/0286783 A1 | 11/2010 | Lechmann et al. |
| 2010/0292700 A1 | 11/2010 | Ries |
| 2010/0298938 A1 | 11/2010 | Humphreys et al. |
| 2010/0324607 A1 | 12/2010 | Davis |
| 2010/0331891 A1 | 12/2010 | Culbert et al. |
| 2011/0004308 A1 | 1/2011 | Marino et al. |
| 2011/0004310 A1 | 1/2011 | Michelson |
| 2011/0015747 A1 | 1/2011 | McManus et al. |
| 2011/0029082 A1 | 2/2011 | Hall |
| 2011/0035011 A1 | 2/2011 | Cain |
| 2011/0054538 A1 | 3/2011 | Zehavi et al. |
| 2011/0071527 A1 | 3/2011 | Nelson et al. |
| 2011/0082552 A1 | 4/2011 | Wistrom et al. |
| 2011/0093074 A1 | 4/2011 | Glerum et al. |
| 2011/0093076 A1 | 4/2011 | Reo et al. |
| 2011/0098531 A1 | 4/2011 | To |
| 2011/0098628 A1 | 4/2011 | Yeung et al. |

(56) References Cited

U.S. PATENT DOCUMENTS

| | | |
|---|---|---|
| 2011/0098818 A1 | 4/2011 | Brodke et al. |
| 2011/0130835 A1 | 6/2011 | Ashley et al. |
| 2011/0130838 A1 | 6/2011 | Morgenstern Lopez |
| 2011/0144692 A1 | 6/2011 | Saladin et al. |
| 2011/0144753 A1 | 6/2011 | Marchek et al. |
| 2011/0153020 A1 | 6/2011 | Abdelgany et al. |
| 2011/0159070 A1 | 6/2011 | Jin et al. |
| 2011/0160866 A1 | 6/2011 | Laurence et al. |
| 2011/0172716 A1 | 7/2011 | Glerum |
| 2011/0172774 A1 | 7/2011 | Varela |
| 2011/0238072 A1 | 9/2011 | Tyndall |
| 2011/0270261 A1 | 11/2011 | Mast et al. |
| 2011/0270401 A1 | 11/2011 | McKay |
| 2011/0282453 A1 | 11/2011 | Greenhalgh et al. |
| 2011/0301711 A1 | 12/2011 | Palmatier et al. |
| 2011/0301712 A1 | 12/2011 | Palmatier et al. |
| 2011/0307010 A1 | 12/2011 | Pradhan |
| 2011/0313465 A1 | 12/2011 | Warren et al. |
| 2011/0320000 A1 | 12/2011 | O'Neil |
| 2012/0004726 A1 | 1/2012 | Greenhalgh et al. |
| 2012/0004732 A1 | 1/2012 | Goel et al. |
| 2012/0022654 A1 | 1/2012 | Farris et al. |
| 2012/0023994 A1 | 2/2012 | Powell |
| 2012/0029636 A1 | 2/2012 | Ragab et al. |
| 2012/0059474 A1 | 3/2012 | Weiman |
| 2012/0059475 A1 | 3/2012 | Weiman |
| 2012/0071977 A1 | 3/2012 | Oglaza et al. |
| 2012/0071980 A1 | 3/2012 | Purcell et al. |
| 2012/0083887 A1 | 4/2012 | Purcell et al. |
| 2012/0083889 A1 | 4/2012 | Purcell et al. |
| 2012/0123546 A1 | 5/2012 | Medina |
| 2012/0136443 A1 | 5/2012 | Wenzel |
| 2012/0150304 A1 | 6/2012 | Glerum et al. |
| 2012/0150305 A1 | 6/2012 | Glerum et al. |
| 2012/0158146 A1 | 6/2012 | Glerum et al. |
| 2012/0158147 A1 | 6/2012 | Glerum et al. |
| 2012/0158148 A1 | 6/2012 | Glerum et al. |
| 2012/0185049 A1 | 7/2012 | Varela |
| 2012/0197299 A1* | 8/2012 | Fabian, Jr. ............ A61F 2/4455 606/279 |
| 2012/0197403 A1 | 8/2012 | Merves |
| 2012/0197405 A1 | 8/2012 | Cuevas et al. |
| 2012/0203290 A1 | 8/2012 | Warren et al. |
| 2012/0203347 A1 | 8/2012 | Glerum et al. |
| 2012/0215262 A1 | 8/2012 | Culbert et al. |
| 2012/0215316 A1 | 8/2012 | Mohr et al. |
| 2012/0226357 A1 | 9/2012 | Varela |
| 2012/0232552 A1 | 9/2012 | Morgenstern et al. |
| 2012/0232658 A1 | 9/2012 | Morgenstern et al. |
| 2012/0265309 A1 | 10/2012 | Glerum et al. |
| 2012/0277795 A1 | 11/2012 | Von et al. |
| 2012/0277869 A1 | 11/2012 | Siccardi et al. |
| 2012/0290090 A1 | 11/2012 | Glerum et al. |
| 2012/0290097 A1 | 11/2012 | Cipoletti et al. |
| 2012/0310350 A1 | 12/2012 | Farris et al. |
| 2012/0310352 A1 | 12/2012 | Dimauro et al. |
| 2012/0323327 A1* | 12/2012 | McAfee ............ A61F 2/447 623/17.16 |
| 2012/0323328 A1 | 12/2012 | Weiman |
| 2012/0330421 A1 | 12/2012 | Weiman |
| 2012/0330422 A1 | 12/2012 | Weiman |
| 2013/0006361 A1 | 1/2013 | Glerum et al. |
| 2013/0023993 A1 | 1/2013 | Weiman |
| 2013/0023994 A1 | 1/2013 | Glerum |
| 2013/0030536 A1 | 1/2013 | Rhoda et al. |
| 2013/0030544 A1 | 1/2013 | Studer |
| 2013/0060337 A1 | 3/2013 | Petersheim et al. |
| 2013/0073044 A1 | 3/2013 | Gamache |
| 2013/0085572 A1 | 4/2013 | Glerum et al. |
| 2013/0085574 A1 | 4/2013 | Sledge |
| 2013/0110240 A1 | 5/2013 | Hansell et al. |
| 2013/0116791 A1 | 5/2013 | Theofilos |
| 2013/0123924 A1 | 5/2013 | Butler et al. |
| 2013/0123927 A1 | 5/2013 | Malandain |
| 2013/0138214 A1 | 5/2013 | Greenhalgh et al. |
| 2013/0144387 A1 | 6/2013 | Walker et al. |
| 2013/0144388 A1 | 6/2013 | Emery et al. |
| 2013/0144391 A1 | 6/2013 | Siegal et al. |
| 2013/0158663 A1 | 6/2013 | Miller et al. |
| 2013/0158664 A1 | 6/2013 | Palmatier et al. |
| 2013/0158667 A1 | 6/2013 | Tabor et al. |
| 2013/0158668 A1 | 6/2013 | Nichols et al. |
| 2013/0158669 A1 | 6/2013 | Sungarian et al. |
| 2013/0173004 A1 | 7/2013 | Greenhalgh et al. |
| 2013/0190875 A1 | 7/2013 | Shulock et al. |
| 2013/0190876 A1 | 7/2013 | Drochner et al. |
| 2013/0190877 A1 | 7/2013 | Medina |
| 2013/0204371 A1 | 8/2013 | McLuen et al. |
| 2013/0211525 A1 | 8/2013 | McLuen et al. |
| 2013/0211526 A1 | 8/2013 | Alheidt et al. |
| 2013/0218276 A1 | 8/2013 | Fiechter et al. |
| 2013/0253585 A1 | 9/2013 | Garcia et al. |
| 2013/0261746 A1 | 10/2013 | Linares et al. |
| 2013/0310939 A1 | 11/2013 | Fabian et al. |
| 2013/0325128 A1* | 12/2013 | Perloff ............ A61F 2/4455 623/17.16 |
| 2014/0018816 A1* | 1/2014 | Fenn ............ A61B 17/162 606/104 |
| 2014/0025169 A1 | 1/2014 | Lechmann et al. |
| 2014/0039622 A1 | 2/2014 | Glerum et al. |
| 2014/0046333 A1 | 2/2014 | Johnson et al. |
| 2014/0046446 A1 | 2/2014 | Robinson |
| 2014/0058513 A1 | 2/2014 | Gahman et al. |
| 2014/0067073 A1 | 3/2014 | Hauck |
| 2014/0086962 A1 | 3/2014 | Jin et al. |
| 2014/0094916 A1 | 4/2014 | Glerum et al. |
| 2014/0100662 A1 | 4/2014 | Patterson |
| 2014/0107790 A1 | 4/2014 | Combrowski |
| 2014/0114414 A1 | 4/2014 | Abdou et al. |
| 2014/0114423 A1 | 4/2014 | Suedkamp et al. |
| 2014/0128977 A1 | 5/2014 | Glerum et al. |
| 2014/0128980 A1 | 5/2014 | Kirschman |
| 2014/0135934 A1 | 5/2014 | Hansell et al. |
| 2014/0142706 A1 | 5/2014 | Hansell et al. |
| 2014/0163682 A1 | 6/2014 | Lott |
| 2014/0163683 A1 | 6/2014 | Seifert et al. |
| 2014/0172106 A1 | 6/2014 | To et al. |
| 2014/0180421 A1 | 6/2014 | Glerum et al. |
| 2014/0188225 A1 | 7/2014 | Dmuschewsky |
| 2014/0228959 A1 | 8/2014 | Niemiec et al. |
| 2014/0236296 A1 | 8/2014 | Wagner et al. |
| 2014/0243892 A1 | 8/2014 | Choinski |
| 2014/0243981 A1 | 8/2014 | Davenport et al. |
| 2014/0243982 A1* | 8/2014 | Miller ............ A61F 2/4455 623/17.16 |
| 2014/0249629 A1 | 9/2014 | Moskowitz et al. |
| 2014/0249630 A1 | 9/2014 | Weiman |
| 2014/0257484 A1 | 9/2014 | Flower et al. |
| 2014/0257486 A1 | 9/2014 | Alheidt |
| 2014/0257494 A1 | 9/2014 | Thorwarth et al. |
| 2014/0277139 A1 | 9/2014 | Vrionis et al. |
| 2014/0277204 A1 | 9/2014 | Sandhu |
| 2014/0277464 A1 | 9/2014 | Richter et al. |
| 2014/0277474 A1 | 9/2014 | Robinson et al. |
| 2014/0277476 A1 | 9/2014 | McLean et al. |
| 2014/0277481 A1 | 9/2014 | Lee et al. |
| 2014/0303731 A1 | 10/2014 | Glerum |
| 2014/0303732 A1 | 10/2014 | Rhoda et al. |
| 2014/0324171 A1 | 10/2014 | Glerum et al. |
| 2015/0012097 A1 | 1/2015 | Ibarra et al. |
| 2015/0012098 A1 | 1/2015 | Eastlack et al. |
| 2015/0045894 A1 | 2/2015 | Hawkins et al. |
| 2015/0066145 A1 | 3/2015 | Rogers et al. |
| 2015/0088256 A1 | 3/2015 | Ballard |
| 2015/0094610 A1 | 4/2015 | Morgenstern et al. |
| 2015/0094812 A1 | 4/2015 | Cain |
| 2015/0094813 A1 | 4/2015 | Lechmann et al. |
| 2015/0100128 A1* | 4/2015 | Glerum ............ A61F 2/447 623/17.16 |
| 2015/0112398 A1 | 4/2015 | Morgenstern et al. |
| 2015/0112437 A1 | 4/2015 | Davis et al. |
| 2015/0112438 A1 | 4/2015 | McLean |
| 2015/0157470 A1 | 6/2015 | Voellmicke et al. |
| 2015/0164655 A1 | 6/2015 | Dimauro |

(56) References Cited

U.S. PATENT DOCUMENTS

| | | |
|---|---|---|
| 2015/0173914 A1 | 6/2015 | Dimauro et al. |
| 2015/0173916 A1 | 6/2015 | Cain |
| 2015/0182347 A1 | 7/2015 | Robinson |
| 2015/0190242 A1* | 7/2015 | Blain .............. A61F 2/4611 623/17.12 |
| 2015/0196401 A1 | 7/2015 | Dimauro et al. |
| 2015/0202052 A1 | 7/2015 | Dimauro |
| 2015/0216671 A1 | 8/2015 | Cain |
| 2015/0216672 A1 | 8/2015 | Cain |
| 2015/0216673 A1 | 8/2015 | Dimauro |
| 2015/0230929 A1 | 8/2015 | Lorio |
| 2015/0230932 A1 | 8/2015 | Schaller |
| 2015/0238324 A1 | 8/2015 | Nebosky et al. |
| 2015/0250606 A1 | 9/2015 | McLean |
| 2015/0320571 A1 | 11/2015 | Lechmann et al. |
| 2016/0000577 A1 | 1/2016 | Dimauro |
| 2016/0016309 A1 | 1/2016 | Swift et al. |
| 2016/0022437 A1 | 1/2016 | Kelly et al. |
| 2016/0038301 A1 | 2/2016 | Wickham |
| 2016/0038304 A1 | 2/2016 | Aquino et al. |
| 2016/0045333 A1 | 2/2016 | Baynham |
| 2016/0051376 A1 | 2/2016 | Serhan et al. |
| 2016/0058573 A1 | 3/2016 | Dimauro et al. |
| 2016/0067055 A1 | 3/2016 | Hawkins et al. |
| 2016/0074170 A1 | 3/2016 | Rogers et al. |
| 2016/0074175 A1 | 3/2016 | O'Neil |
| 2016/0081814 A1 | 3/2016 | Baynham |
| 2016/0089247 A1 | 3/2016 | Nichols et al. |
| 2016/0100954 A1 | 4/2016 | Rumi et al. |
| 2016/0106551 A1 | 4/2016 | Grimberg et al. |
| 2016/0113776 A1 | 4/2016 | Capote |
| 2016/0120662 A1 | 5/2016 | Schaller |
| 2016/0128843 A1 | 5/2016 | Tsau et al. |
| 2016/0199195 A1 | 7/2016 | Hauck et al. |
| 2016/0199196 A1 | 7/2016 | Serhan et al. |
| 2016/0228258 A1 | 8/2016 | Schaller et al. |
| 2016/0235455 A1 | 8/2016 | Wahl |
| 2016/0242929 A1 | 8/2016 | Voellmicke et al. |
| 2016/0256291 A1 | 9/2016 | Miller |
| 2016/0310296 A1 | 10/2016 | Dimauro et al. |
| 2016/0317313 A1 | 11/2016 | Dimauro |
| 2016/0317317 A1 | 11/2016 | Marchek et al. |
| 2016/0317714 A1 | 11/2016 | Dimauro et al. |
| 2016/0331541 A1 | 11/2016 | Dimauro et al. |
| 2016/0331546 A1 | 11/2016 | Lechmann et al. |
| 2016/0331548 A1 | 11/2016 | Dimauro et al. |
| 2016/0338854 A1 | 11/2016 | Serhan et al. |
| 2016/0367265 A1 | 12/2016 | Morgenstern Lopez |
| 2016/0367380 A1 | 12/2016 | Dimauro |
| 2016/0374821 A1 | 12/2016 | Dimauro et al. |
| 2017/0000622 A1 | 1/2017 | Thommen et al. |
| 2017/0035578 A1 | 2/2017 | Dimauro et al. |
| 2017/0056179 A1 | 3/2017 | Lorio |
| 2017/0100177 A1 | 4/2017 | Kim |
| 2017/0100255 A1 | 4/2017 | Hleihil et al. |
| 2017/0100260 A1* | 4/2017 | Duffield et al. ........ A61F 2/4611 |
| 2017/0290674 A1 | 10/2017 | Olmos et al. |
| 2017/0304074 A1 | 10/2017 | Dimauro et al. |
| 2018/0055649 A1 | 3/2018 | Kelly et al. |
| 2018/0078379 A1 | 3/2018 | Serhan et al. |
| 2019/0083276 A1 | 3/2019 | Dimauro |
| 2019/0105171 A1 | 4/2019 | Rogers et al. |
| 2020/0008950 A1 | 1/2020 | Serhan et al. |
| 2020/0015982 A1 | 1/2020 | O'Neil |
| 2020/0060843 A1 | 2/2020 | Evans et al. |

FOREIGN PATENT DOCUMENTS

| | | |
|---|---|---|
| CA | 2617872 A1 | 2/2007 |
| CN | 1177918 A | 4/1998 |
| CN | 101087566 A | 12/2007 |
| CN | 101631516 A | 1/2010 |
| CN | 101909548 A | 12/2010 |
| CN | 102164552 A | 8/2011 |
| DE | 2804936 A1 | 8/1979 |
| DE | 3023353 A1 | 4/1981 |
| DE | 3911610 A1 | 10/1990 |
| DE | 4012622 C1 | 7/1991 |
| DE | 19710392 | 7/1999 |
| DE | 19832798 C1 | 11/1999 |
| DE | 20101793 U1 | 5/2001 |
| DE | 202006005868 U1 | 6/2006 |
| DE | 202008001079 U1 | 3/2008 |
| EP | 0077159 A1 | 4/1983 |
| EP | 0260044 A1 | 3/1988 |
| EP | 0270704 A1 | 6/1988 |
| EP | 0282161 A1 | 9/1988 |
| EP | 0433717 A1 | 6/1991 |
| EP | 0525352 A1 | 2/1993 |
| EP | 0529275 A2 | 3/1993 |
| EP | 0611557 A2 | 8/1994 |
| EP | 0621020 A1 | 10/1994 |
| EP | 0625336 A2 | 11/1994 |
| EP | 0678489 A1 | 10/1995 |
| EP | 0743045 A2 | 11/1996 |
| EP | 0853929 A2 | 7/1998 |
| EP | 1046376 A1 | 10/2000 |
| EP | 1157676 A1 | 11/2001 |
| EP | 1290985 A2 | 3/2003 |
| EP | 1374784 A1 | 1/2004 |
| EP | 1378205 A1 | 1/2004 |
| EP | 1532949 A1 | 5/2005 |
| EP | 1541096 A1 | 6/2005 |
| EP | 1385449 B1 | 7/2006 |
| EP | 1683593 A2 | 7/2006 |
| EP | 1698305 A1 | 9/2006 |
| EP | 1843723 A1 | 10/2007 |
| EP | 1845874 A1 | 10/2007 |
| EP | 1924227 A2 | 5/2008 |
| EP | 2331023 A2 | 6/2011 |
| EP | 2368529 A1 | 9/2011 |
| EP | 2237748 B1 | 9/2012 |
| EP | 2641571 A1 | 9/2013 |
| EP | 2705809 A1 | 3/2014 |
| EP | 2764851 A1 | 8/2014 |
| FR | 2649311 A1 | 1/1991 |
| FR | 2699065 A1 | 6/1994 |
| FR | 2712486 A1 | 5/1995 |
| FR | 2718635 A1 | 10/1995 |
| FR | 2728778 A1 | 7/1996 |
| FR | 2730159 A1 | 8/1996 |
| FR | 2745709 A1 | 9/1997 |
| FR | 2800601 A1 | 5/2001 |
| FR | 2801189 A1 | 5/2001 |
| FR | 2808182 A1 | 11/2001 |
| FR | 2874814 A1 | 3/2006 |
| FR | 2913331 A1 | 9/2008 |
| GB | 2157788 A | 10/1985 |
| GB | 2173565 A | 10/1986 |
| JP | 6452439 A | 2/1989 |
| JP | 06-500039 A | 1/1994 |
| JP | 06-319742 A | 11/1994 |
| JP | 07-502419 A | 3/1995 |
| JP | 07-184922 A | 7/1995 |
| JP | 1085232 A | 4/1998 |
| JP | 11-089854 A | 4/1999 |
| JP | 2003-010197 A | 1/2003 |
| JP | 2003-126266 A | 5/2003 |
| JP | 2003-526457 A | 9/2003 |
| JP | 2006-516456 | 7/2006 |
| JP | 2007-054666 A | 3/2007 |
| JP | 2008-126085 A | 6/2008 |
| JP | 2011-509766 A | 3/2011 |
| JP | 2011-520580 A | 7/2011 |
| JP | 2012-020153 A | 2/2012 |
| JP | 4988203 B2 | 8/2012 |
| JP | 5164571 B2 | 3/2013 |
| WO | 91/09572 A1 | 7/1991 |
| WO | 93/04634 A1 | 3/1993 |
| WO | 93/04652 A1 | 3/1993 |
| WO | 93/17669 A1 | 9/1993 |
| WO | 94/04100 A1 | 3/1994 |
| WO | 95/31158 | 11/1995 |

(56) References Cited

FOREIGN PATENT DOCUMENTS

| | | |
|---|---|---|
| WO | 96/28100 A1 | 9/1996 |
| WO | 97/00054 A1 | 1/1997 |
| WO | 97/26847 A1 | 7/1997 |
| WO | 98/34552 A1 | 8/1998 |
| WO | 99/02214 A1 | 1/1999 |
| WO | 99/42062 A1 | 8/1999 |
| WO | 99/52478 A1 | 10/1999 |
| WO | 99/53871 A1 | 10/1999 |
| WO | 99/62417 A1 | 12/1999 |
| WO | 00/12033 | 3/2000 |
| WO | 00/13620 A1 | 3/2000 |
| WO | 00/67652 | 5/2000 |
| WO | 00/44288 A1 | 8/2000 |
| WO | 00/53127 A1 | 9/2000 |
| WO | 00/67650 A1 | 11/2000 |
| WO | 00/67651 A1 | 11/2000 |
| WO | 00/74605 A1 | 12/2000 |
| WO | 00/76409 A1 | 12/2000 |
| WO | 01/01893 A1 | 1/2001 |
| WO | 01/01895 A1 | 1/2001 |
| WO | 01/10316 A1 | 2/2001 |
| WO | 01/12054 A2 | 2/2001 |
| WO | 01/17464 A1 | 3/2001 |
| WO | 01/80751 A1 | 11/2001 |
| WO | 02/17824 A2 | 3/2002 |
| WO | 02/17825 A2 | 3/2002 |
| WO | 02/30338 A1 | 4/2002 |
| WO | 02/43601 A2 | 6/2002 |
| WO | 02/43628 A1 | 6/2002 |
| WO | 02/47563 A1 | 6/2002 |
| WO | 02/71921 A2 | 9/2002 |
| WO | 02/85250 A2 | 10/2002 |
| WO | 03/02021 A2 | 1/2003 |
| WO | 03/05937 A1 | 1/2003 |
| WO | 03/07854 A1 | 1/2003 |
| WO | 03/20169 A2 | 3/2003 |
| WO | 03/21308 A2 | 3/2003 |
| WO | 03/22165 A1 | 3/2003 |
| WO | 03/28587 A2 | 4/2003 |
| WO | 03/43488 A2 | 5/2003 |
| WO | 2003/051557 A1 | 6/2003 |
| WO | 2003/101308 A1 | 12/2003 |
| WO | 2004/008949 A2 | 1/2004 |
| WO | 03/59180 A2 | 3/2004 |
| WO | 2004/034924 A2 | 4/2004 |
| WO | 2004/062505 A1 | 7/2004 |
| WO | 2004/064603 A2 | 8/2004 |
| WO | 2004/073563 A2 | 9/2004 |
| WO | 2004/078220 A2 | 9/2004 |
| WO | 2004/078221 A2 | 9/2004 |
| WO | 2004/082526 A2 | 9/2004 |
| WO | 2004/098420 A2 | 11/2004 |
| WO | 2004/098453 A2 | 11/2004 |
| WO | 2004/108022 A1 | 12/2004 |
| WO | 2005/027734 A2 | 3/2005 |
| WO | 2005/032433 A2 | 4/2005 |
| WO | 2005/039455 A1 | 5/2005 |
| WO | 2005/051246 A2 | 6/2005 |
| WO | 2005/081877 A2 | 9/2005 |
| WO | 2005/112834 A2 | 12/2005 |
| WO | 2005/112835 A2 | 12/2005 |
| WO | 2006/017507 A2 | 2/2006 |
| WO | 2006/047587 A2 | 5/2006 |
| WO | 2006/047645 A2 | 5/2006 |
| WO | 2006/058281 A2 | 6/2006 |
| WO | 2006/060420 A1 | 6/2006 |
| WO | 2006/063083 A1 | 6/2006 |
| WO | 2006/065419 A2 | 6/2006 |
| WO | 2006/066228 A2 | 6/2006 |
| WO | 2006/072941 A2 | 7/2006 |
| WO | 2006/081843 A1 | 8/2006 |
| WO | 2006/108067 A2 | 10/2006 |
| WO | 2007/009107 A2 | 1/2007 |
| WO | 2007/022194 A2 | 2/2007 |
| WO | 2007/028098 A2 | 3/2007 |
| WO | 2007/048012 A2 | 4/2007 |
| WO | 2007/067726 A2 | 6/2007 |
| WO | 2007/084427 A2 | 7/2007 |
| WO | 2007/119212 A2 | 10/2007 |
| WO | 2007/124130 A2 | 11/2007 |
| WO | 2008/004057 A2 | 1/2008 |
| WO | 2008/044057 A1 | 4/2008 |
| WO | 2008/064842 A2 | 6/2008 |
| WO | 2008/070863 A2 | 6/2008 |
| WO | 2008/103781 A2 | 8/2008 |
| WO | 2008/103832 A2 | 8/2008 |
| WO | 2009/064787 A2 | 5/2009 |
| WO | 2009/092102 A1 | 7/2009 |
| WO | 2009/124269 A1 | 10/2009 |
| WO | 2009/143496 A1 | 11/2009 |
| WO | 2009/147527 A2 | 12/2009 |
| WO | 2009/152919 A1 | 12/2009 |
| WO | 2010/068725 A2 | 6/2010 |
| WO | 2010/088766 A1 | 8/2010 |
| WO | 2010/136170 A1 | 12/2010 |
| WO | 2010/148112 A1 | 12/2010 |
| WO | 2011/005788 A1 | 1/2011 |
| WO | 2011/046459 A1 | 4/2011 |
| WO | 2011/046460 A1 | 4/2011 |
| WO | 2011/079910 A2 | 7/2011 |
| WO | 2011/119617 A1 | 9/2011 |
| WO | 2011/142761 A1 | 11/2011 |
| WO | 2011/150350 A1 | 12/2011 |
| WO | 2012/009152 A1 | 1/2012 |
| WO | 2012/028182 A1 | 3/2012 |
| WO | 2012/030331 A1 | 3/2012 |
| WO | 2012/089317 A1 | 7/2012 |
| WO | 2012/122294 A1 | 9/2012 |
| WO | 2012/135764 A1 | 10/2012 |
| WO | 2013/006669 A2 | 1/2013 |
| WO | 2013/023096 A1 | 2/2013 |
| WO | 2013/025876 A1 | 2/2013 |
| WO | 2013/043850 A2 | 3/2013 |
| WO | 2013/062903 A1 | 5/2013 |
| WO | 2013/082184 A1 | 6/2013 |
| WO | 2013/158294 A1 | 10/2013 |
| WO | 2013/173767 A1 | 11/2013 |
| WO | 2013/184946 A1 | 12/2013 |
| WO | 2014/014610 A1 | 1/2014 |
| WO | 2014/018098 A1 | 1/2014 |
| WO | 2014/026007 A1 | 2/2014 |
| WO | 2014/035962 A1 | 3/2014 |
| WO | 2014/088521 A2 | 6/2014 |
| WO | 2014/116891 A1 | 7/2014 |
| WO | 2014/144696 A1 | 9/2014 |
| WO | 2015/048997 A1 | 4/2015 |
| WO | 2016/069796 A1 | 5/2016 |
| WO | 2016/127139 A1 | 8/2016 |

OTHER PUBLICATIONS

Talwar "Insertion loads of the X STOP interspinous process distraction system designed to treat neurogenic intermittent claudication", Eur Spine J. (2006) 15: pp. 908-912.
Spine Solutions Brochure—Prodisc 2001, 16 pages.
Siddiqui, "The Positional Magnetic Resonance Imaging Changes in the Lumbar Spine Following Insertion of a Novel Interspinous Process Distraction Device", Spine, vol. 30, No. 23, pp. 2677-2682, 2005.
Shin, "Posterior Lumbar Interbody Fusion via a Unilateral Approach", Yonsei Medical Journal, 2006, pp. 319-325, vol. 47(3).
ProMap Tm EMG Navigation Probe. Technical Brochure Spineology Inc, Dated May 2009.
Polikeit, "The Importance of the Endplate for Interbody Cages in the Lumbar Spine", Eur. Spine J., 2003, pp. 556-561, vol. 12.
Niosi, Christina A., "Biomechanical Characterization of the three-dimentinoal kinematic behavior of the Dynesys dynamic stabilization system: an in vitro study", Eur Spine J. (2006) 15: pp. 913-922.
Morgenstern R; "Transforaminal Endoscopic Stenosis Surgery—A Comparative Study of Laser and Reamed Foraminoplasty", in European Musculoskeletal Review, Issue 1, 2009.

(56) References Cited

OTHER PUBLICATIONS

Method and Apparatus for Spinal Stabilization, U.S. Appl. No. 60/942,998.
Method and Apparatus for Spinal Fixation, U.S. Appl. No. 60/794,171.
Method and Apparatus for Spinal Fixation, U.S. Appl. No. 60/424,055.
Method and apparatus for spinal fixation, U.S. Appl. No. 60/397,588.
Medco Forum, "Percutaneous Lumbar Fixation via PERPOS System From Interventional Spine", Oct. 2007, vol. 14, No. 49.
Medco Forum, "Percutaneous Lumbar Fixation Via PERPOS PLS System Interventional Spine", Sep. 2008, vol. 15, No. 37.
Mahar et al., "Biomechanical Comparison of Novel Percutaneous Transfacet Device and a Traditional Posterior System for Single Level Fusion", Journal of Spinal Disorders & Techniques, Dec. 2006, vol. 19, No. 8, pp. 591-594.
Link SB Charite Brochure—Intervertebral Prosthesis 1988, 29 pages.
Krbec, "Replacement of the Vertebral Body with an Expansion Implant (Synex)", Acta Chir Orthop Traumatol Cech, 2002, pp. 158-162, vol. 69(3).
King, M.D., Don, "Internal Fixation for Lumbosacral Fusion", The Journal of Bone and Joint Surgery, J. Bone Joint Surg Am., 1948; 30: 560-578.
Kambin et al., "Percutaneous Lateral Discectomy of the Lumbar Spine: A Preliminary Report", Clin. Orthop,: 1983, 174: 127-132.
Iprenburg et al., "Transforaminal Endoscopic Surgery in Lumbar Disc Herniation in an Economic Crisis—The TESSYS Method", US Musculoskeletal, 2008, p. 47-49.
Hunt, "Expandable Cage Placement Via a Posterolateral Approach in Lumbar Spine Reconstructions", Journal of Neurosurgery: Spine, Sep. 2006, pp. 271-274, vol. 5.
Hoogland et al., "Total Lumar Intervertebral Disc Replacement: Testing a New Articulating Space in Human Cadaver Spines-24 1", Annual ORS, Dallas, TX, Feb. 21-23, 1978, 8 pages.
Gray's Anatomy, Crown Publishers, Inc., 1977, pp. 33-54.
Gore, "Technique of Cervical Interbody Fusion", Clinical Orthopaedics and Related Research, Sep. 1984, pp. 191-195, No. 188.
Fuchs, "The use of an interspinous implant in conjuction with a graded facetectomy procedure", Spine vol. 30, No. 11, pp. 1266-1272, 2005.
Folman, Posterior Lumbar Interbody Fusion for Degenerative Disc Disease Using a Minimally Invasive B-Twin Expandable Spinal Spacer, Journal of Spinal Disorders & Techniques, 2003, pp. 455-460, vol. 16(5).
Expandable Implant, U.S. Appl. No. 61/675,975.
Chin, "Early Results of the Triage Medical Percutaneous Transfacet Pedicular BONE-LOK Compression Device for Lumbar Fusion", Accessed online Jul. 10, 2017, 10 pages.
Chiang, "Biomechanical Comparison of Instrumented Posterior Lumbar Interbody Fusion with One or Two Cages by Finite Element Analysis", Spine, Sep. 2006, pp. E682-E689, vol. 31(19), Lippincott Williams & Wilkins, Inc.
Brooks et al., "Efficacy of Supplemental Posterior Transfacet Pedicle Device Fixation in the Setting of One- or Two-Level Anterior Lumbar Interbody Fusion", Retrieved Jun. 19, 2017, 6 pages.
Brochure for PERPOS PLS System Surgical Technique by Interventional Spine, 2008, 8 pages.
Alfen et al., "Developments in the area of Endoscopic Spine Surgery", European Musculoskeletal Review 2006, pp. 23-24, Thessys(Trademark), Transforaminal Endoscopic Spine Systems, joi max Medical Solutions.
U.S. Appl. No. 60/942,998, Method and Apparatus for Spinal Stabilization, filed Jun. 8, 2007.
U.S. Appl. No. 61/675,975, Expandable Implant, filed Jul. 26, 2012.
U.S. Appl. No. 60/397,588, Method and apparatus for spinal fixation, filed Jul. 19, 2002.
U.S. Appl. No. 60/794,171, Method and apparatus for spinal fixation, filed Apr. 21, 2006.
U.S. Appl. No. 60/424,055, filed Nov. 5, 2002, entitled Method and apparatus for spinal fixation.
Barakat et al., Macromolecular engineering of polylactone and polylactide. XXI. Controlled synthesis of low molecular weight polylactide macromonomers. J Polym Sci Polym Chem 34:497-502, 1996.
Bruder et al., Identification and characterization of a cell surface differentiation antigen on human osteoprogenitor cells. 42nd Annual Meeting of the Orthopaedic Research Society. p. 574, Feb. 19-22, 1996, Atlanta, Georgia.
Bruder et al., Monoclonal antibodies reactive with human osteogenic cell surface antigens. Bone. Sep. 1997;21 (3):225-235.
Burkoth et al., A review of photocrosslinked polyanhydrides: in situ forming degradable networks. Biomaterials. Dec. 2000; 21 (23): 2395-2404.
Cambridge Scientific News, FDA Approves Cambridge Scientific, Inc.'s Orthopedic WISORB (TM) Malleolar Screw [online], Jul. 30, 2002 [retrieved on Oct. 14, 2003]. Retrieved from the Internet <URL: http://www.cambridgescientificinc.com>.
Carrino, John A., Roxanne Chan and Alexander R. Vaccaro, "Vertebral Augmentation: Vertebroplasty and Kyphoplasty", Seminars in Roentgenology, vol. 39, No. 1 Jan. 2004: pp. 68-84.
Cheng, B.C., Ph.D., Biomechanical pullout strength and histology of Plasmapore Registered XP coated implants: Ovine multi time point survival study. Aesculap Implant Systems, LLC, 2013, 12 pages.
Domb, Biodegradable bone cement compositions based on acrylate and epoxide terminated poly(propylene fumarate) oligomers and calcium salt compositions, Biomaterials 17, 1996, 411-417.
Edeland, H.G., "Some Additional Suggestions for an Intervertebral Disc Prosthesis", J of Bio Medical Engr., vol. 7(1) pp. 57-62, Jan. 1985.
European Search Report EP03253921 dated Nov. 13, 2003, 4 pages.
Flemming et al., Monoclonal anitbody against adult marrow-derived mesenchymal stem cells recognizes developing vasculature in embryonic human skin. Developmental Dynamics. 1998;212:119-132.
Ha et al. (Topographical characterization and microstructural interface analysis of vacuum-plasma-sprayed titanium and hydroxyapatite coatings on carbon fiber-reinforced poly(etheretherketone), Journal of Materials Science: Materials in Science 9 (1997), pp. 891-896.
Haas, Norbert P., New Products from AO Development [online], May 2002 [retrieved on Oct. 14, 2003]. Retrieved from the Internet <URL: http://www.ao.asif.ch/development/pdf_tk_news_02.pdf>.
Hao et al., Investigation of nanocomposites based on semi-interpenetrating network of [L-poly (epsilon-caprolactone)]/[net-poly (epsilon-caprolactone)] and hydroxyapatite nanocrystals. Biomaterials. Apr. 2003;24(9): 1531-9.
Harsha et al., Tribo performance of polyaryletherketone composites, Polymer Testing (21) (2002) pp. 697-709.
Haynesworth et al., Cell surface antigens on human marrow-derived mesenchymal cells are detected by monoclonal antibodies. Bone. 1992;13(1):69-80.
Hitchon et al., Comparison of the biomechanics of hydroxyapatite and polymethylmethacrylate vertebroplasty in a cadaveric spinal compression fracture model. J Neurosurg. Oct. 2001;95(2 Suppl):215-20.
International Patent Application No. PCT /US2013/029014, International Search Report dated Jul. 1, 2013, 7 pages.
Joshi, Ajeya P., M.D. and Paul A. Glazer, M.D., "Vertebroplasty: Current Concepts and Outlook for the Future", 2003, (5 pages), From: http://www.orthojournalhms.org/html/pdfs/manuscript-15.pdf.
Kandziora, Frank, et al., "Biomechanical Analysis of Biodegradable Interbody Fusion Cages Augmented with Poly (propylene Glycol-co-Fumaric Acid)," SPINE, 27(15): 1644-1651 (2002).
Kotsias, A., Clinical trial of titanium-coated PEEL cages anterior cervical discectomy and fusion. [Klinishe Untersuching zum Einsatz von titanbeschichteten Polyetheretherketon—Implantaten bei der cervikalen interkorporalen fusion]. Doctoral thesis. Department of Medicine, Charite, University of Medicine Berlin, 2014, 73 pages. (German language document/Engl. summary).
Kricheldorf et al., Polylactides—synthesis, characterization and medical applications. Macromol Symp 103:85-102, 1996.

(56) References Cited

OTHER PUBLICATIONS

Kroschwitz et al., eds., Hydrogels. Concise Encyclopedia of Polymer Science and Engineering. Wiley and Sons, pp. 458-459, 1990.
Lendlein et al., AB-polymer networks based on oligo(epsilon-caprolactone) segments showing shape-memory properties. Proc Natl Acad Sci US A. Jan. 30, 2001;98(3):842-7. Epub Jan. 23, 2001.
Malberg. M.I., MD; Pimenta, L., MD; Millan, M.M., Md, 9th International Meeting on Advanced Spine Techniques, May 23-25, 2002, Montreux, Switzerland. Paper #54, Paper #60, and E-Poster #54, 5 pages.
Massia et al, An RGD spacing of 440 nm is sufficient for integrin alpha V beta 3-mediated fibroblast spreading and 140 nm for focal contact and stress fiber formation. J Cell Biol 114:1089-1100, 1991.
McAfee et al., Minimally invasive anterior retroperitoneal approach to the lumbar spine: Emphasis on the lateral BAK. SPINE. 1998;23(13):1476-84.
Mendez et al., Self-curing acrylic formulations containing PMMA/PCL composites: properties and antibiotic release behavior. J Biomed Mater Res. Jul. 2002;61 (1):66-74.
Nguyen et al., Poly(Aryl-Ether-Ether-Ketone) and its Advanced Composites: A Review, Polymer Composites, Apr. 1987, vol. 8, No. 2, pp. 57-73.
Osteoset Registered DBM Pellets (Important Medical Information) [online], Nov. 2002 [retrieved on Oct. 14, 2003]. Retrieved from the Internet <URL: http://www.wmt.com/Literature>.
Porocoat(R) Porous Coating, 1 Page, https://emea.depuysynthese.com/hcp/hip/products/qs/porocoat-porous-coatingemea Accessed on Jul. 31, 2017.

Regan et al., Endoscopic thoracic fusion cage. Atlas of Endoscopic Spine Surgery. Quality Medical Publishing, Inc. 1995;350-354.
Slivka et al., In vitro compression testing of fiber-reinforced, bioabsorbable, porous implants. Synthetic Bioabsorbable Polymers for Implants. STP1396, pp. 124-135, ATSM International, Jul. 2000.
Sonic Accelerated Fracture Healing System/Exogen 3000. Premarket Approval. U.S. Food & Drug Administration. Date believed to be May 10, 2000. Retrieved Jul. 23, 2012 from <http://www.accessdata.fda.gov/scripts/cdrh/cfdocs/cfPMA/pma.cfm?id=14736#>. 4 pages, 2012.
Stewart et al., Co-expression of the stro-1 anitgen and alkaline phosphatase in cultures of human bone and marrow cells. ASBMR 18th Annual Meeting. Bath Institute for Rheumatic Diseases, Bath, Avon, UK. Abstract No. P208, p. S142, 1996.
Timmer et al., In vitro degradation of polymeric networks of poly(propylene fumarate) and the crosslinking macromer poly(propylene fumarate)-diacrylate. Biomaterials. Feb. 2003;24(4):571-7.
United States Disctrict Court, Central District of California, Case No. 1:10-CV-00849-LPS, *Nuvasive, Inc.*, vs., *Globus Medical, Inc.*, Videotaped Deposition of: Luiz Pimenta, M.D., May 9, 2012, 20 pages.
Walsh et al., Preparation of porous composite implant materials by in situ polymerization of porous apatite containing epsilon-caprolactone or methyl methacrylate. Biomaterials. Jun. 2001;22(11):1205-12.
Zimmer.com, Longer BAK/L Sterile Interbody Fusion Devices. Date believed to be 1997. Product Data Sheet.Zimmer. Retrieved Jul. 23, 2012 from <http:/ catalog.zimmer.com/contenUzpc/products/600/600/620/S20/S045. html>, 2 pages.

\* cited by examiner

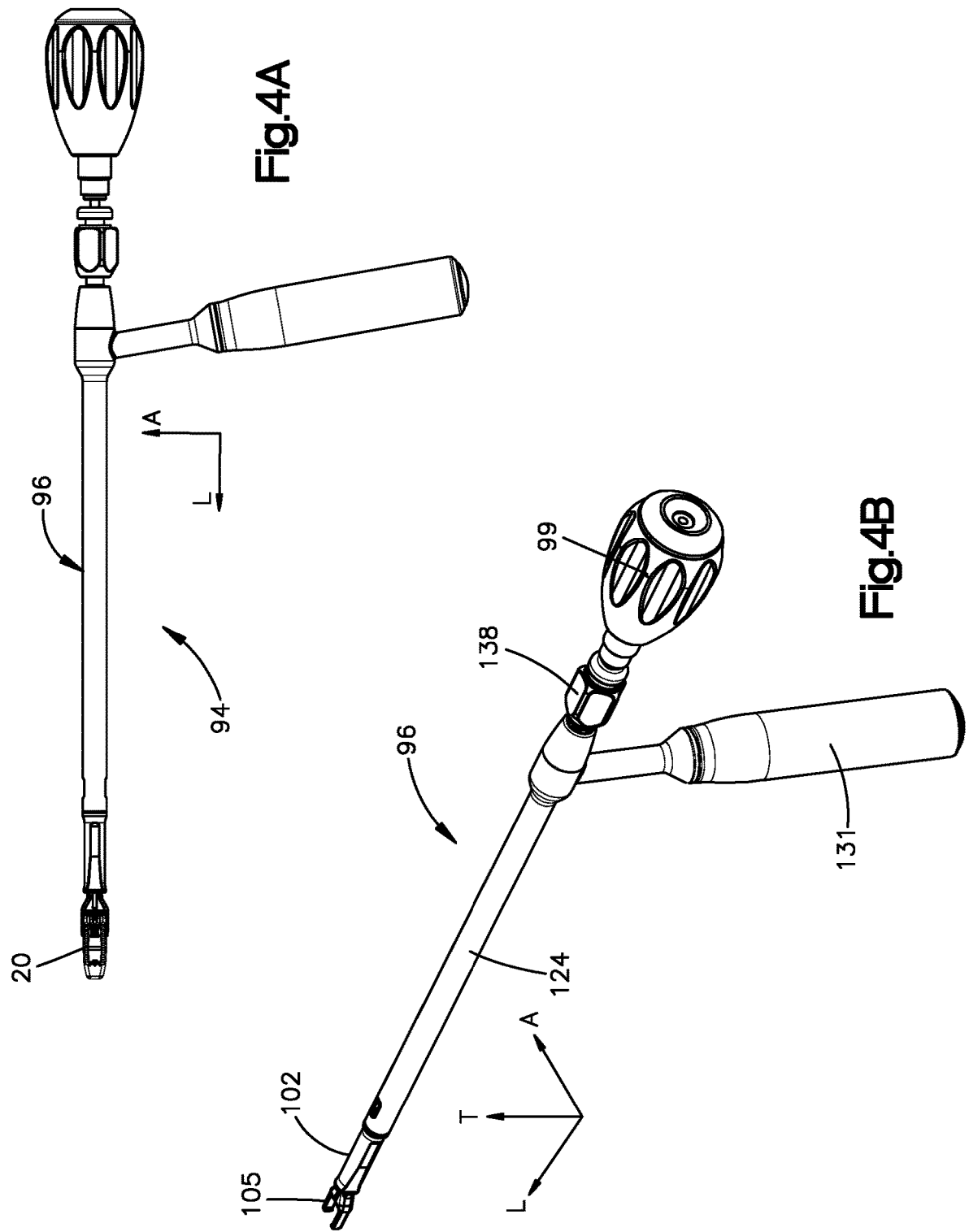

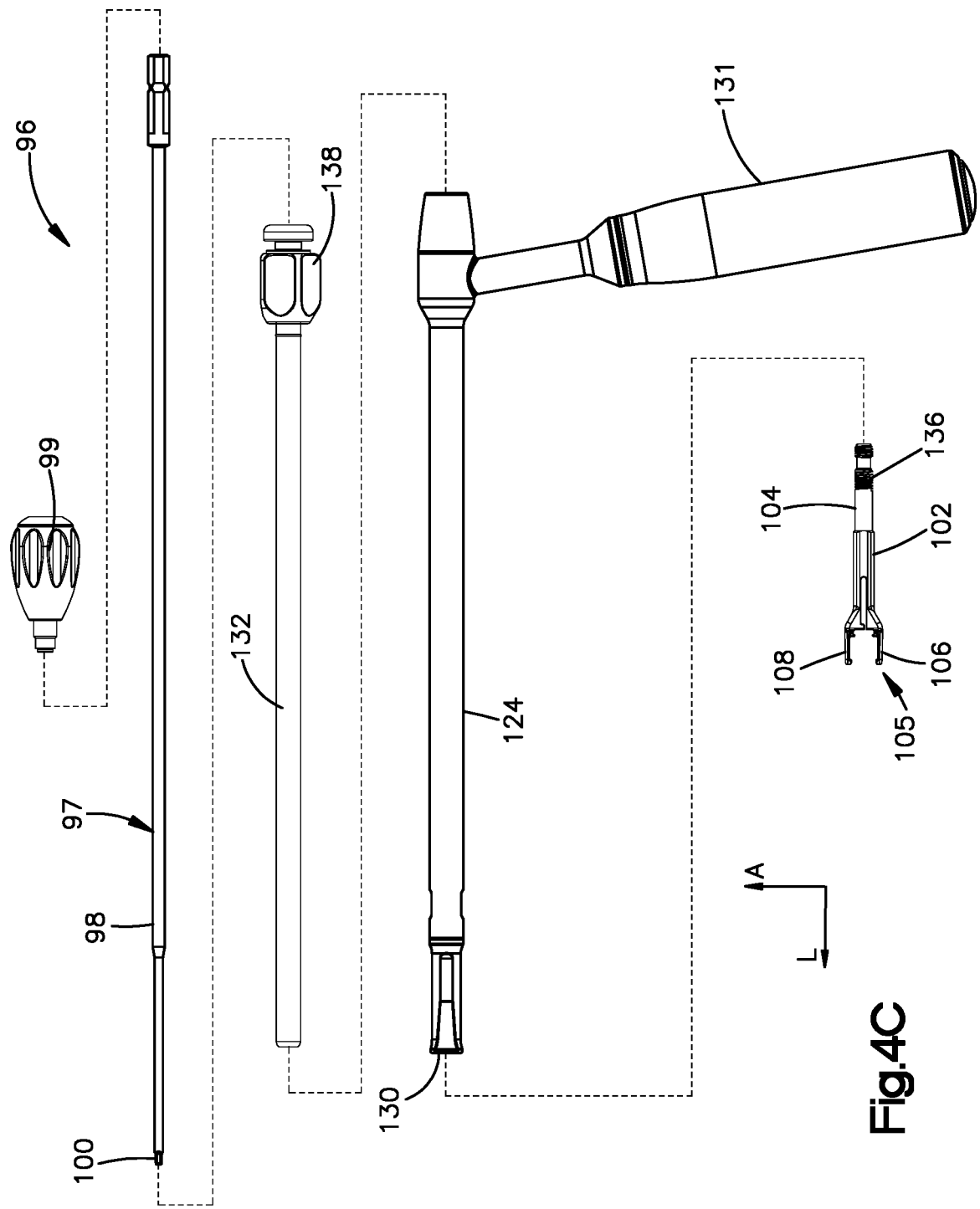

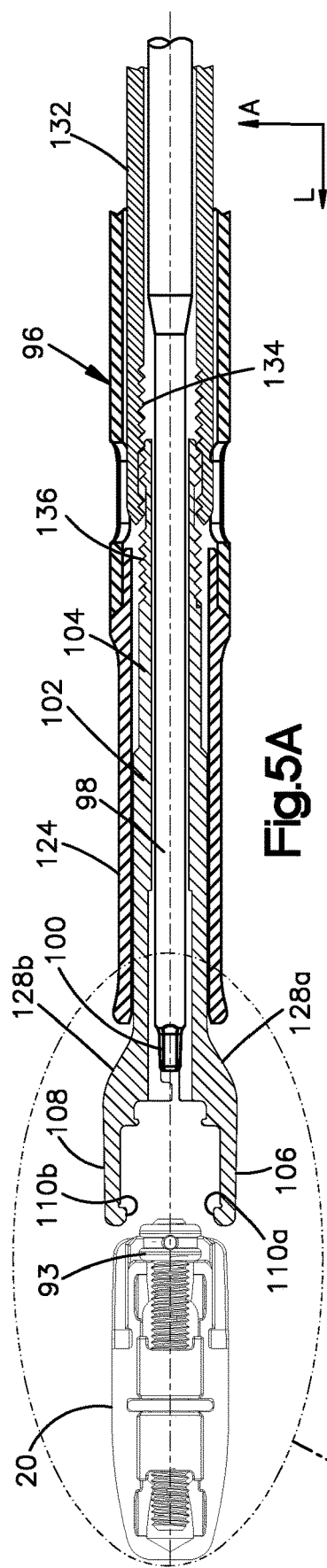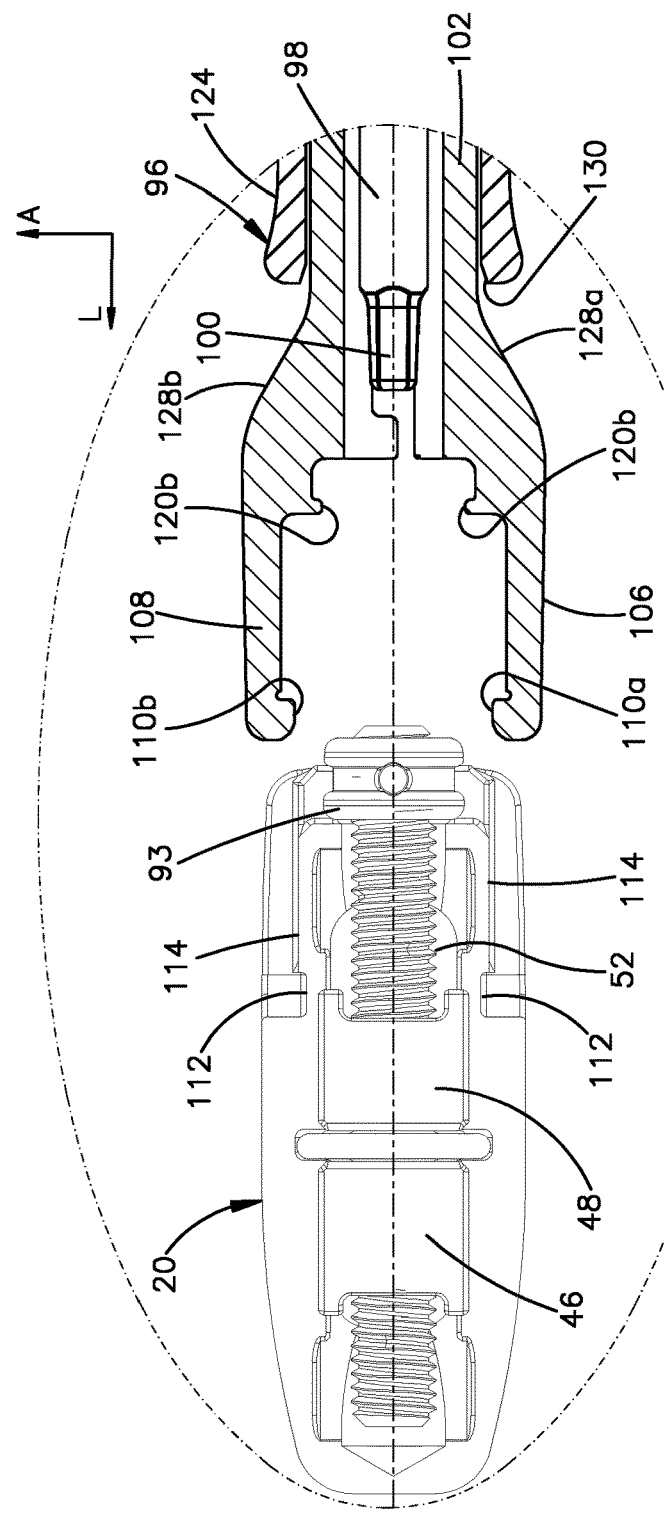
Fig.5A
Fig.5B

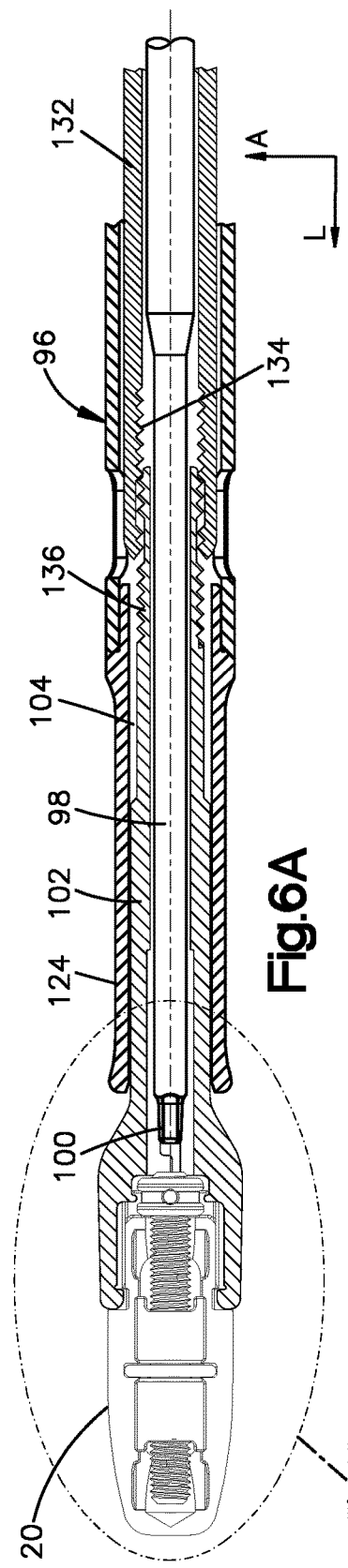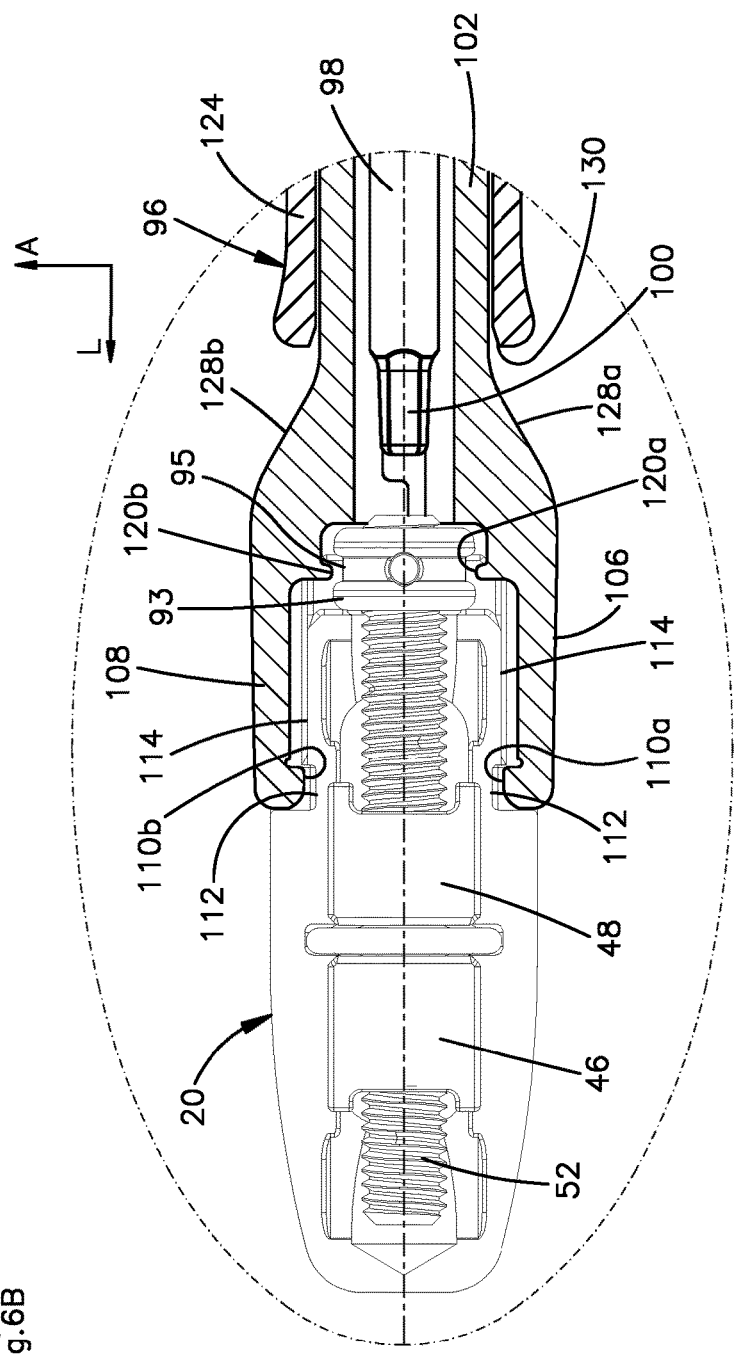

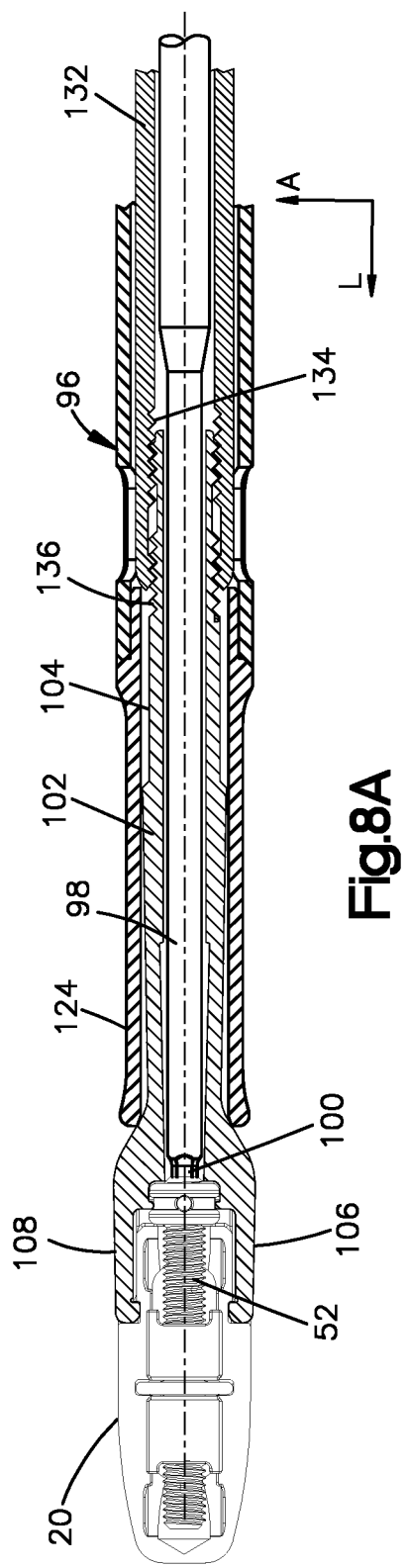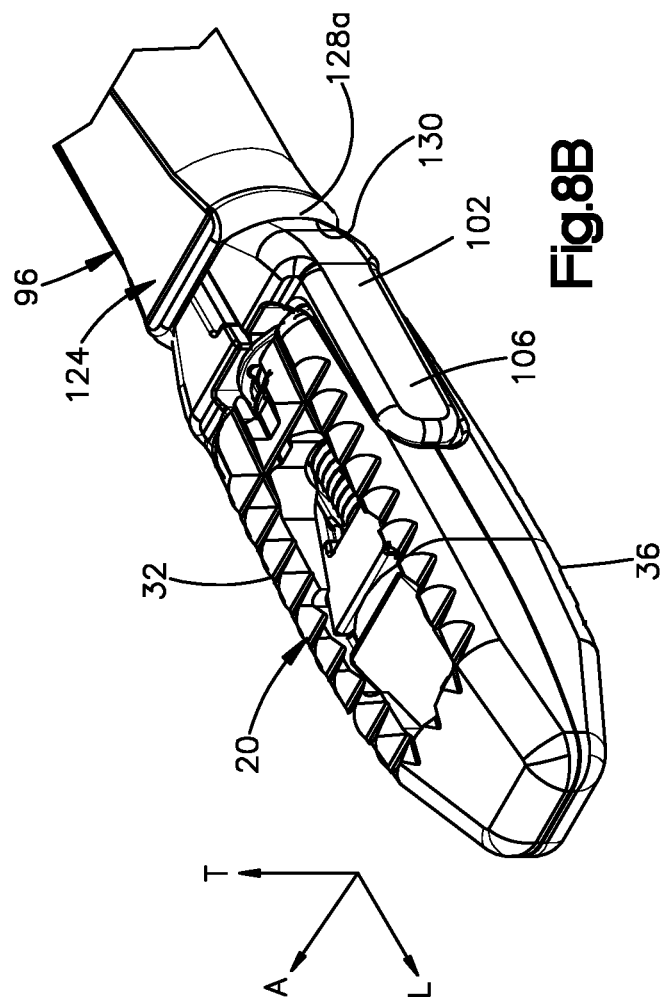

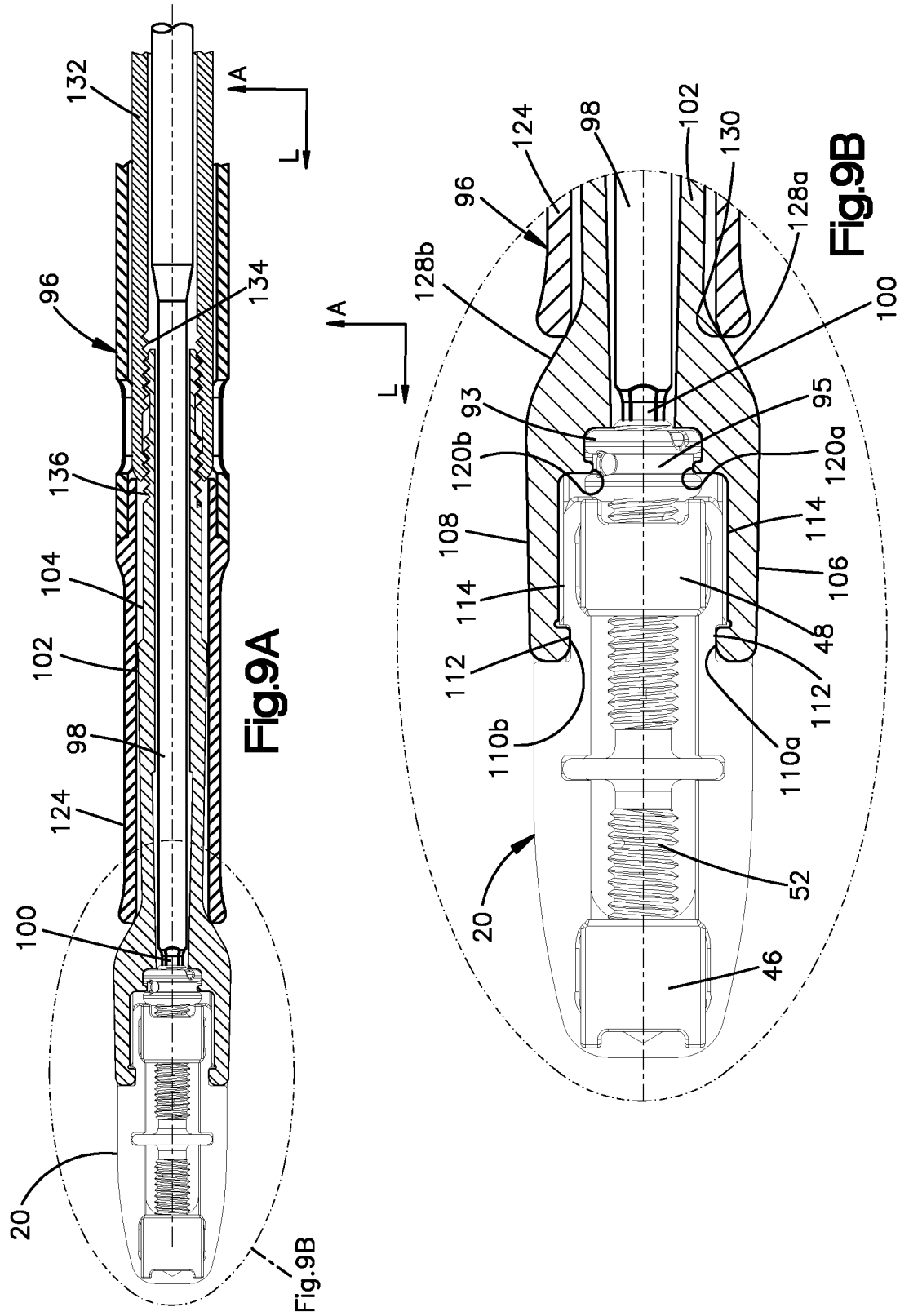

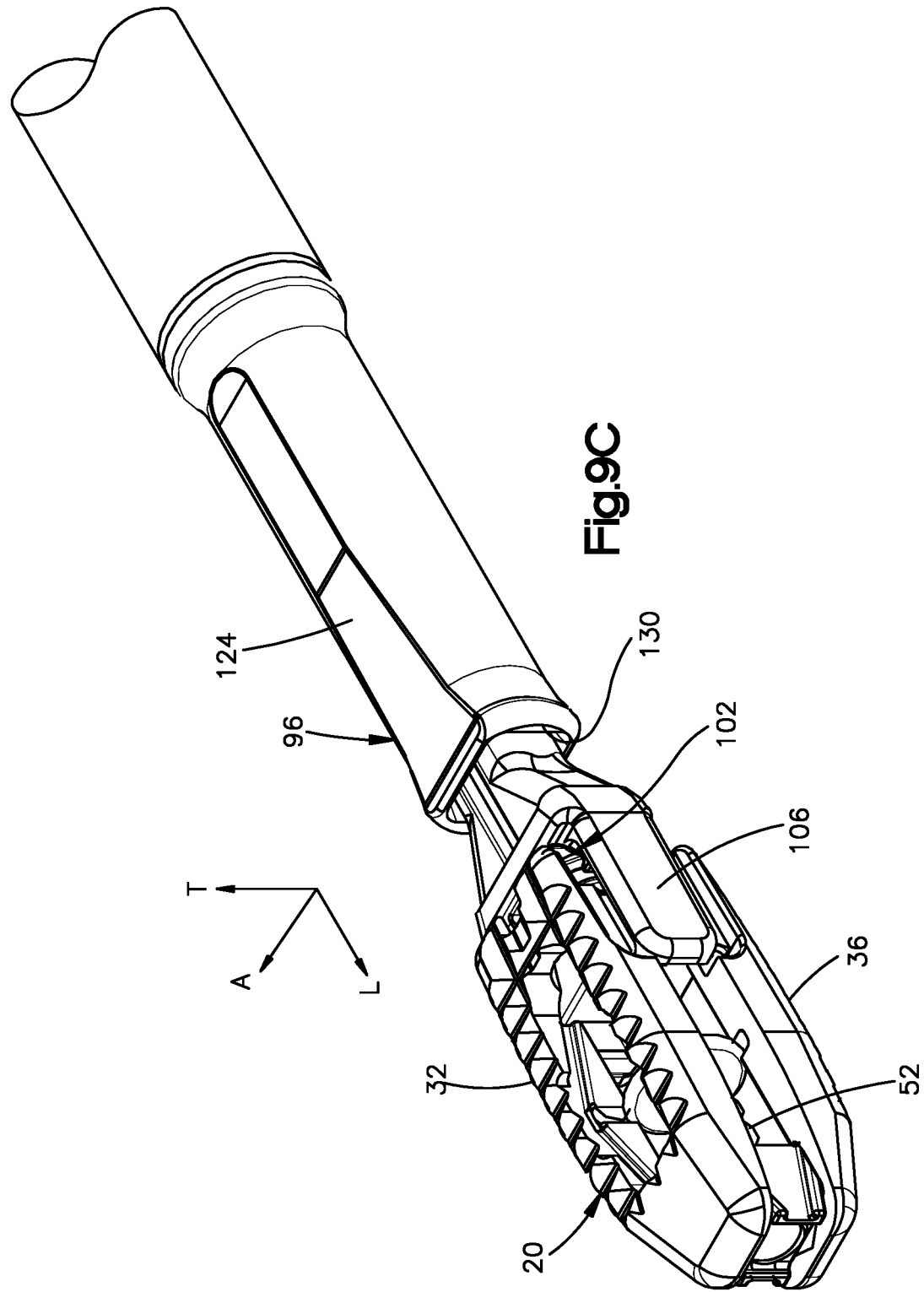

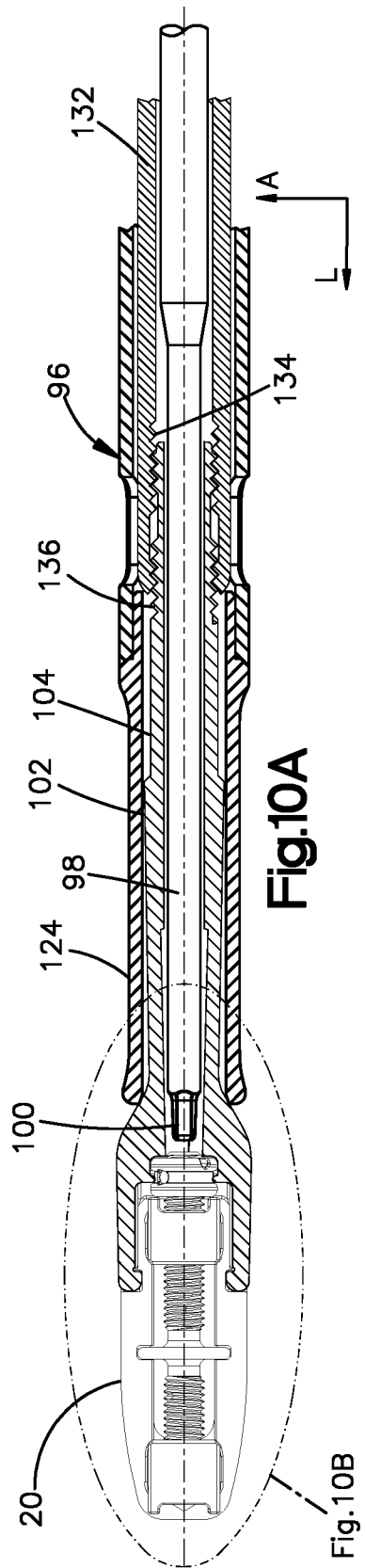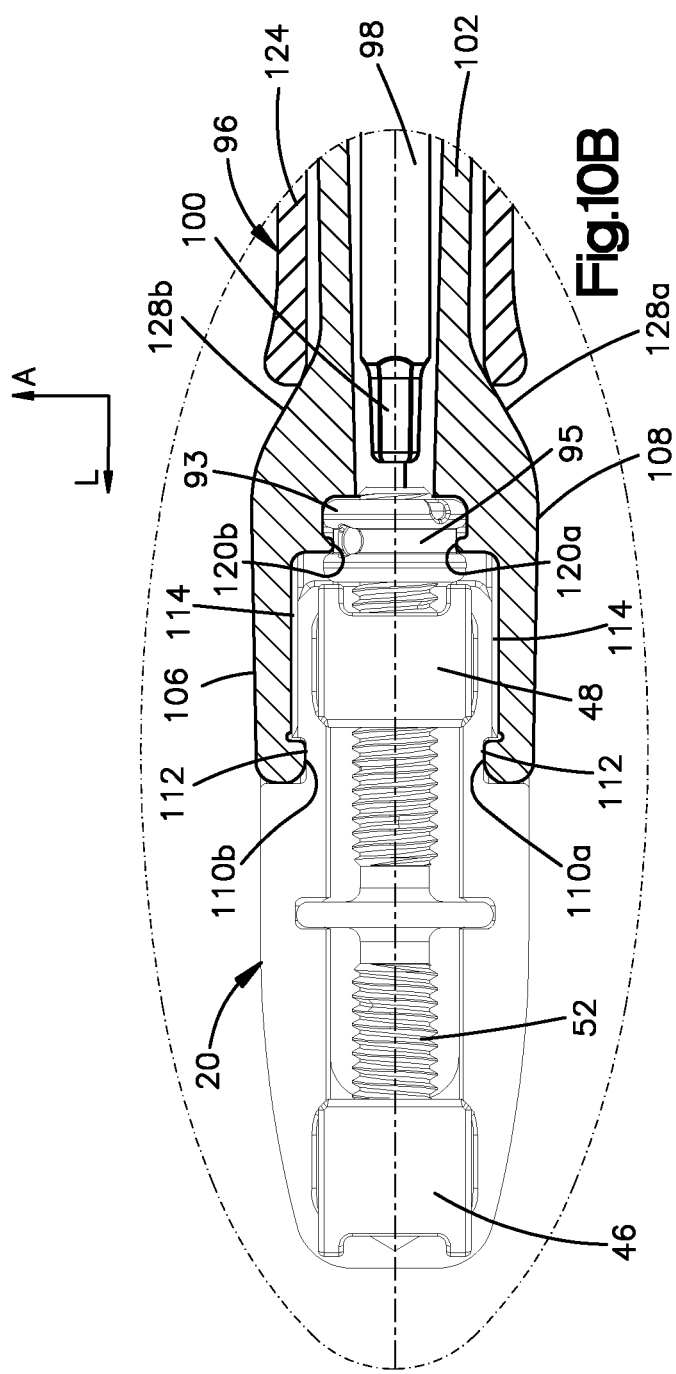

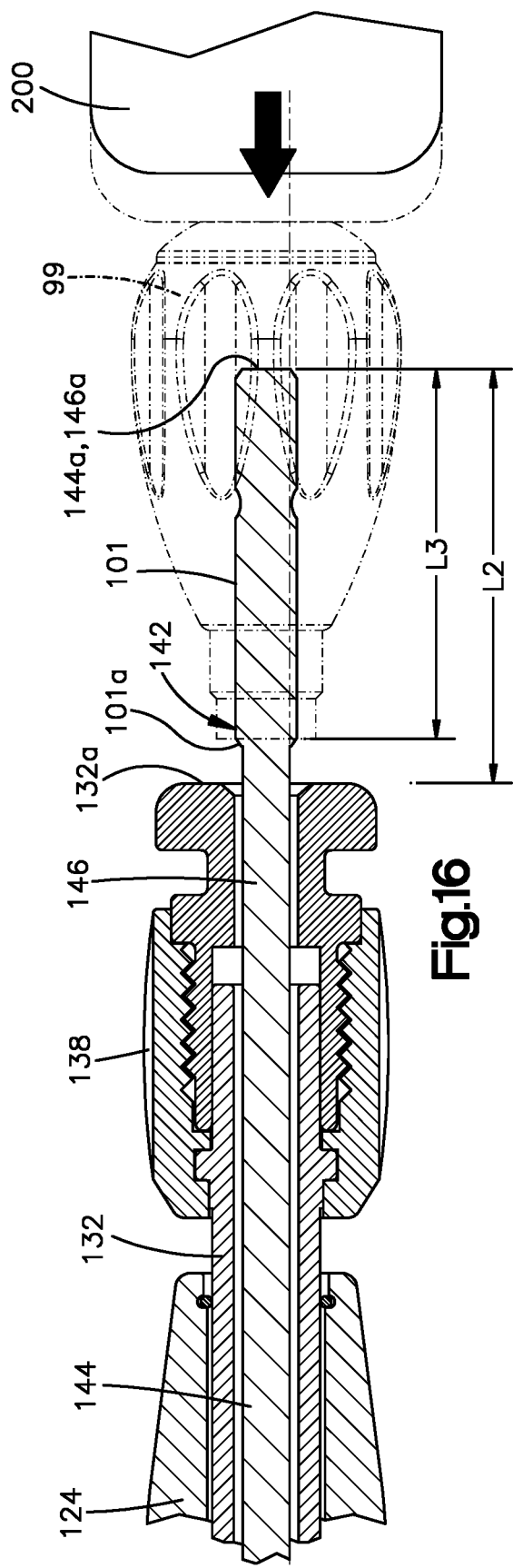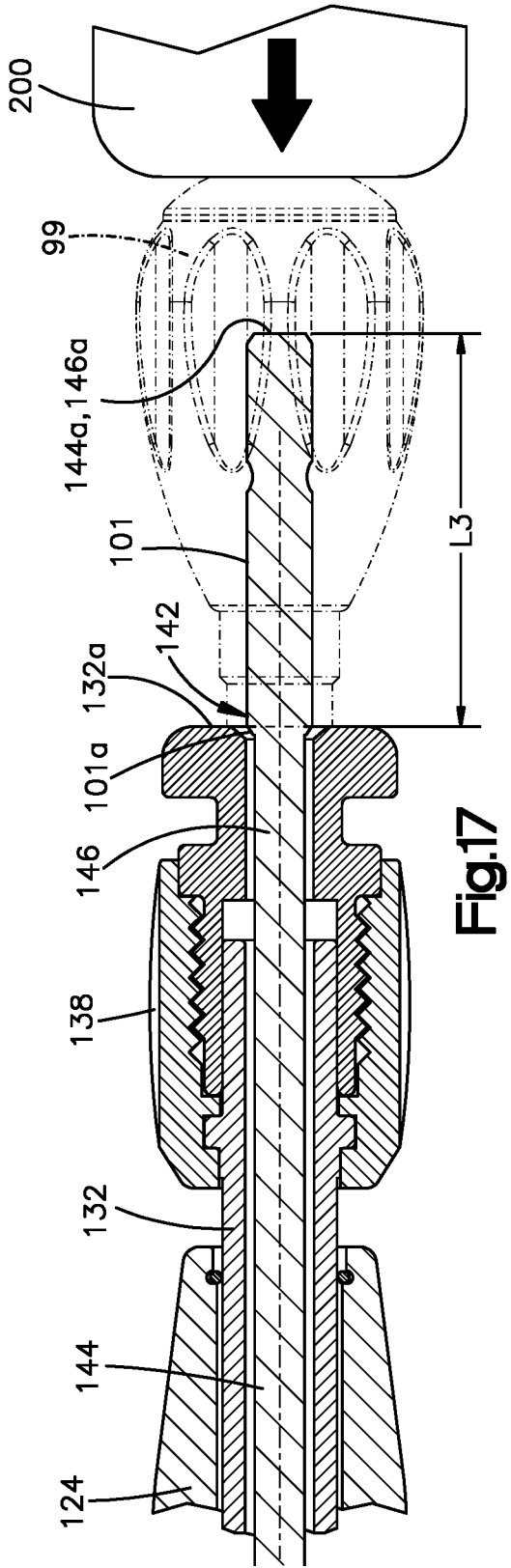

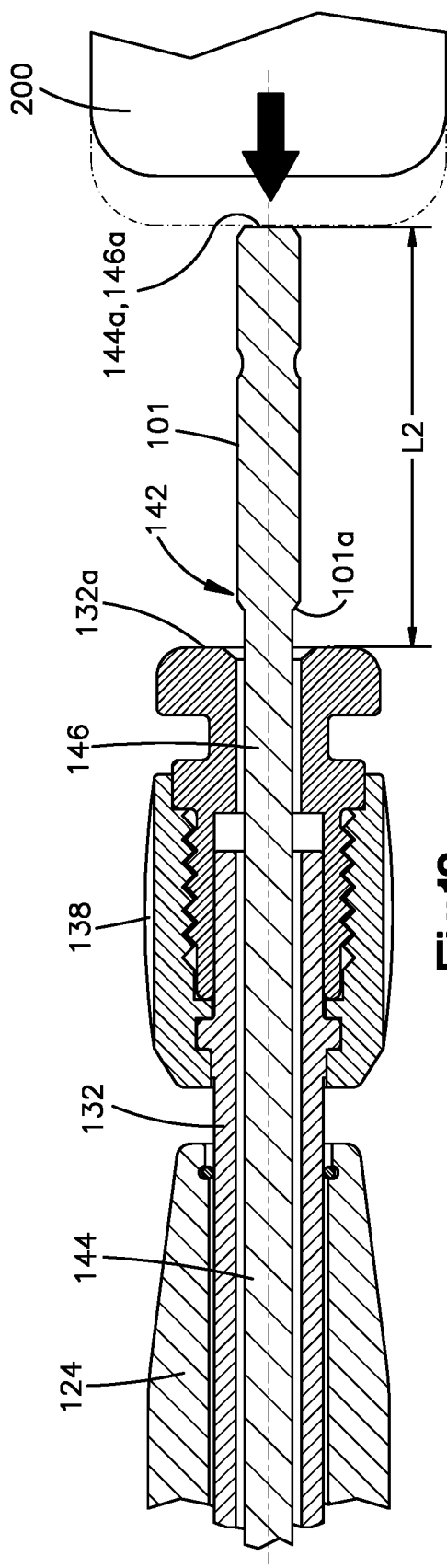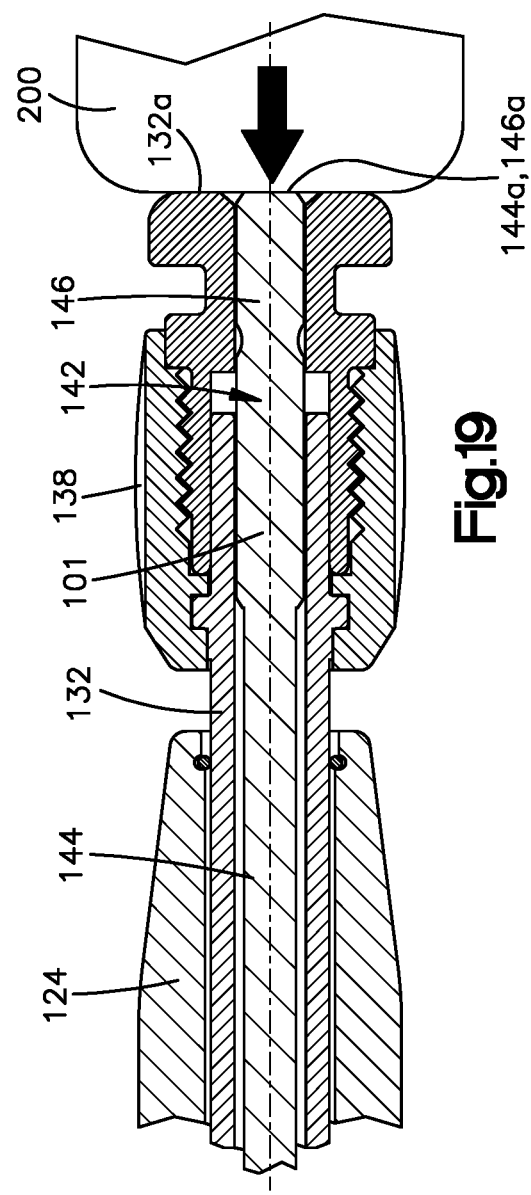
Fig.18
Fig.19

INTERVERTEBRAL IMPLANT INSERTER AND RELATED METHODS

CROSS-REFERENCE TO RELATED CASES

This application is a continuation-in-part of U.S. patent application Ser. No. 15/378,724, filed on Dec. 14, 2016, the teachings of all of which are hereby incorporated by reference as if set forth in their entirety herein.

TECHNICAL FIELD

The present invention relates to an expandable intervertebral implant, insertion instrument, system, kit, and method.

BACKGROUND

The human spine is comprised of a series of vertebral bodies separated by intervertebral discs. The natural intervertebral disc contains a jelly-like nucleus pulposus surrounded by a fibrous annulus fibrosus. Under an axial load, the nucleus pulposus compresses and radially transfers that load to the annulus fibrosus. The laminated nature of the annulus fibrosus provides it with a high tensile strength and so allows it to expand radially in response to this transferred load.

In a healthy intervertebral disc, cells within the nucleus pulposus produce an extracellular matrix (ECM) containing a high percentage of proteoglycans. These proteoglycans contain sulfated functional groups that retain water, thereby providing the nucleus pulposus within its cushioning qualities. These nucleus pulposus cells may also secrete small amounts of cytokines such as interleukin-1.beta. and TNF-.alpha. as well as matrix metalloproteinases ("MMPs"). These cytokines and MMPs help regulate the metabolism of the nucleus pulposus cells.

In some instances of disc degeneration disease (DDD), gradual degeneration of the intervetebral disc is caused by mechanical instabilities in other portions of the spine. In these instances, increased loads and pressures on the nucleus pulposus cause the cells within the disc (or invading macrophases) to emit larger than normal amounts of the above-mentioned cytokines. In other instances of DDD, genetic factors or apoptosis can also cause the cells within the nucleus pulposus to emit toxic amounts of these cytokines and MMPs. In some instances, the pumping action of the disc may malfunction (due to, for example, a decrease in the proteoglycan concentration within the nucleus pulposus), thereby retarding the flow of nutrients into the disc as well as the flow of waste products out of the disc. This reduced capacity to eliminate waste may result in the accumulation of high levels of toxins that may cause nerve irritation and pain.

As DDD progresses, toxic levels of the cytokines and MMPs present in the nucleus pulposus begin to degrade the extracellular matrix, in particular, the MMPs (as mediated by the cytokines) begin cleaving the water-retaining portions of the proteoglycans, thereby reducing its water-retaining capabilities. This degradation leads to a less flexible nucleus pulposus, and so changes the loading pattern within the disc, thereby possibly causing delamination of the annulus fibrosus. These changes cause more mechanical instability, thereby causing the cells to emit even more cytokines, thereby upregulating MMPs. As this destructive cascade continues and DDD further progresses, the disc begins to bulge ("a herniated disc"), and then ultimately ruptures, which may cause the nucleus pulposus to contact the spinal cord and produce pain.

One proposed method of managing these problems is to remove the problematic disc and replace it with a device that restores disc height and allows for bone growth between the adjacent vertebrae. These devices are commonly called fusion devices, or "interbody fusion devices". Current spinal fusion procedures include transforaminal lumbar interbody fusion (TLIF), posterior lumbar interbody fusion (PLIF), and extreme lateral interbody fusion (XLIF) procedures.

SUMMARY

According to one embodiment of the present disclosure, an insertion instrument is configured to implant an expandable intervertebral implant in an intervertebral space. The insertion instrument can include a drive shaft elongate along a longitudinal direction, and a drive member disposed at a distal end of the drive shaft. The drive member can be configured to 1) couple to a complementary driven member of the implant, and 2) iterate the intervertebral implant from a collapsed configuration to an expanded configuration. The insertion instrument can further include a securement member that is spaced from the drive member along a lateral direction that is perpendicular to the longitudinal direction, the securement member having at least one guide rail that has a height along a transverse direction sufficient to 1) reside in a corresponding at least one guide channel of the implant when the implant is in the collapsed configuration, 2) ride along the implant in the at least one guide channel as the implant expands to the expanded configuration, and 3) remain in the corresponding at least one guide channel when the implant is in the expanded configuration. The transverse direction is perpendicular to each of the longitudinal direction and the lateral direction.

According to another embodiment, an insertion instrument is configured to implant an expandable intervertebral implant in an intervertebral space. The insertion instrument can include a securement member configured to couple to both an inferior endplate and a superior endplate of the implant, and an engagement member configured to couple to the securement member. Further, the insertion instrument can include a driver having a drive shaft and a drive member disposed at a distal end of the drive shaft. The drive shaft can be elongate along a longitudinal direction and configured to be received by the engagement member. The drive member can be configured to 1) couple to a complementary driven member of the implant, and 2) iterate the intervertebral implant from a collapsed configuration to an expanded configuration. The drive shaft can be configured such that, when an impaction force is applied by an impaction instrument to a proximal end of the drive shaft, opposite the distal end, the impaction force causes the drive shaft to move from an extended configuration, wherein a proximal end of the drive shaft extends out of the engagement member in a proximal direction, to a retracted configuration, wherein the proximal end of the drive shaft is retracted into the engagement member, so that the impaction force is applied to the engagement member.

BRIEF DESCRIPTION OF THE DRAWINGS

The foregoing summary, as well as the following detailed description of illustrative embodiments of the intervertebral implant of the present application, will be better understood when read in conjunction with the appended drawings. For the purposes of illustrating aspects of the present disclosure, there is shown in the drawings illustrative embodiments. It should be understood, however, that the disclosure is not limited to the precise arrangements and instrumentalities shown. In the drawings:

FIG. 4A is a side elevation view of an intervertebral implant system including the expandable implant of FIG. 1 and an insertion instrument configured to secure to and actuate the expandable implant;

FIG. 4B is a perspective view of the insertion instrument of FIG. 4A;

FIG. 4C is an exploded side elevation view of the insertion instrument of FIG. 4B;

FIG. 5A is a sectional plan view of the insertion instrument aligned for securement with the expandable implant;

FIG. 5B is an enlarged sectional plan view of a portion of the insertion instrument and the expandable implant of FIG. 5A, taken at Region 5B;

FIG. 6A is a sectional plan view similar to FIG. 5A, but showing the insertion instrument attached to the expandable implant;

FIG. 6B is an enlarged sectional plan view of a portion of the insertion instrument and the expandable implant of FIG. 6A, taken at Region 6B;

FIG. 8A is a sectional plan view similar to FIG. 7A, but showing a drive member of the insertion instrument rotationally coupled to a driven member of the expandable implant;

FIG. 8B is an enlarged perspective view showing the insertion instrument secured to the expandable implant with the drive member of the insertion instrument coupled to the driven member of the expandable implant as illustrated in FIG. 7A, showing the implant in a collapsed configuration;

FIG. 9A is a sectional plan view similar to FIG. 8A, but after the insertion instrument has driven the implant to expand from the collapsed configuration to the expanded configuration;

FIG. 9B is an enlarged sectional plan view of a portion of the insertion instrument and the expandable implant of FIG. 9A, taken at Region 9B;

FIG. 9C is a perspective view of a portion of the instrument and expandable implant of FIG. 9A;

FIG. 10A is a sectional plan view similar to FIG. 9A, but showing the drive member of the insertion instrument decoupled from the driven member of the expandable implant;

FIG. 10B is an enlarged sectional plan view of a portion of the insertion instrument and the expandable implant of FIG. 10A, taken at Region 10B;

FIG. 16 is a sectional plan view of a proximal portion of the insertion instrument of FIG. 13 with the driver extended according to one embodiment;

FIG. 17 is a sectional plan view of a proximal portion of the insertion instrument of FIG. 13 with the driver retracted according to the embodiment of FIG. 16;

FIG. 18 is a sectional plan view of a proximal portion of the insertion instrument of FIG. 13 with the driver extended according to another embodiment; and FIG. 19 is a sectional plan view of a proximal portion of the insertion instrument of FIG. 13 with the driver retracted according to the embodiment of FIG. 18.

DETAILED DESCRIPTION OF ILLUSTRATIVE EMBODIMENTS

Figure 1:
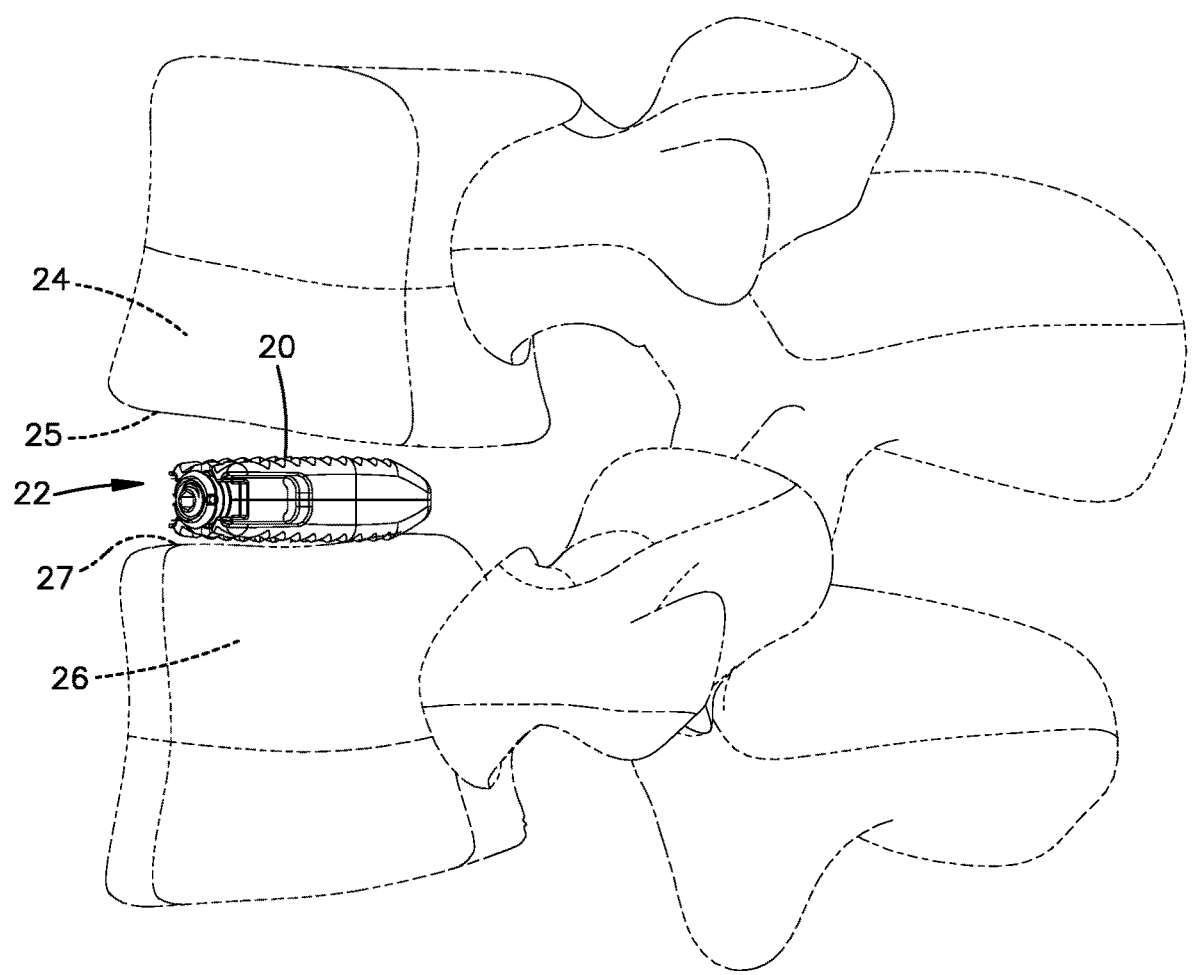
FIG. 1 is a perspective view of an expandable implant shown implanted in an intervertebral disc space, showing the implant in a collapsed position.
Figure 2A:
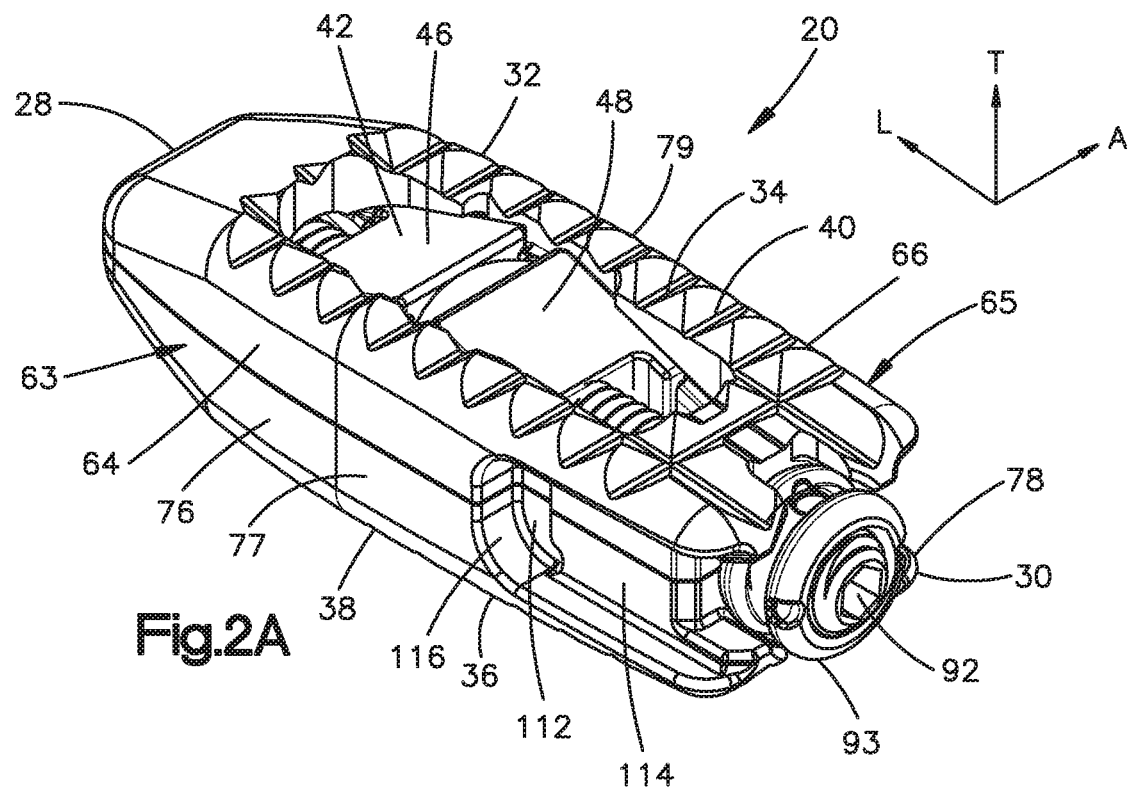
FIG. 2A is a perspective view of the expandable implant of FIG. 1.
Figure 2B:
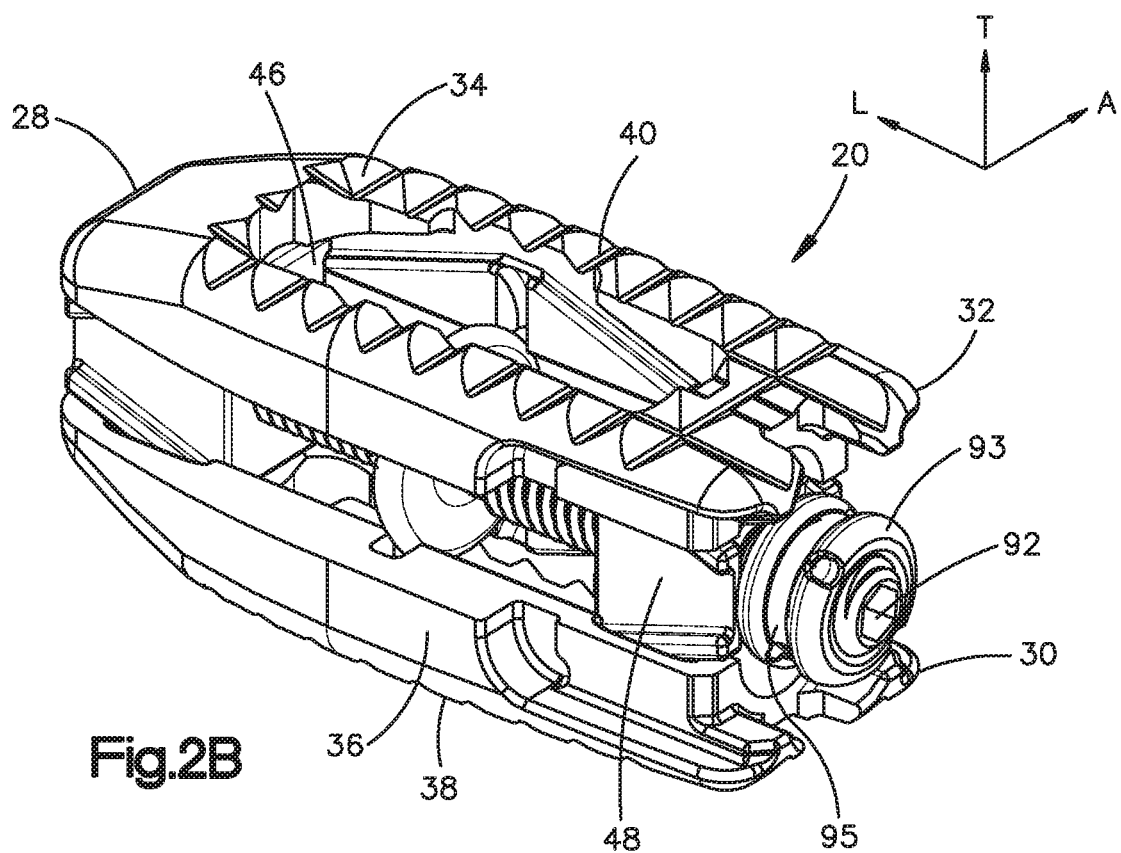
FIG. 2B is a perspective view of the expandable implant of FIG. 2A, but shown in an expanded configuration.
Figure 3:
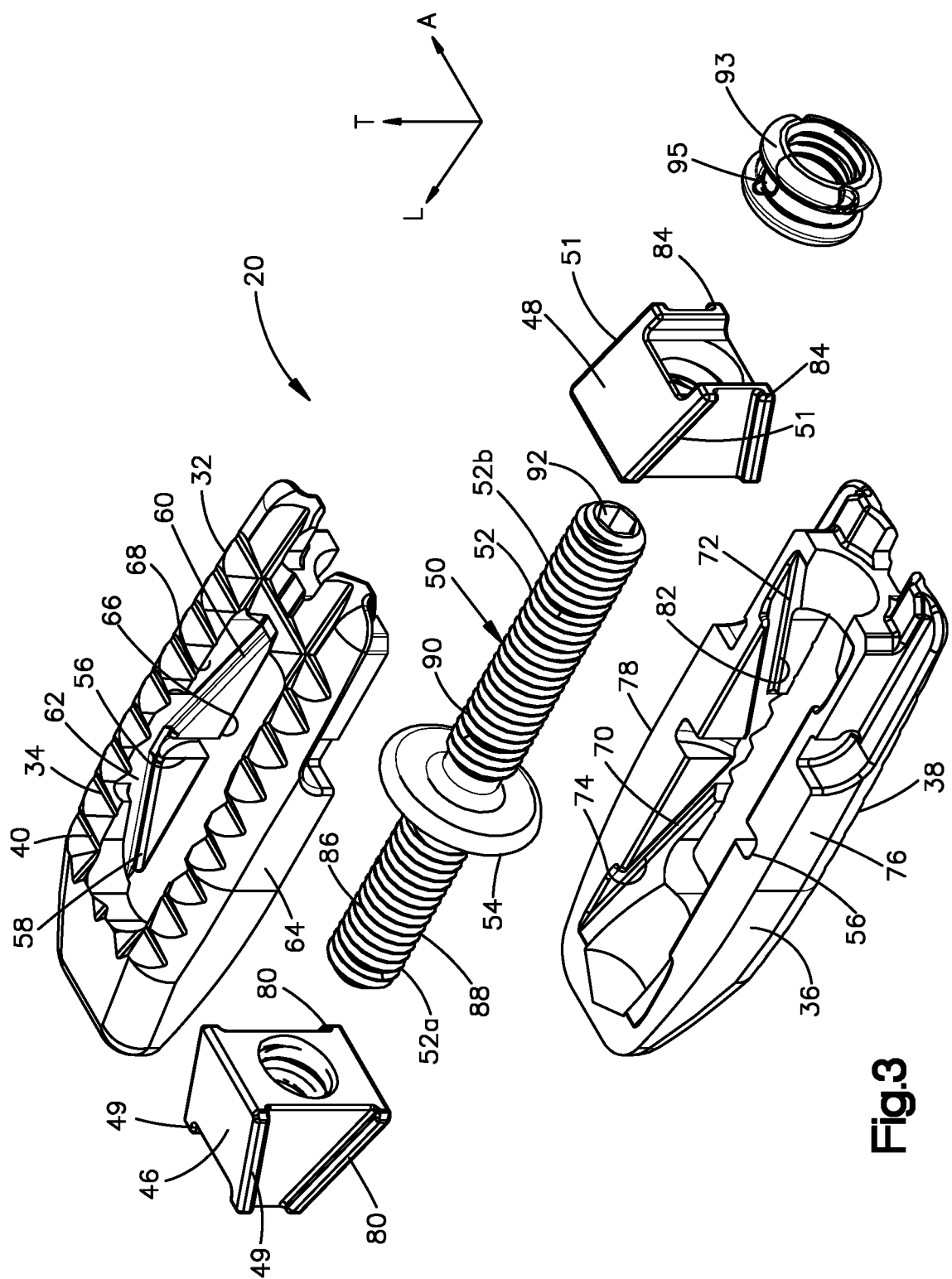
FIG. 3 is an exploded perspective view of the expandable implant of FIG. 2A.

Referring initially to FIGS. 1-3, an expandable intervertebral implant 20 is configured for implantation in an intervertebral space 22 that is defined between a first or superior vertebral body 24 and a second or inferior vertebral body 26. The vertebral bodies 24 and 26 can be anatomically adjacent each other, or can be remaining vertebral bodies after a corpectomy procedure has removed a vertebral body from a location between the vertebral bodies 24 and 26. The intervertebral space 22 in FIG. 1 is illustrated after a discectomy, whereby the disc material has been removed or at least partially removed from the intervertebral space 22 to prepare the intervertebral space 22 to receive the intervertebral implant 20.

Figure 4D:
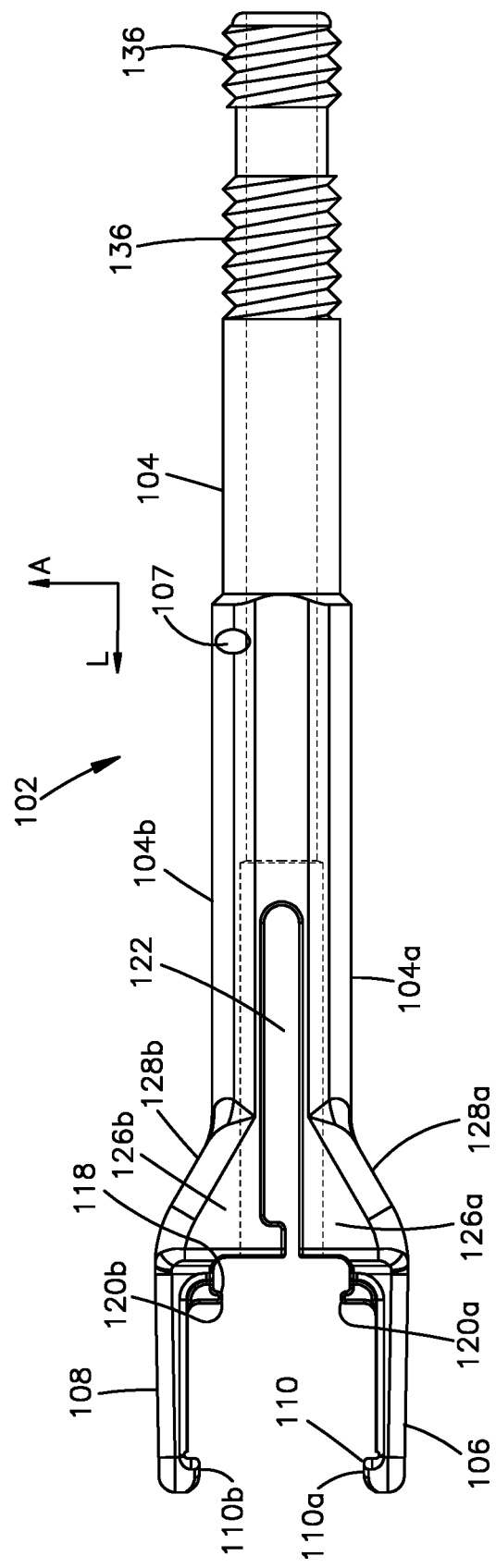
FIG. 4D is an enlarged top plan view of a securement member of the insertion instrument of FIG. 4B.
Figure 4E:
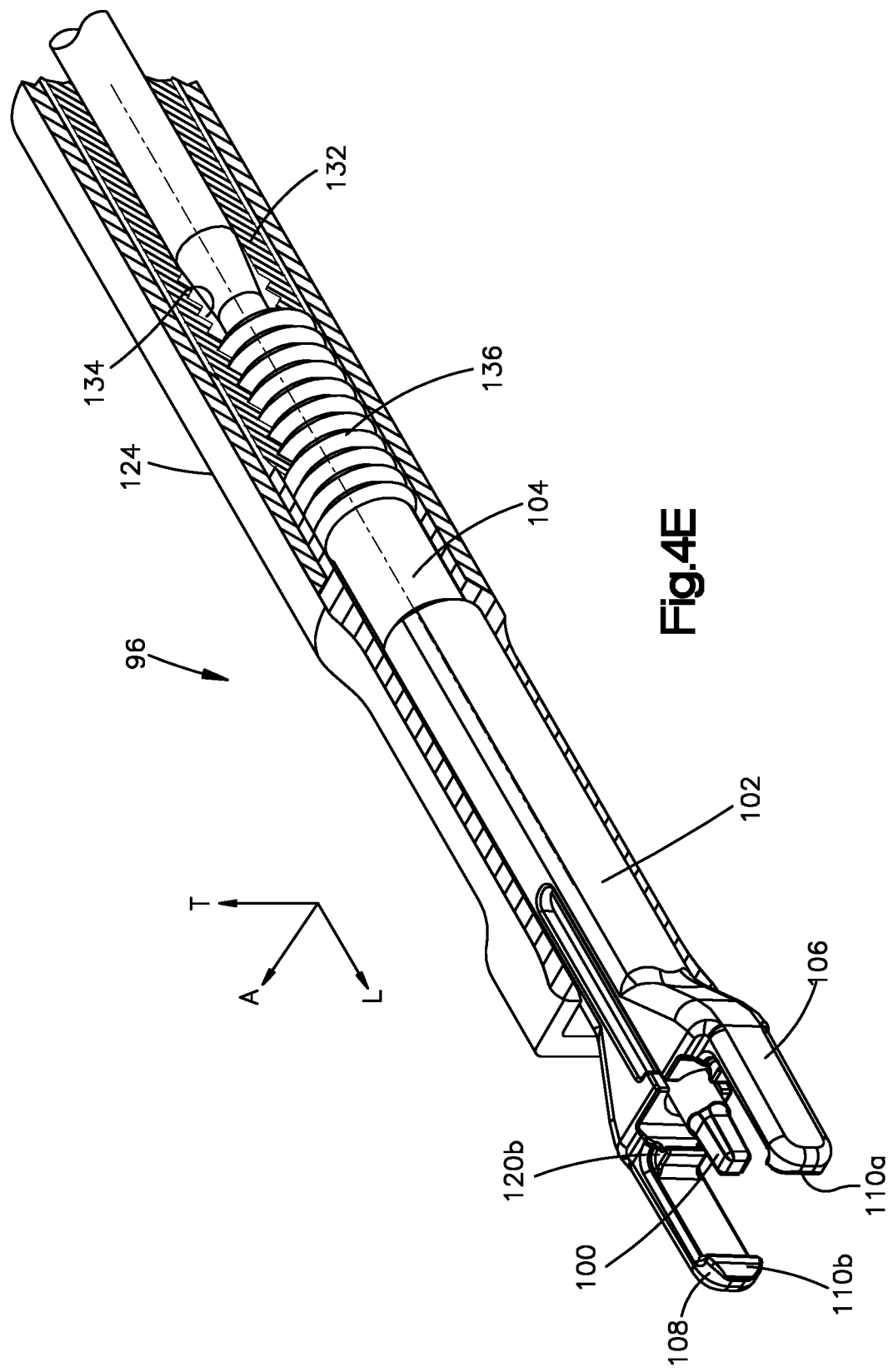
FIG. 4E is an enlarged partial cut-away perspective view of a portion of the insertion instrument illustrated in FIG. 4C.

The intervertebral implant 20 defines a distal or leading end 28 and a proximal or trailing end 30 opposite the leading end 28 along a longitudinal direction L. As used herein, the term "distal" and derivatives thereof refer to a direction from the trailing end 30 toward the leading end 28. As used herein, the term "proximal" and derivatives thereof refer to a direction from the leading end 28 toward the trailing end 30. The distal and proximal directions can be oriented along the longitudinal direction L. The leading end 28 can also be referred to as an insertion end with respect to the direction of insertion of the implant 20 into the intervertebral space 22. Thus, the longitudinal direction L can define an insertion direction into the intervertebral space 22. The leading end 28 is spaced from the trailing end 30 in the insertion direction. In this regard, the insertion direction can be defined by the distal direction. In one example, the leading end 28 can be tapered and configured for insertion into the intervertebral space 22 between the first and second vertebral bodies 24 and 26. As will be described in more detail below, the trailing end 30 is configured to couple to an insertion instrument 96 shown in FIG. 4, which is configured to rigidly support and deliver the implant 20 into the intervertebral space 22, and iterate the implant 20 from a collapsed configuration shown in FIG. 2A to an expanded configuration shown in FIG. 2B. The implant 20 has a first height when in the collapsed configuration, and defines a second height when in the expanded configuration that is greater than the first height.

The intervertebral implant 20 includes a first or superior endplate 32 that defines a first or superior vertebral engagement surface 34 that is configured to abut the superior vertebral body 24, and a second or inferior endplate 36 that defines a second or inferior vertebral engagement surface 38 that is configured to abut the inferior vertebral body 26. In particular, the first and second endplates 32 and 36 of the implant 20 are configured to abut respective first and second vertebral endplates 25 and 27, respectively, of the superior and inferior vertebral bodies 24 and 26. The first and second vertebral endplates 25 and 27 can also be referred to as superior and inferior vertebral endplates 25 and 27, respectively. As used herein, the term "superior" and "up" and derivatives thereof refer to a direction from the second vertebral engagement surface 38 toward the first vertebral engagement surface 34. As used herein, the term "inferior" and "down" and derivatives thereof refer to a direction from the first vertebral engagement surface 34 toward the second vertebral engagement surface 38. The superior and inferior directions can be oriented along a transverse direction T. The first and second endplates 32 and 36, and thus the first and second vertebral engagement surfaces 34 and 38 are spaced from each other along the transverse direction T. The transverse direction T is oriented substantially perpendicular to the longitudinal direction L. In one example, the first and second endplates 32 and 36 can be configured to grip the first and second vertebral bodies, respectively. In one example, the first and second endplates 32 and 36 can have teeth 40 that project out from the vertebral engagement surfaces 34 and 38. The teeth 40 are configured to grip the superior and inferior vertebral bodies 24 and 26, respectively. In particular, the teeth 40 are configured to grip the superior and inferior vertebral endplates 25 and 27, respectively.

The intervertebral implant 20 is expandable from a collapsed position shown in FIG. 2A to an expanded position shown in FIG. 2B. Thus, the intervertebral implant 20 is configured to be inserted into the intervertebral disc space 22 in the collapsed configuration. The implant 20 is configured to be expanded from the collapsed configuration to the expanded configuration after the implant 20 has been implanted into the intervertebral space 22. Thus, a method can include the step of inserting the implant 20 into the intervertebral space 22 in a collapsed position, and subsequently iterating the implant 20 to the expanded position such that the first and second vertebral engagement surfaces 34 and 38 bear against the first and second vertebral endplates 25 and 27, respectively.

When the intervertebral implant 20 is in the collapsed configuration, the first and second vertebral engagement surfaces 34 and 38 are spaced apart a first distance along the transverse direction T. The first and second endplates 32 and 36 move apart from each other along the transverse direction T as the implant 20 moves from the collapsed configuration to the expanded configuration. In one example, respective entireties of the first and second endplates 32 and 36 are configured to move away from each other as the implant 20 expends from the collapsed position to the expanded position. When the intervertebral implant 20 is in the expanded configuration, the first and second vertebral engagement surfaces 34 and 38 are spaced apart a second distance along the transverse direction T that is greater than the first distance. Thus, the implant 20 is configured to impart appropriate height restoration to the intervertebral space 22. It should be appreciated that the implant 20 is configured to remain in the expanded configuration in the presence of compressive anatomical forces after implantation, and that the implant 20 is prevented from moving toward the collapsed position in response to the compressive anatomical forces. The intervertebral space 22 that receives the implant 20 can be disposed anywhere along the spine as desired, including at the lumbar, thoracic, and cervical regions of the spine.

Referring now also to FIG. 3, the intervertebral implant 20 further includes at least one expansion member 42 that is configured to move between first and second positions that iterate the implant 20 between the collapsed configuration and the expanded configuration. The at least one expansion member 42 can include a first wedge member 46 and a second wedge member 48. The first and second wedge members 46 and 48 can be configured to couple the first and second endplates 32 and 36 to each other. The first and second wedge members 46 and 48 are translatable in a first direction along the longitudinal direction L so as to cause the first and second endplates 32 and 36 to move away from each other, thereby expanding the implant 20. The first and second wedge members 46 and 48 are translatable in a second direction along the longitudinal direction L opposite the first direction so as to cause the first and second endplates 32 and 36 to move toward from each other, thereby collapsing the implant 20.

The implant 20 can further include an actuator 50 coupled to the first and second wedge members 46 and 48. The actuator 50 includes a threaded actuator shaft 52 and an actuation flange 54 that protrudes from the actuator shaft 52. The actuation flange 54 fits into respective complementary slots 56 of the first and second endplates 32 and 36 so as to prevent the actuator 50 from translating relative to the endplates 32 and 36 along the longitudinal direction L.

The first endplate 32 defines first and second ramp surfaces 58 and 60 that are opposite the first vertebral engagement surface 34 along the transverse direction T. The first ramp surface 58 is angled in the superior direction as it extends in the proximal direction toward the second ramp surface 60. The second ramp surface 60 is angled in the superior direction as it extends in the distal direction toward the first ramp surface 58. The first wedge member 46 is configured to ride along the first ramp surface 58. Similarly, the second wedge member 48 is configured to ride along the second ramp surface 60.

The first ramp surface 58 can partially define a first ramped slot 62 in first and second side walls 64 and 66 of the first endplate 32 that are opposite each other along a lateral direction A that is perpendicular to each of the longitudinal direction L and the transverse direction T. The first wedge member 46 can define first upper rails 49 that are configured to ride in the first ramped slots 62. Thus, the first upper rails 49 are configured to ride along the first ramp surface 58. Similarly, the second ramp surface 60 can partially define a second ramped slot 68 in the first and second side walls 64 and 66. The second wedge member 48 can define second upper rails 51 that are configured to ride in the second ramped slots 68. Thus, the second upper rails 51 are configured to ride along the second ramp surface 60.

Similarly, the second endplate 36 defines first and second ramp surfaces 70 and 72 that are opposite the second vertebral engagement surface 38 along the transverse direction T. The first ramp surface 70 is angled in the inferior direction as it extends in the proximal direction toward the second ramp surface 72. The second ramp surface 72 is angled in the inferior direction as it extends in the distal direction toward the first ramp surface 70. The first wedge member 46 is configured to ride along the first ramp surface 70. Similarly, the second wedge member 48 is configured to ride along the second ramp surface 72.

The first ramp surface 70 can partially define a first ramped slot 74 in first and second side walls 76 and 78 of the second endplate 36 that are opposite each other along the lateral direction A. The first wedge member 46 can define first lower rails 80 that are configured to ride in the first ramped slots 74. Thus, the first lower rails 80 are configured to ride along the first ramp surface 70. Similarly, the second ramp surface 72 can partially define a second ramped slot 82 in the first and second side walls 76 and 78. The first side walls 64 and 76 can cooperate to define a first side 77 of the implant 20, and the second side walls 66 and 78 can cooperate to define a second side 79 of the implant 20. The second wedge member 48 can define second lower rails 84 that are configured to ride in the second ramped slots 82. Thus, the second lower rails 84 are configured to ride along the second ramp surface 72.

As the first and second wedge members 46 and 48 move in a first expansion direction, the first and second wedge members 46 and 48 push the first and second endplates 32 and 36 away from each other along the transverse direction T, thereby causing the implant 20 to expand along the transverse direction T. As the first and second wedge members 46 and 48 move in a second collapsing direction opposite the first expansion direction, the first and second wedge members 46 and 48 can draw the first and second endplates 32 and 36 toward each other along the transverse direction T, thereby collapsing the implant to collapse along the transverse direction T. The first expansion direction of the first and second wedge members 46 and 48 can be defined by movement of the first and second wedge members 46 and 48 toward each other. The second collapsing direction of the first and second wedge members 46 and 48 can be defined by movement of the first and second wedge members 46 and 48 away from each other. It should be appreciated, of course, that the implant can alternatively be constructed such that the first expansion direction of the first and second wedge members 46 and 48 can be defined by movement of the first and second wedge members 46 and 48 away each other, and the second collapsing direction of the first and second wedge members 46 and 48 can be defined by movement of the first and second wedge members 46 and 48 toward from each other.

With continuing reference to FIGS. 2A-3, the actuator 50 is configured to cause the first and second wedge members 46 and 48 to move in the first expansion direction. Further, the actuator 50 can be configured to cause the first and second wedge members 46 and 48 to move in the second collapsing direction. In particular, the actuator shaft 52 can be threaded so as to threadedly mate with the first and second wedge members 46 and 48, respectively. In one example, the actuator shaft 52 can define exterior threads 86. The actuation flange 54 can divide the actuator shaft 52 into a first or distal shaft section 52a and a second or proximal shaft section 52b.

The threads 86 can include a first threaded portion 88 that extends along the distal shaft section 52a, and a second threaded portion 90 that extends along the proximal shaft section 52b. The first wedge member 46 can include internal threads that are threadedly mated to the distal shaft section 52a. The second wedge member 48 can include internal threads that are threadedly mated to the proximal shaft section 52b. The first and second threaded portions 88 and 90 have respective thread patterns, respectively that are oriented in opposite directions. Accordingly, rotation of the actuator 50 in a first direction of rotation drives the wedge members 46 and 48 to threadedly travel away from each other along the actuator shaft 52. The actuator shaft 52 can be oriented along the longitudinal direction L. Thus, rotation of the actuator 50 in the first direction can cause the wedge members 46 and 48 to move in the expansion direction. Rotation of the actuator 50 in a second direction of rotation opposite the first direction of rotation drives the wedge members 46 and 48 to threadedly travel toward each other along the actuator shaft 52. Thus, rotation of the actuator 50 in the second direction can cause the wedge members 46 and 48 to move in the collapsing direction. The first and second directions of rotation can be about the central axis of the actuator shaft 52, which can be oriented along the longitudinal direction L.

The actuator 50, and thus the implant 20, can further include a driven member 92 that is rotationally fixed to the actuator shaft 52, such that a rotational force applied to the driven member 92 drives the actuator shaft 52, and thus the actuator 50, to rotate. The driven member 92 can be monolithic with the actuator shaft 52, and in one example can be defined by the actuator shaft 52. For instance, the driven member 92 can be configured as a socket that extends distally into the proximal end of the actuator shaft 52. Alternatively, the driven member 92 can be attached to the actuator shaft 52. The driven member 92 can be configured to couple to the insertion instrument 96 so as to receive a drive force that causes the actuator shaft 52, and thus the actuator 50, to rotate. In one embodiment, the driven member 92 can define a socket that is configured to receive a drive member of the insertion instrument 96. Alternatively, the driven member 92 can be configured to be received by the drive member.

The actuator 50, and thus the implant 20, can further include an implant coupler 93 that is supported by the driven member 92. In particular, the implant coupler 93 can be supported by the actuator shaft 52. The implant coupler 93 can be monolithic with the actuator shaft 52, or can be secured to the actuator shaft 52. For instance, the implant coupler 93 can be threadedly attached to the actuator shaft 52. In one example, the implant coupler 93 can be aligned with the driven member 92 along a plane that includes the lateral direction A and the transverse direction T. The implant coupler 93 can be configured to attach to a complementary attachment member of the insertion instrument 96. For instance, the implant coupler 93 can define an external groove 95 that is configured to receive the attachment member of the insertion instrument 96. The implant coupler 93 can be configured as a ring, or can be configured as any suitable alternatively constructed attachment member as desired. Aspects of the implant 20 are further described in U.S. patent application Ser. No. 14/640,264 filed Mar. 6, 2015, the disclosure of which is hereby incorporated by reference as if set forth in its entirety herein.

Referring to FIG. 4A-4B, an intervertebral implant system 94 can include the intervertebral implant 20 and an insertion instrument 96. The insertion instrument 96 can be configured to implant the expandable intervertebral implant 20 in the intervertebral space. For instance, the insertion instrument 96 can be configured to removably attach and further secure to the implant 20 so as to define a rigid construct with the implant 20. The insertion instrument can further be configured to apply an actuation force to the actuator 50 that drives the actuator to rotate. For instance, the insertion instrument 96 can drive the actuator 50 to selectively rotate in the first direction of rotation and in the second direction of rotation.

Thus, a method can include the step of attaching the insertion instrument 96 to the intervertebral implant 20 to form a rigid construct. The implant 20 can initially be in the collapsed configuration when the insertion instrument 96 is coupled to the implant 20. Alternatively, the insertion instrument 96 can move the implant 20 to the collapsed position. The method can further include the step of actuating the drive member to rotate the actuator 50 of the implant 20 in the first direction of rotation, thereby causing the implant 20 to expand in the manner described above to a desired height. Once the implant 20 has achieved the desired height, the method can include the step of removing the insertion instrument 96 from the implant 20.

Referring now also to FIGS. 2A-3 and 4C-4E, the insertion instrument 96 can include a driver 97 that has a drive shaft 98 and a drive member 100. The driver 97 can further include a knob 99. The drive shaft 98 has a proximal end 98a and a distal end 98b spaced from one another along the longitudinal direction L. The drive shaft 98 is elongate along the longitudinal direction L from the proximal end 98a to the distal end 98b. The drive shaft 98 can include an engagement feature 101 at its proximal end 98a that is configured to couple to an engagement feature 103 of the knob 99 such that the knob 99 can be gripped and rotated, to thereby rotate the drive shaft 98 about a longitudinal axis of rotation. In one example, the engagement feature 101 of the drive shaft 98 can include an outer surface having a non-circular cross section and the engagement feature 103 of the knob 99 can define a socket having a non-circular cross section. Accordingly, when the drive shaft 98 is inserted into the socket, rotation of the knob 99 causes the drive shaft 98 to correspondingly rotate. Alternatively, the knob 99 can be monolithic with the drive shaft 98.

The drive member 100 can be disposed at the distal end 98b of the drive shaft 98. The drive member 100 can be monolithic with the drive shaft 98 or attached to the drive shaft 98. The drive member 100 is configured to couple to the driven member 92 (see FIG. 3). For instance, the drive member 100 and the socket defined by the driven member 92 can have a non-circular cross section. Accordingly, when the drive member 100 is inserted into the socket, rotation of the drive member 100 causes the actuator shaft 52 of the implant 20 to correspondingly rotate. Thus, it should be appreciated that rotation of the drive member 100 in the first direction of rotation causes the actuator 50 of the implant 20 to rotate in the first direction of rotation. Thus, the drive member 100 of the insertion instrument 96 can be configured to couple to the complementary driven member 92 of the implant 20, and iterate the intervertebral implant 20 from the collapsed configuration to the expanded configuration. Similarly, rotation of the drive member 100 in the second direction of rotation causes the actuator 50 of the implant 20 to rotate in the second direction of rotation. Thus, the drive member 100 can further iterate the intervertebral implant 20 from the expanded configuration to the collapsed configuration. As will be appreciated from the description below, the drive member 100 can be translated along the longitudinal direction between an extended position whereby the drive member 100 is positioned to be coupled to the driven member 92 when the insertion instrument 96 is attached to the implant 20, and a retracted position whereby the drive member 100 is removed from the driven member 92 when the insertion instrument 96 is attached to the implant 20.

The insertion instrument 96 can further include a securement member 102 that is configured to attach and secure to the implant 20. In particular, the securement member 102 is configured to iterate between an engaged configuration and a disengaged configuration. The securement member 102 is configured to attach to the implant 20 when in the disengaged configuration, and is secured to the implant 20 when in the engaged configuration. The securement member 102 is further configured to be removed from the implant 20 when in the disengaged configuration. The securement member 102 is configured to be prevented from removal from the implant 20 when the securement member 102 is in the engaged configuration, and thus when the securement member 102 is secured to the implant 20.

The securement member 102 can include a securement shaft 104 and a securement end 105 that extends distally from the securement shaft 104. The securement end 105 can include first and second securement plates 106 and 108 that extend from the securement shaft 104 in the distal direction. The first and second securement plates 106 and 108 can be spaced from each other along a direction perpendicular to the longitudinal direction L. For instance, the first and second securement plates 106 and 108 can be spaced from each other along the lateral direction A. The first and second securement plates 106 and 108 can be oriented parallel to each other. The first and second securement plates 106 and 108 can be positioned such that the drive member 100 extends between the first and second securement plates 106 and 108 along the lateral direction A. Further, the drive member 100 can be aligned with the first and second securement plates 106 and 108 along the lateral direction A.

The securement member 102 can further include at least one projection that can define at least one guide rail 110 that projects from a corresponding one of the first and second securement plates 106 and 108 toward the other of the first and second securement plates 106 and 108. The at least one guide rail is configured to slide along a respective at least one pair of side walls of the implant. The at least one pair can include a first pair 63 (see FIG. 2A) defined by the side walls 64 and 76 of the implant 20, and a second pair 65 (see FIG. 2A) defined by the side walls 66 and 78 of the implant 20. The implant 20 can define a first side 77 and a second side 79 that is opposite the first side 77 with respect to the lateral direction A. The first side 77 can be defined by the side walls 64 and 76 of the first pair 63. The second side 79 can be defined by the side walls 66 and 78 of the second pair 65. The first and second sides 77 and 79 are opposite each other along the lateral direction A. The side walls of each pair can be aligned with each other along the transverse direction T. Further, the side walls of each pair can abut each other when the implant is in the collapsed configuration.

The implant 20 can include at least one guide channel 112 that is defined by an outer surface of each of the pair of side walls of the implant 20. The at least one guide channel 112 is configured to receive the at least one first guide rail 110, such that the at least one guide rail 110 resides in the at least one guide channel 112 when the insertion instrument 96 is secured to the implant 20. The at least one guide rail 110 can also reside in the at least one guide channel 112 when the insertion instrument 96 is attached, but not secured, to the implant 20. The at least one guide rail 110 can have a height along the transverse direction T that is sufficient to 1) reside in the at least one guide channel 112 when the implant 20 is in the collapsed configuration, 2) ride along the implant 20 in the at least one guide channel 112 as the implant 20 expands to the expanded configuration, and 3) remain in the corresponding at least one guide channel 112 when the implant 20 is in the expanded configuration.

In one example, the securement member 102 can include a first guide rail 110a that projects from the first securement plate 106 toward the second securement plate 108, and a second guide rail 110b that projects from the second securement plate 108 toward the first securement plate 106. Thus, the first and second guide rails 110a and 110b can be spaced from each other along the lateral direction A, and can be inwardly facing. Further, the first and second guide rails 110a and 110b can be aligned with each other along the lateral direction A. The implant 20 can include a guide channel 112 that is defined by the outer surface of each of the first and second pairs 63 and 65 of side walls (see first and second guide channels 112 in FIG. 5B). Thus, the side walls 64 and 76 can each define a portion of a first guide channel 112. The side walls 66 and 78 can further define a portion of a second guide channel. The guide channel 112 of the first pair 63 of side walls is sized to receive the first guide rail 110a, and the guide channel 112 of the second pair 65 of side walls is sized to receive the second guide rail 110b.

The outer surface of the side walls of each of the first and second pairs 63 and 65 of side walls can further cooperate to define respective lead-in recesses 114 to the guide channel 112 (see first and second lead-in recesses 114 in FIG. 5B). The respective lead-in recess 114 is spaced in the proximal direction from the guide channel 112. For instance, each of the side walls of the implant 20 defines a corresponding portion of the respective lead-in recess. The respective endplates 32 and 36 can terminate the lead-in recesses 114 and the guide channels 112 along the transverse direction T. The guide channels 112 have a depth in the lateral direction A that is greater than the depth of the lead-in recesses 114 in the lateral direction A. As will be described in more detail below, the first and second guide rails 110a and 110b are configured to ride distally along the outer surface of the implant 20 in the respective lead-in recesses 114 and into the guide channels 112 when the insertion instrument 96 is in the disengaged configuration.

Because the securement plates 106 and 108 are resiliently supported by the securement shaft 104, and in particular by the first and second securement plates 106 and 108 respectively, and because the guide channels 112 are deeper than the lead-in recesses 114, the first and second guide rails 110a and 110b can resiliently move apart along the lateral direction as they cam over the implant 20, and can snap into the guide channels 112.

The distal end of the guide channels 112 can be defined by respective shoulders 116 that are defined by the respective side walls. The shoulders can protrude laterally outward with respect to the outer surface of the side walls at the lead-in recesses 114. Thus, the implant 20 defines a width along the lateral direction A at the guide channels 112 that is less than the width at the lead-in recesses 114. The width of the implant 20 at the lead-in recesses 114 is less than the width at the shoulders 116. The shoulders 116 provide stop surfaces configured to abut the guide rails 110a and 110b so as to prevent the guide rails 110a and 110b from traveling distally past the guide channels 112.

The first and second securement plates 106 and 108 define a height along the transverse direction T that is less than the height of the lead-in recesses 114 along the transverse direction T, both when the implant 20 is in the collapsed configuration and when the implant 20 is in the expanded configuration. Accordingly, the first and second securement plates 106 and 108 can reside in the lead-in recesses 114 when the first and second guide rails 110a and 110b are disposed in the respective guide channels 112. Further, in one example, the securement plates 106 and 108 have a width that is no greater than the depth of the lead-in recesses 114 with respect to the shoulders 116. Thus, the securement plates 106 and 108 can nest in the respective lead-in recesses 114. It is also appreciated in one example that the securement plates 106 and 108 are no wider along the lateral direction A, and no taller in the transverse direction T, than the intervertebral implant 20 when the implant 20 is in the collapsed configuration.

Further, the height of the first and second securement plates 106 and 108 can be greater than the distance between the respective pairs of side walls when the implant 20 is in the expanded configuration. Thus, the first and second guide rails 110a and 110b can remain inserted in the respective guide channels 112 when the implant 20 is in the expanded position. In one example, the first and second guide rails 110a and 110b can extend along respective entireties of the heights of the first and second securement plates 106 and 108, respectively. Alternatively, the first and second guide rails 110a and 110b can extend along respective portions less than the entireties of the heights of the first and second securement plates 106 and 108, respectively. In one example, the first and second guide rails 110a and 110b can have a height along the transverse direction T of between approximately 3 mm to approximately 7 mm, depending on the height of the intervertebral implant 20. In one narrow example, the height of the guide rails can be between approximately 3.7 mm and approximately 4 mm. As used herein, the terms "approximate" and "substantial" and derivatives thereof are used to account for variations in size and/or shape, such as may occur due to manufacturing tolerances and other factors.

The insertion instrument 96 can further include at least one instrument coupler 118 that is configured to attach to the implant coupler 93. For instance, the securement member 102 can include the at least one instrument coupler 118 that is configured to attach to the implant coupler 93 when the securement member 102 is in the disengaged configuration, and secure to the implant coupler 93 when the securement member 102 is in the engaged configuration. The at least one instrument coupler 118 can project from a corresponding one of the first and second securement plates 106 and 108 toward the other of the first and second securement plates 106 and 108. The at least one instrument coupler 118 is configured to be inserted into the external groove 95 of the implant coupler 93. For instance, the at least one attachment member can be configured to seat against the implant coupler 93 in the external groove 95 when the securement member 102 is in the engaged configuration.

The at least one instrument coupler 118 can be configured as a first collar 120a that projects from the first securement plate 106 toward the second securement plate 108, and a second collar 120b that projects from the second securement plate 108 toward the first securement plate 106. Each of the first and second collars 120a and 120b are configured to be inserted into the external groove 95 of the implant coupler 93 when the securement member 102 is in the disengaged configuration, and secured to the implant coupler 93 in the external groove 95 when the securement member 102 is in the engaged configuration. In particular, the first and second collars 120a and 120b can cam over the implant coupler 93 and snap into the groove 95 as the insertion instrument 96 is attached to the implant 20. In particular, when the insertion instrument 96 is in the disengaged configuration, the first and second collars 120a and 120b can be spaced from each other along the lateral direction A a distance that is less than the width of a portion of the implant coupler 93 that is disposed proximally from the external groove 95. Because the first and second collars 120a and 120b are resiliently supported by the securement shaft 104, and in particular by the first and second securement plates 106 and 108 respectively, the first and second collars 120a and 120b can resiliently move apart along the lateral direction A as they cam over the portion of the implant coupler 93, and can snap toward each other once they have cleared the portion of the implant coupler and travel into the external groove 95.

The first and second collars 120a and 120b can be aligned with each other along the lateral direction A. Further, at least a portion of each of the first and second collars 120a and 120b is aligned with a portion of the drive member 100 along the lateral direction A when the drive member 100 is in the engaged position. The collars 120a-b can be positioned such that the drive member 100 is disposed between the guide rails 110a-b and the collars 120a-b with respect to the longitudinal direction L when the drive member 100 is in the extended position.

As described above, the first and second securement plates 106 and 108 can be resiliently supported by the securement shaft 104. For instance, in one example, the securement shaft 104 can be forked so as to define first and second securement shaft portions 104a and 104b spaced from each other along the lateral direction A, and separated from each other by a slot 122. Thus, the first and second securement shaft portions 104a and 104b are resiliently movable with respect to each other along the lateral direction A. The first securement plate 106 can extend distally from the first securement shaft portion 104a, and the second securement plate 108 can extend distally from the second securement shaft portion 104b. Accordingly, the first and second securement plates 106 and 108 are resiliently movable with respect to each other along the lateral direction A. Thus, it should be appreciated that the first and second guide rails 110a and 110b are resiliently movable with respect to each other along the lateral direction A. Further, the first and second collars 120a and 120b are resiliently movable with respect to each other along the lateral direction A.

When the securement member 102 is in an initial position the first and second securement plates 106 and 108 are spaced from each other a first distance along the lateral direction A. In the initial position, the securement member 102 is in the disengaged configuration whereby the securement member is configured to be attached to, or removed from, the implant 20. The securement member 102 is configured to receive a biasing force that urges the securement plates 106 and 108 toward each other along the lateral direction A, such that the securement plates 106 and 108 are spaced from each other a second distance along the lateral direction A that is less than the first distance. The securement member 102 thus iterates to the engaged position in response to the biasing force, whereby the securement member 102, and thus the insertion instrument 96, is configured to be secured to the implant 20. Accordingly, the biasing force can urge the first and second guide rails 110a and 110b into the respective guide channels 112. Similarly, the biasing force can urge the first and second collars 120a and 120b into the groove 95 of the driven member 92. It is recognized that increased biasing forces increases the securement of the securement member 102 to the implant 20, and thus of the insertion instrument 96 to the implant 20.

With continuing reference to FIGS. 2A-3 and 4C-4E, the insertion instrument 96 can further include a biasing member 124. As will be appreciated from the description below, the securement member 102 is movable with respect to the biasing member 124 between an engaged position and a disengaged position. When the securement member 102 is in the engaged position, the biasing member 124 delivers the biasing force to the securement member 102. The biasing force can cause the securement member 102 to iterate to the engaged configuration. When the securement member 102 is in the disengaged position, the biasing member 124 removes the biasing force from the securement member 102, thereby causing the securement member 102 to be in the relaxed disengaged configuration. The movement of the securement member 102 between the engaged position and the disengaged position can be along the longitudinal direction L.

The securement member 102 can include at least one bearing member that is in mechanical communication with the first and second securement plates 106 and 108. For instance, the at least one bearing member can extend from the first and second securement plates 106 and 108 such that the biasing force can be applied to the bearing member that, in turn, urges the first and second securement plates toward each other, thereby iterating the securement member 102 to the engaged configuration. The at least one bearing member can include first and second bearing members 126a and 126b that are spaced from each other along the lateral direction A. The biasing member 124 is configured to bear against the bearing members 126a and 126b as the securement member 102 travels toward the engaged position, such that the biasing member 124 applies the biasing force to the bearing members 126a and 126b.

The first and second bearing member 126a can extend between the securement shaft 104 and the first securement plate 106, and the second bearing member 126b can extend between the securement shaft 104 and the second securement plate 108. For instance, the first bearing member 126a can extend between the first securement shaft portion 104a and the first securement plate 106. The second bearing member 126b can extend between the second securement shaft portion 104b spaced and the second securement plate 108. The first bearing member 126a can define a first bearing surface 128a that flares away from the second bearing member 126b as it extends toward the first securement plate 106. Similarly, the second bearing member 126b can define a second bearing surface 128b that flares away from the first bearing member 126a as it extends toward the second securement plate 108. Thus, the first and second bearing surfaces 128a and 128b can flare away from each other each other as they extend toward the first and second securement plates 106 and 108, respectively.

As the securement member 102 travels from the disengaged position to the engaged position, the biasing member 124 bears against one or both of the first and second bearing surfaces 128a and 128b, thereby applying a biasing force that urges the bearing surfaces 128a and 128b toward each other along the lateral direction A. As a result, the first and second bearing members 126a and 126b are urged toward each other along the lateral direction A, which in turn urges the first and second securement plates 106 and 108 to move toward each other along the lateral direction A.

In particular, the biasing member 124 can include respective biasing surfaces 130 at its distal end. The biasing surfaces 130 are aligned with the bearing surfaces 128a and 128b along the longitudinal direction L. Thus, as the securement member 102 travels relative to the biasing member 124 toward the engaged position, the biasing surfaces 130 are brought into contact with the respective first and second bearing surfaces 128a and 128b, thereby causing the biasing force to be applied to the securement plates 106 and 108. Further movement of the securement member 102 with respect to the biasing member 124 toward the engaged position causes the biasing surfaces 130 to travel distally along the outwardly tapered bearing surfaces 128*a* and 128*b*. The distal travel of the biasing surfaces 130 along the first and second bearing surfaces 128*a* and 128*b* causes the biasing forces to increase. The biasing force can be sufficient to retain the first and second guide rails 110*a* and 110*b* in the respective first and second guide channels 112 of the implant 20 both when the implant 20 is in the collapsed configuration and when the implant 20 is in the expanded configuration. Further, the biasing force can be sufficient to retain the collars 120*a* and 120*b* in the external groove 95 of the implant coupler 93.

It is appreciated that movement of the securement member 102 in the proximal direction with respect to the biasing member 124 moves the securement member 102 toward the engaged position. Movement of the securement member 102 in the distal direction with respect to the biasing member 124 moves the securement member 102 toward the disengaged position, whereby the biasing surfaces 130 move proximally along the inwardly tapered bearing surfaces 128*a* and 128*b*. Proximal movement of the biasing surfaces 130 with respect to the bearing surfaces 128*a* and 128*b* causes the biasing forces to decrease until the biasing surfaces 130 are removed from the bearing surfaces 128*a* and 128*b*.

The insertion instrument 96 can further include an engagement member 132 having an opening extending therethrough along the longitudinal direction L that is configured to receive the driver 97. Further, the engagement member 132 is configured to be received in an opening that extends through the biasing member 124 along the longitudinal direction L. The engagement member 132 is configured to engage the securement member 102 so as to cause the securement member 102 to travel with respect to the biasing member 124. In particular, the engagement member 132 can include threads 134, and the securement member 102 can similarly include threads 136 that threadedly mate with the threads 134 of the engagement member 132. The threads 136 can be divided into proximal and distal threaded segments that are spaced from each other by a gap. The gap can have a length along the longitudinal direction L that is greater than the length of the threads 134 along the longitudinal direction. Thus, as will be described in more detail below, the threads 134 can become captured in the gap, such that relative rotation between then engagement member 132 and the securement member 102 will not cause relative translation until the threads 134 and 136 are engaged. The securement member 102 can extend into the engagement member. Thus, the threads 134 of the engagement member 132 can be internal threads, and the threads 136 of the securement member 102 can be external threads that are defined by the securement shaft 104. Accordingly, rotation of the engagement member 132 in a first direction of rotation with respect to the securement member 102 causes the securement member 102 to translate proximally with respect to the biasing member 124 toward the engaged position. Rotation of the engagement member 132 in a second direction of rotation opposite the first direction of rotation causes the securement member 102 to translate distally with respect to the biasing member 124 toward the disengaged position. The engagement member 132 and the biasing member 124 can be translatably fixed to each other with respect to relative translation along the longitudinal direction L. Accordingly, translation of the securement member 102 with respect to the engagement member 132 is also with respect to the biasing member 124. The engagement member 132 can include a knob 138 at its proximal end that can be grasped by a user to facilitate rotation of the engagement member 132. The insertion instrument 96 can further include a handle 131 that is fixedly attached to the biasing member 124 with respect to relative translation along the longitudinal direction. In one example, the handle 131 can be rigidly fixed to the biasing member 124. For instance, the handle 131 can be attached to the biasing member 124 or can be monolithic with the biasing member 124. Thus, as the user grasps and holds the handle 131, the biasing member 124 can remain stationary while the securement member 102 translates relative to the biasing member 124.

The securement member 102 can be prevented from rotating as the engagement member 132 is rotated. In particular, the securement shaft 104 can define an outer surface that is non-circular, and the biasing member 124 can define an inner surface that is non-circular and contacts the non-circular outer surface of the securement shaft 104. The non-circular surfaces can engage so as to prevent relative rotation between the securement shaft 104 and the biasing member 124. Thus, the securement member 102 is rotatably fixed to the biasing member 124. Accordingly, rotation of the engagement member 132 does not cause the securement member 102 to correspondingly rotate with respect to the biasing member 124. As a result, the first and second securement plates 106 and 108 can remain spaced from each other along the lateral direction A.

The insertion instrument 96 can be arranged such that the engagement member 132 extends into the biasing member 124, and the securement member 102 extends into both the biasing member 124 and the engagement member 132. For instance, the proximal end of the securement member 102 can extend into the distal end of the engagement member 132. The drive shaft 98 can extend through the engagement member 132 and the securement member 102, such that the drive member 100 can extend to a location between and aligned with the first and second securement plates 106 and 108 with respect to the lateral direction A. The drive shaft 98 can translate proximally and distally with respect to each of the engagement member 132 and the securement member 102.

Operation of the intervertebral implant system 94 will now be described with reference to FIGS. 5A-11. In particular, referring initially to FIGS. 5A-5B, the insertion instrument 96 can be aligned with the implant 20 along the longitudinal direction L while the securement member 102 is in the disengaged configuration. The implant 20 is in the collapsed configuration. When the insertion instrument 96 is aligned with the implant 20 along the longitudinal direction L, the first guide rail 110*a* can be substantially aligned with the first pair of side walls 64 and 76 along the longitudinal direction L, and the second guide rail 110*b* can be substantially aligned with the second pair 65 of side walls 66 and 78 along the longitudinal direction L. For instance, the first securement plate 106, and thus the first guide rail 110*a*, can be substantially aligned with the lead-in recess 114 at the first side 77 of the implant 20 along the longitudinal direction L. The second securement plate 108, and thus the second guide rail 110*b*, can be substantially aligned with the lead-in recess 114 at the second side 79 of the implant 20 along the longitudinal direction L. Further, the first and second collars 120*a* and 120*b* can be aligned with opposite sides of the implant coupler 93 of the implant 20 along the longitudinal direction L.

Referring now to FIGS. 6A-6B, the insertion instrument 96 can be advanced distally with respect to the implant 20 so as to removably attach the insertion instrument 96 to the implant 20. This advancement of the insertion instrument 96 relative to the implant 20 can be achieved by moving the insertion instrument 96 distally, or by moving the implant 20 proximally, or both. As the insertion instrument 96 is advanced distally relative to the implant 20, the first and second guide rails 110a and 110b ride along the first and second sides 77 and 79 of the implant 20, respectively, in the respective lead-in recesses 114. The distance between the first and second guide rails 110a and 110b along the lateral direction A when the securement member 102 is in the disengaged configuration can be less than the width of the implant 20 at the lead-in recesses 114. Thus, the first and second securement plates 106 and 108 can flex outward away from each other as the first and second guide rails 110a and 110b ride distally along the first and second sides 77 and 79 of the implant 20 in the lead-in recesses 114. The insertion instrument 96 is advanced distally 96 until the first and second guide rails 110a and 110b are inserted into the respective guide channels 112 of the first and second sides 77 and 79 of the implant 20. When the first and second guide rails 110a and 110b are inserted into the respective guide channels 112, the first and second securement plates 106 and 108 can nest in the respective lead-in recesses 114.

Similarly, the distance between the first and second collars 120a and 120b along the lateral direction A when the securement member 102 is in the disengaged configuration can be less than the width of the implant coupler 93. The implant coupler 93 can have a circular cross-section such that the width is a diameter, though the implant coupler 93 can have any suitable size and shape. Thus, as the first and second securement plates 106 and 108 flex outward away from each other, the first and second collars 120a and 120b ride distally along opposed sides of the implant coupler 93 until the first and second guide couplers 120a and 120b are inserted into the external groove 95. With the guide rails 110a and 110b received in the guide channels 112 and with the collars 120a and 120b received in the groove 95, the insertion instrument 96 can be said to be attached to the implant 20. It should be appreciated that when the insertion instrument 96 is attached to the implant 20, the spring constant defined by the resiliently deflected first and second securement plates 106 and 108 provides an attachment force that maintains the attachment of the insertion instrument to the implant 20. The insertion instrument 96 can be removed from the implant 20 by moving the insertion instrument 96 proximally with respect to the implant 20 so as to overcome the attachment force.

Figure 7A:
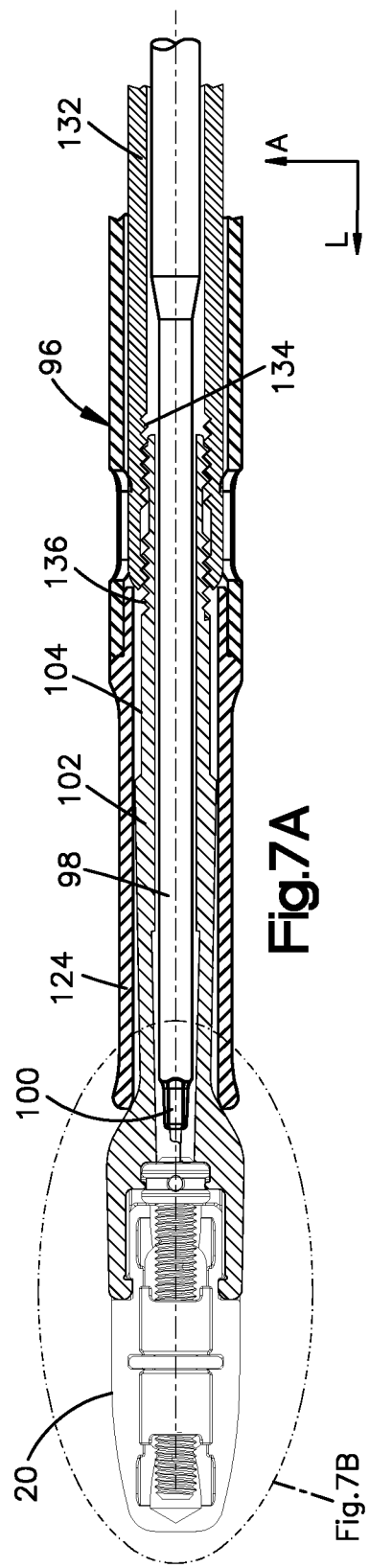
FIG. 7A is a sectional plan view similar to FIG. 6A, but showing the insertion instrument secured to the expandable implant.
Figure 7B:
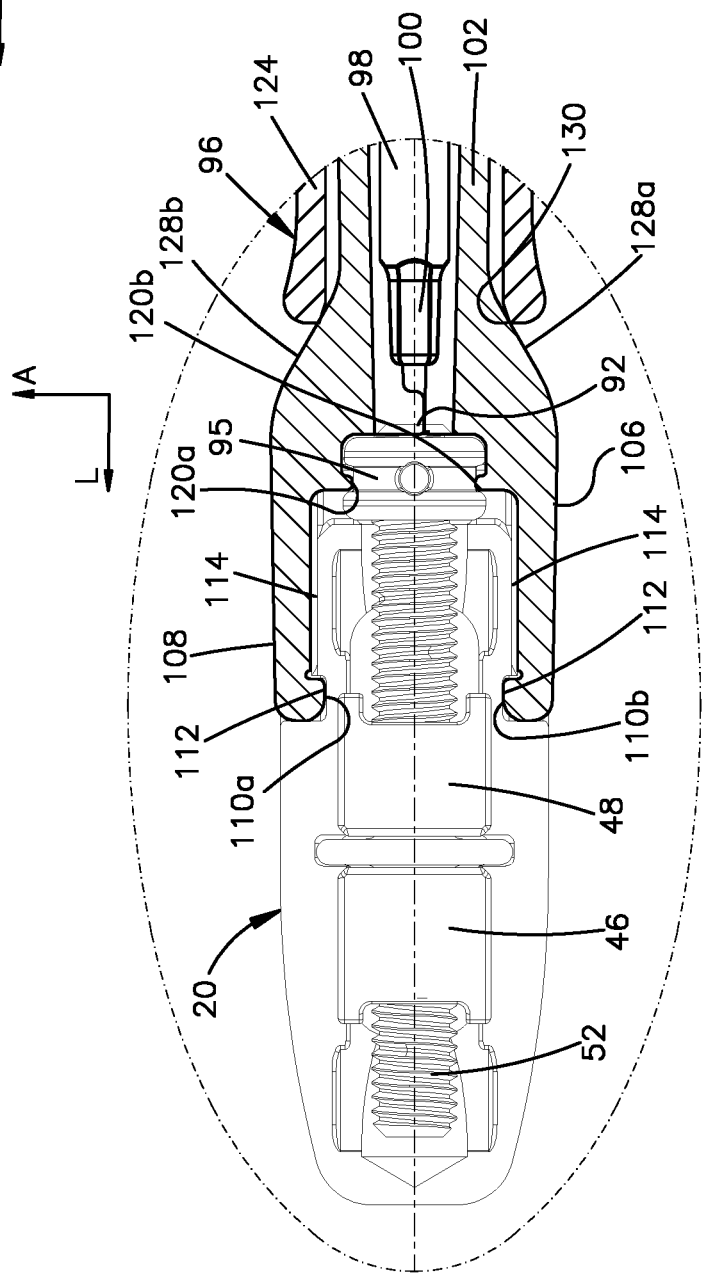
FIG. 7B is an enlarged sectional plan view of a portion of the insertion instrument and the expandable implant of FIG. 7A, taken at Region 7B.

Referring now to FIGS. 7A-7B, the insertion instrument 96 can be secured to the implant 20 to define a rigid construct with the implant 20. In particular, the engagement member 132 can be rotated in the first direction of rotation with respect to the securement member 102, thereby causing the securement member 102 to translate with respect to the biasing member 124 toward the engaged position. The securement member 102 translates proximally until the biasing member 124 applies the biasing force to the securement member 102 in the manner described above. In particular, the biasing member 124 can apply the biasing force to the first and second bearing members 126a and 126b. The biasing force increases as the securement member 102 translates in the proximal direction while the biasing member 124 is in contact with the bearing members 126a and 126b. As the biasing force increases, the securement plates 106 and 108, including the alignment rails 110a-b, are urged against the implant 20 with increasing force, thereby increasing the rigidity of the construct defined by the insertion instrument 96 and the implant 20. The collars 120a-b can be seated in the groove without contacting the outer surface of the implant coupler 93. Thus, the collars 120a-b can be captured by the implant coupler 93 with respect to the longitudinal direction L so as to attach the collars 120a-b to the implant coupler 93. It should be appreciated that the collars 120a-b can remain attached to the implant coupler 93 both when the implant 20 is in the collapsed configuration and when the implant 20 is in the expanded configuration.

Referring now to FIGS. 8A-8B, the drive shaft 98 can be advanced distally until the drive member 100 is rotatably coupled to the driven member 92. For instance, the drive member 100 can be inserted into the driven member 92. Alternatively, the drive member 100 can be received by the driven member 92. It should be appreciated that the step of rotatably coupling the drive shaft 98 to the driven member 92 can be performed before, after, or during securement of the insertion instrument 96 to the implant 20. Further, the step of rotatably coupling the drive shaft 98 to the driven member 92 can be performed before or after the insertion instrument 96 is attached to the implant 20. When the drive member 100 is coupled to the driven member 92, it is recognized that the insertion instrument 96 is attached and secured to the implant 20 at three different attachment and securement locations. A first attachment and securement location is defined by the insertion of the guide rails 110a-b in to the guide slots 112, a second attachment and securement location is defined by the insertion of the collars 120a-b into the groove 95, and a third attachment and securement location is defined by the attachment of the drive member 100 to the driven member 92. When the insertion instrument 96 is secured to the implant 20, the insertion instrument 96 can deliver the implant 20 into the intervertebral space 22 (see FIG. 1).

Referring now to FIGS. 9A-9C, when the insertion instrument 96 is secured to the implant 20 and the drive member 100 is coupled to the driven member 92, the drive member 100 can be rotated in the first direction of rotation so as to cause the implant 20 to expand from the collapsed configuration to the expanded configuration as described above. It should be appreciated that the first direction of rotation of the drive member 100 can be the same direction as the first direction of rotation of the engagement member 132. Alternatively, the first direction of rotation of the drive member 100 can be in an opposite direction with respect to the first direction of rotation of the engagement member 132. As the drive member 100 rotates in the first direction of rotation, the first and second wedge members 46 and 48 move in the expansion direction, so as to cause the first and second endplates 32 and 36 to translate away from each other in the manner described above.

When the implant 20 is in the expanded position, the first and second pairs 63 and 65 of side walls can separate from each other so as to define a gap therebetween. The first and second securement plates 106 and 108 can have a height sufficient to span the gap and remain the respective portions of the lead-in recess 114 defined by the respective side walls of each pair of side walls when the implant 20 is in the expanded position. Similarly, the guide rails 110a and 110b can have a height sufficient to span the gap and remain in respective portions of the guide slots 112 defined by the respective side walls of each pair of side walls when the implant 20 is in the expanded position. The guide rails 110a-110b can ride in the guide slots 112 along the transverse direction T as the implant 20 expands to the expanded position. Similarly, the securement plates 106 and 108 can ride in the lead-in recesses 114 along the transverse direction T as the implant 20 expands to the expanded position. In this regard, it is appreciated that increased biasing forces can cause the instrument 20 add increase resistance to the expansion of the implant 20.

If it is desired to move the implant from the expanded configuration toward the collapsed configuration, the drive member 100 can be rotated in the second direction of rotation, thereby causing the wedge members 46 and 48 to move in the collapsing direction as described above.

Figure 11:
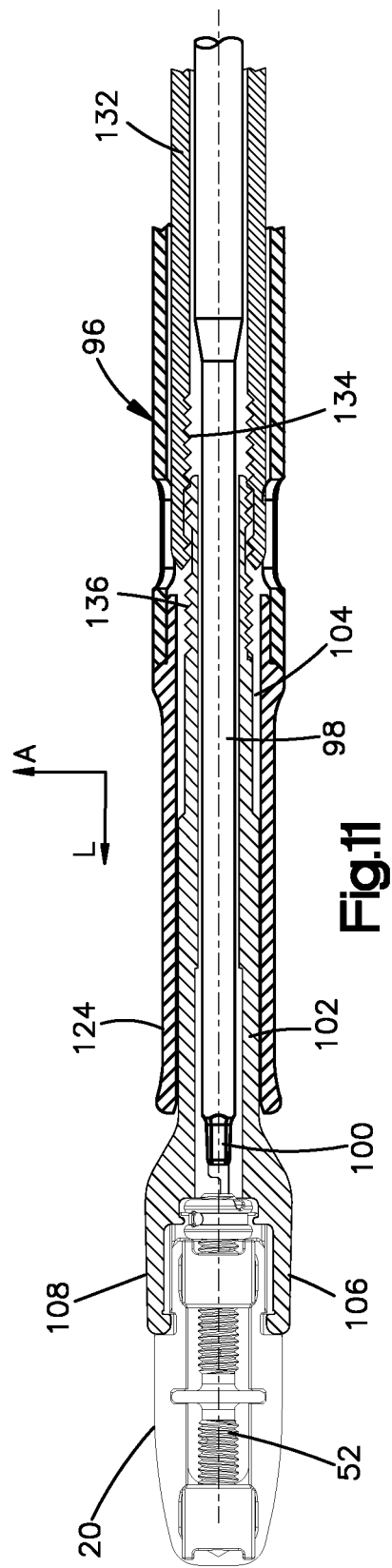
FIG. 11 is a sectional plan view similar to FIG. 10A, but after removal of the securement of the insertion instrument to the expandable implant, such that the insertion instrument is configured to be removed from the expandable implant.

Referring now to FIGS. 10A-11, once the implant 20 has reached a desired height in the intervertebral space, the insertion instrument 96 can be removed from the implant 20. In particular, as illustrated in FIGS. 10A-10B, the securement member 102 can iterate from the engaged configuration to the disengaged configuration. In particular, the engagement member 132 can be rotated in the respective second direction of rotation with respect to the securement member 102, thereby causing the securement member 102 to travel with respect to the biasing member 124 toward the disengaged position. As described above, travel of the securement member 102 in the distal direction can be toward the disengaged position. As the securement member 102 travels with respect to the biasing member 124 to the disengaged position, the biasing member 124 removes the biasing force from the securement member 102. The engagement member 132 can be rotated until the threads 134 of the engagement member 132 are disengaged from the distal threaded segment of the threads 136 of the securement member 102, and captured in the gap that extends between the proximal and distal threaded segments of the threads 136. Accordingly, the engagement member 132 is preventing from rotating a sufficient amount that would inadvertently detach the securement member 102 from the engagement member 132. Rather, once the threads 134 are disposed in the gap, the engagement member 132 can be pulled distally with respect to the securement member so as to engage the threads 134 with the proximal segment of the threads 136. The engagement member 132 can then be rotated with respect to the securement member 102 so as to detach the securement member from the engagement member 132. Alternatively, the entire length of the threads 136 can be continuous and uninterrupted along the longitudinal direction L. Alternatively still, the threads 134 can be divided into proximal and distal segments that are configured to capture the threads 136 therebetween.

Referring to FIG. 11, the drive member 100 can be rotatably decoupled from the driven member 92. Thus, rotation of the drive member 100 does not cause the drive member 92 to rotate. In one example, the drive member 100 can be translated proximally so as to rotatably decouple from the driven member 92. It should be appreciated that the drive member can be rotatably decoupled from the driven member 92 before, after, or during movement of the securement member 102 with respect to the biasing member 124 to the disengaged position. Finally, the insertion instrument 96 can be moved proximally with respect to the implant 20 so as to entirely remove the insertion instrument 96 from the implant 20 as illustrated in FIGS. 5A-5B. In particular, the securement plates 106 and 108 are removed from the lead-in recesses 114.

It should be appreciated that the insertion instrument 96 has been described in accordance with one embodiment whereby the securement member 102 is configured to travel along the longitudinal direction L so as to iterate the securement member 102 between the engaged configuration and the disengaged configuration. Movement of the securement member 102 relative to the biasing member 124 causes the biasing member to apply and release the biasing force.

It should be appreciated in alternative embodiments that the biasing member 124 can alternatively travel along the longitudinal direction L and the securement member 102 can remain stationary. In this alternative embodiment, relative travel exists between the securement member 102 and the biasing member 124. Thus, in this alternative embodiment, it can be said that the securement member 102 travels with respect to the biasing member 124, thereby causing the securement member 102 to iterate between the engaged configuration and the disengaged configuration in the manner described above.

Figure 12:
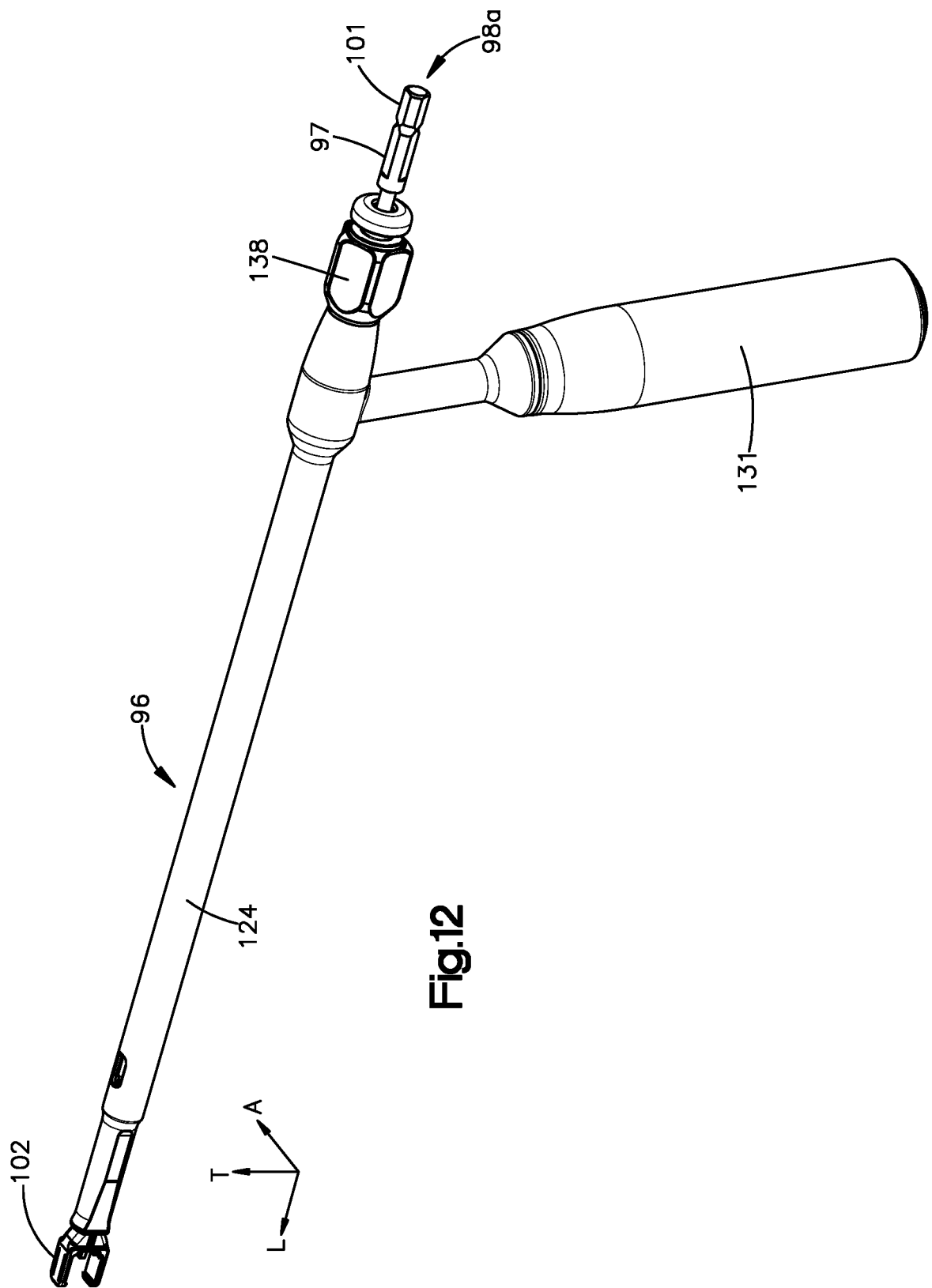
FIG. 12 is a perspective view of the insertion instrument of FIG. 4A without the knob of the drive shaft.

During insertion of the implant 20 into the intervertebral space 22, an impaction force can be applied to a proximal end of the insertion instrument 96 to drive the implant 20 into the intervertebral space. For instance, and with reference to FIGS. 4B and 12, an impaction force can be applied to the proximal end 98a of the drive shaft 98 or to the knob 99. However, applying an impaction force to the proximal end 98a of the drive shaft 98 or knob 99 can result in the force being transmitted down the drive shaft 98 of the insertion instrument 96, through the drive member 100 of the insertion instrument 96, and to the driven member 92 of the implant 20. This can result in damage to one or more of the drive shaft 98, the drive member 100, and the driven member 92. Therefore, the insertion instrument can be configured such that an impaction force applied to the proximal end of the insertion instrument is transmitted down a path that does not include the drive shaft 98. For instance, the impaction force can be transmitted down the engagement member 132 of the insertion instrument, through the securement member 102 of the insertion instrument, and to the implant 20. Thus, the impaction force can be applied to the first and second endplates 32 and 36 of implant 20 as opposed to the driven member 92.

Figure 13:
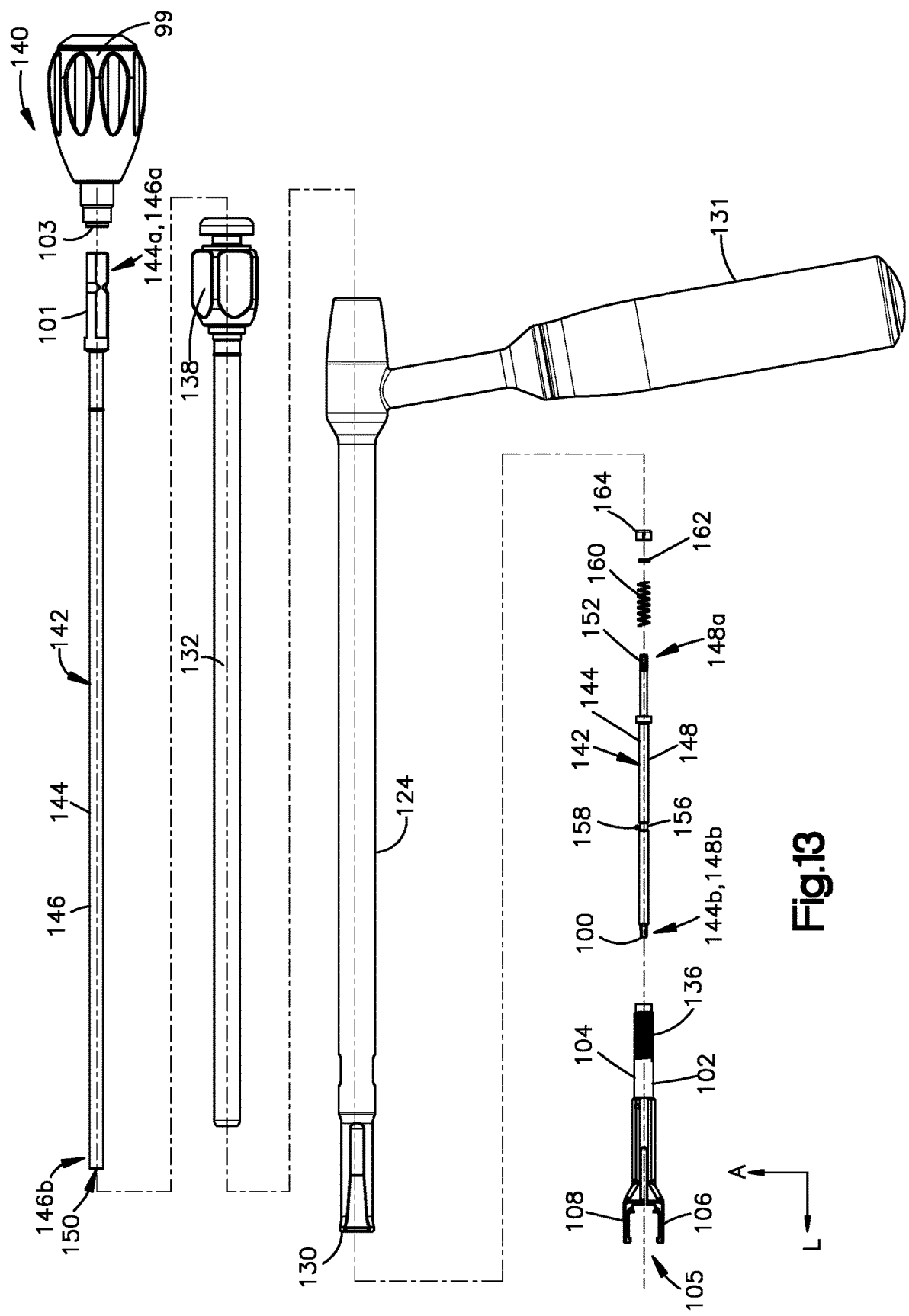
FIG. 13 is an exploded side elevation view of an insertion instrument according to another embodiment.
Figure 14:
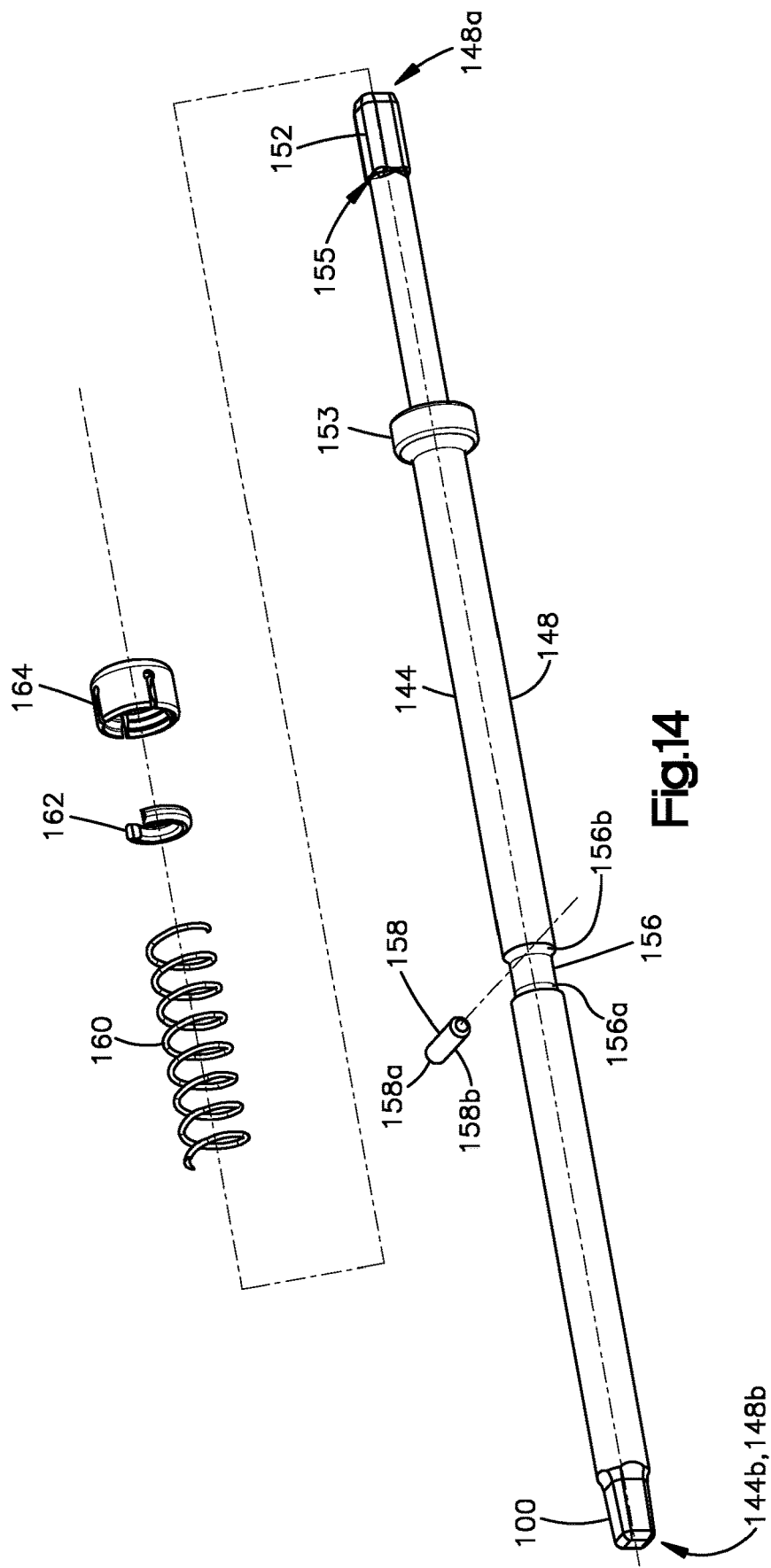
FIG. 14 is an exploded perspective view of a portion of a drive shaft of the insertion instrument of FIG. 13.

As an example, consider the insertion instrument 140 of FIGS. 13 and 14 in which like reference numerals identify similar or identical elements to those discussed above. The insertion instrument 140 is similar to the insertion instrument 96 above, except that the insertion instrument 140 has a driver 142 that is different from the driver 97. The insertion instrument 140 can include a biasing member 124, a handle 131 that is fixedly attached to the biasing member 124, an engagement member 132, and a securement member 102 as described above. The engagement member 132 has an opening extending therethrough along the longitudinal direction L that is configured to receive the driver 142. The driver 142 is configured to absorb an impaction force applied to a proximal end of the driver 142 so as to prevent the impaction force from being transmitted through the driver 142 to the driven member 92 of the implant 20. For example, the impaction force can instead be transmitted through the engagement member 132, through the securement member 102 of the insertion instrument, and to the implant 20.

Figure 15:
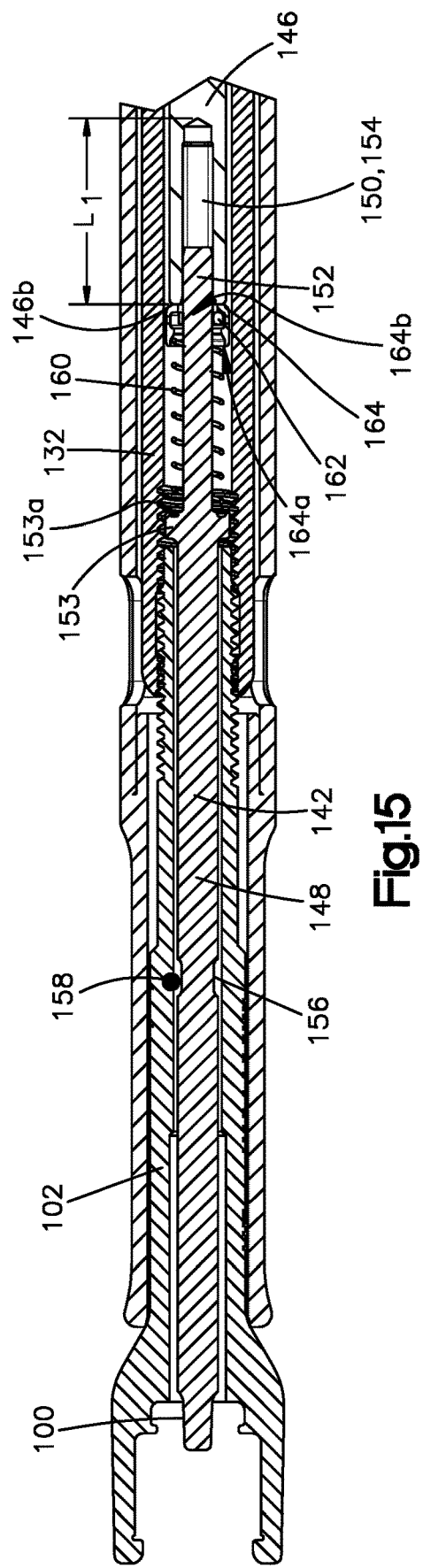
FIG. 15 is a sectional plan view of a distal portion the insertion instrument of FIG. 13.

Now with reference to FIGS. 13-15, the driver 142 has a drive shaft 144 having a first or proximal drive shaft portion 146 and a second or distal drive shaft portion 148 coupled to the first drive shaft portion 146. The first drive shaft portion 146 and the second drive shaft portion 148 can be configured to translate relative to one another. For example, when an impaction force is applied by an impaction instrument to the drive shaft 144, the first drive shaft portion 146 can telescope relative to the second drive shaft portion 148. Thus, the first drive shaft portion 146 can translate distally to thereby retract at least partially into the engagement member 132. Further, the second drive portion 148 can remain stationary relative to the engagement member 132 such that the impaction force is not transferred to the driven member 92 of the implant 20. As a result, the impaction instrument is permitted to impact a proximal end of the engagement member 132 such that substantially all of the impaction force applied by the impaction instrument is applied to the proximal end of the engagement member 132.

The first drive shaft portion 146 has a proximal end 146a and a distal end 146b spaced from one another along the longitudinal direction L. The first drive shaft portion 146 can include an engagement feature 101 at its proximal end 146a. The engagement feature 101 can be configured as described above in relation to FIG. 4C to engage an engagement feature 103 of the knob 99. Further, the engagement feature 101 can include an engagement surface or shoulder 101a that can extend away from a central axis of the drive shaft 144 such that the engagement surface 101a is angularly offset from the central axis. For example, the engagement surface 101a can face in a direction that extends towards the distal end of the drive shaft 144. The first drive shaft portion 146 can further include an engagement feature 150 at its distal end 146b.

The second drive shaft portion 148 has a proximal end 148a and a distal end 148b spaced from one another along the longitudinal direction L. The drive shaft 144 can include a drive member 100 disposed at the distal end 148b of the second drive shaft portion 148. The drive member 100 can be monolithic with the second drive shaft portion 148 or attached to the second drive shaft portion 148. As described above, the drive member 100 is configured to couple to the driven member 92 of the implant 20 (see FIG. 3).

The second drive shaft portion 148 can further include an engagement feature 152 at its proximal end 148a that is configured to engage the engagement feature 150 of the first drive shaft portion 146. In one example, one of the engagement feature 150 of the first drive shaft portion 146 and the engagement feature 152 of the second drive shaft portion 148 can include an outer surface, and the other of the engagement feature 150 and the engagement feature 152 can define a socket 154 (see FIG. 15). The socket 154 can have a length L1 along the longitudinal direction L. For example, as shown in FIG. 15, the engagement feature 152 of the second drive shaft portion 148 can include the outer surface, and the engagement feature 150 of the first drive shaft portion 146 can define the socket 154 (see FIG. 15), where the socket 154 extends into the distal end 146b of the first drive shaft portion 146 by a length L1. It will be understood that, alternatively, the socket 154 can extend into the proximal end 148a of the second drive shaft portion 148.

The first and second drive shaft portions 146 and 148 can be rotationally coupled to one another such that rotation of the first drive shaft portion 146 causes the second drive shaft portion 148 to correspondingly rotate. For example, the engagement feature 150 of the first drive shaft portion 146 can have a non-circular cross section in a plane perpendicular to the longitudinal direction L. Similarly, the engagement feature 152 of the second drive shaft portion 148 can have a non-circular cross section in a plane perpendicular to the longitudinal direction L. The non-circular cross section of the engagement feature 150 can be configured to engage the non-circular cross section of the engagement feature 152 such that rotation of the first drive shaft portion 146 causes the second drive shaft portion 148 to correspondingly rotate.

The second drive shaft portion 148 can be configured to be coupled to the securement member 102 such that the second drive shaft portion 148 is translatably fixed with respect to the securement member 102 along the longitudinal direction L. Thus, when the second drive shaft portion 148 is coupled to the securement member 102, the second drive shaft portion 148 and the securement member 102 are prevented from translating relative to one another along the longitudinal direction. Further, the second drive shaft portion 148 can be configured to be coupled to the securement member 102 such that the second drive shaft portion 148 is rotatable relative to the securement member 102 about a central longitudinal axis of the second drive shaft portion 148. Thus, the second drive shaft portion 148 can rotate while the securement member 102 remains stationary.

In one example, the second drive shaft portion 148 can define a groove 156 that extends into an outer surface of the second drive shaft portion 148. The groove 156 can be annular in shape. Further, the insertion instrument 140 can include a pin 158 that is configured to be coupled to both the securement member 102 and the second drive shaft portion 148. For example, a first portion 158a of the pin 158 can be received in an opening 107 (see FIG. 4D) in the securement member 102, while a second portion 158b of the pin 158, spaced from the first portion 158a, can be received in the groove 156. The pin 158 can be received in the groove 156 such that a central axis of the pin 158 that extends from the first portion 158a to the second portion 158b is perpendicular to a central longitudinal axis of the second drive shaft portion 148.

The second drive shaft portion 148 can include a first shoulder 156a and a second shoulder 156b, offset from the first shoulder 156a along the longitudinal direction L. The first and second shoulders 156a and 156b can at least partially define the groove 156. The first shoulder 156a can face towards the proximal direction. The First shoulder 156a can be substantially annular in shape. The first shoulder 156a can act as a stop that contacts the pin 158 so as to prevent the second drive shaft portion 148 from moving in the proximal direction relative to the securement member 102. The second shoulder 156b can face towards the distal direction. The second shoulder 156b can be substantially annular in shape. The second shoulder 156b can act as a stop that contacts the pin 158 so as to prevent the second drive shaft portion 148 from moving in the distal direction relative to the securement member 102.

Turning briefly to FIGS. 16 and 17, the driver 142 has an extended configuration, wherein the proximal end 144a of the drive shaft 144 extends out of a proximal end 132a of the engagement member 132 in the proximal direction. For example, the drive shaft 144 can extend out of the proximal end 132a by a second length L2. Further, the driver 142 has a retracted configuration, wherein the proximal end 144a of the drive shaft 144 extends out of the proximal end 132a by a third length L3, which is less than the second length L2. The third length L3 can be greater than zero as shown in FIG. 17. Thus, the proximal end 144a can be partially retracted into the proximal end 132a. For example, in FIG. 17, one or both of (i) the surface 101a of the engagement feature 101 and (ii) the distal end 99a of the knob 99 can contact the proximal end 132a of the engagement member 132 so as to limit further translational movement of the first drive shaft portion 146 into the engagement member 132.

Correspondingly, and with reference to FIG. 15, the first drive shaft portion 146 can translate relative to the second drive shaft portion 148 by at least the difference between the second length L2 and the third length L3. The first length L1 of the socket 154 can be greater than or equal to the difference L2−L3 so as to allow the first and second drive shaft portions 146 and 148 to translate relative to one another by the difference L2-L3. Stated differently, the first drive shaft portion 146 can translate relative to the second drive shaft portion 148 by a distance that is less than or equal to the first length L1.

In another example, and with Reference to FIG. 19, the third length L3 can be less than or equal to zero. Thus, when the knob 99 is removed, the proximal end 144a can be retracted so as to be flush with, or extend within, the proximal end 132a of the engagement member 132. Stated differently, the first drive shaft portion 146 can translate into the proximal end 132a of the engagement member 132 by at least the second length L2. Correspondingly, and with reference to FIG. 15, the first drive shaft portion 146 can translate relative to the second drive shaft portion 148 by at least the second length L2. For example, the first length L1 of the socket 154 can be greater than or equal to the second length L2 so as to allow the first and second drive shaft portions 146 and 148 to translate relative to one another by the second length L2.

In operation, an impaction force is applied by an impaction instrument 200 to the proximal end 144a of the drive shaft 144 or to the knob 99. The impaction force causes the drive shaft 144 to move from the extended configuration (e.g., FIG. 16 or FIG. 18) to the retracted configuration (e.g., FIG. 17 or 19) until the impaction force is applied to a proximal end 132a of the engagement member 132 by one or more of (i) the engagement member 101, (ii) the knob 99, and (iii) the impaction instrument. The impaction force is then transmitted down the engagement member 132, through the securement member 102 of the insertion instrument, and to the first and second endplates 32 and 36 of the implant 20.

Referring back to FIGS. 13-15, the driver 142 can further include features that return the drive shaft 144 to the extended configuration after an impaction force is removed and that retain the drive shaft 144 in the extended configuration when an impaction force is not applied. For example, the driver 142 can include a biasing member 160 such as (without limitation) a spring that returns the drive shaft 144 to the extended configuration. To support the biasing member 160, the driver 142 can include a first stop 153 and a second stop 155. In general, the first and second stops 153 and 155 can be supported by one of the first and second drive shaft portions 146 and 148 such that the first and second stops 153 and 155 are spaced from one another along the longitudinal direction L. In FIGS. 13-15, the first and second stops 153 and 155 are supported by the second drive shaft portion 148 and the socket 154 extends into the first drive shaft portion 146. However, it will be understood that the first and second stops 153 and 155 could alternatively be supported by the first drive shaft portion 146 and the socket 154 could extend into the second drive shaft portion 148.

The biasing member 160 can be supported by the drive shaft 144 between the first and second stops 153 and 155. A first end of the biasing member 160 can abut the first stop 153, and the second end of the biasing member 160 can be translatable between the first stop 153 and the second stop 155. The biasing member 160 is configured to apply an outward biasing force to the first and second stops 153 and 155. The outward biasing force causes the second stop 155 to bias the first drive shaft portion 146 in the proximal direction away from the second drive shaft portion 148, while the second drive shaft portion 148 is translatably fixed to the securement member 102 by pin 158.

The first stop 153 can be a collar that is fixed relative to one of the first and second drive shaft portions 146 and 148. The collar can have a cross-sectional dimension that is greater than a cross-sectional dimension of the second drive shaft portion 148. The first stop 153 can have a stop surface 153a that faces in a direction towards the second stop 155. The stop surface 153a can be configured to abut a first end of the biasing member 160. The second stop 155 can be defined by a surface of one of the engagement members 150 and 152.

The driver can include a securement member 164 that is configured to secure one end of the biasing member 160. The securement member can be translatable along the one of the first and second drive shaft portions 146 and 148 so as to allow the biasing member 160 to expand and compress along the longitudinal direction L. In one embodiment, the securement member 164 can be a cap. The securement member 164 can define a recess 164a that extends into the securement member 164 in a direction opposite the first stop 153. The recess 164a can be configured to receive a second end of the biasing member 160. The securement member 164 can further include an opening 164b that extends through the securement member 164 along the longitudinal direction L. The opening 164b can be configured to receive the engagement member 152. Thus, the opening 164b can have a cross-sectional dimension that is greater than a cross-sectional dimension of the engagement member 152 so as to allow the securement member 164 to be received by the engagement member 152. The securement member 164 can further be translatable along the shaft portion between the first stop 153 and the second stop 155.

The driver 142 can further include a clip 162 configured to secure the securement member 164 to the engagement member 152. The clip 162 can define an opening 162a therethrough that has a cross-sectional dimension that is less than a cross-sectional dimension of the second stop 155. The second stop 155 can also have a cross-sectional dimension that is greater than a cross-sectional dimension of the second drive shaft portion 148 between the first and second stops 153 and 155. The clip 162 can further define a slot 162b that is open to the opening 162a. The slot 162a can permit the clip 162 to expand and contact so as to be positionable over the second drive shaft portion 148 between the first and second stops 153 and 155. The slot 162a can further permit the clip 162 to expand and contact so as to be positionable in a groove in the securement member 164. When the clip 162 is received over the second drive shaft portion 148 and in the securement member 164, the clip 162 traps the securement member 164 between the first and second stops 153 and 155 so as to prevent the securement member 164 from translating off of the second drive shaft portion 148 along the proximal direction.

Referring specifically to FIG. 15, in operation, the biasing member 160 applies an outward biasing force to the securement member 164. The outward biasing force causes the securement member 164 to translate along the longitudinal direction L until the securement member 164 abuts the second stop 155. Further, the securement member 164 in turn applies a biasing force to the distal end 146b of the first drive shaft portion 146 so as to bias the first drive shaft portion 146 in the proximal direction away from the second drive shaft portion 148, while the second drive shaft portion 148 is translatably fixed by pin 158. In alternative embodiments, the features can be reversed such that the socket 154 extends into the second drive shaft portion 148, the first and second stops are supported by the first drive shaft portion 146, and the securement member 164 applies a biasing force to the proximal end 148a of the second drive shaft portion 148.

Although the disclosure has been described in detail, it should be understood that various changes, substitutions, and alterations can be made herein without departing from the spirit and scope of the invention as defined by the appended claims. Moreover, the scope of the present disclosure is not intended to be limited to the particular embodiments described in the specification. As one of ordinary skill in the art will readily appreciate from that processes, machines, manufacture, composition of matter, means, methods, or steps, presently existing or later to be developed that perform substantially the same function or achieve substantially the same result as the corresponding embodiments described herein may be utilized according to the present disclosure.

What is claimed:

1. An insertion instrument configured to implant an expandable intervertebral implant in an intervertebral space, the insertion instrument comprising:
    a biasing member;
    a drive shaft elongate along a longitudinal direction;
    a drive member disposed at a distal end of the drive shaft and configured to: 1) couple to a complementary driven member of the implant, and 2) iterate the intervertebral implant from a collapsed configuration to an expanded configuration;
    a securement member arranged relative to the drive shaft such that the securement member is spaced from the drive member along a lateral direction that is perpendicular to the longitudinal direction and such that the drive member is rotatable relative to the securement member to iterate the intervertebral implant from the collapsed configuration to the expanded configuration, the securement member having:
        at least one guide rail that has a height along a transverse direction sufficient to 1) reside in a corresponding at least one guide channel of both an inferior endplate and a superior endplate of the implant when the implant is in the collapsed configuration, 2) ride along the implant in the at least one guide channel as the implant expands to the expanded configuration, and 3) remain in the corresponding at least one guide channel of both the inferior endplate and the superior endplate when the implant is in the expanded configuration; and
        a collar that is configured to be inserted in a corresponding groove of a coupler of the implant that is supported by the driven member while the drive member is engaged with the driven member; and
    an engagement member that is received in the biasing member and threadedly mated with the securement member such that relative rotation between the engagement member and the biasing member in a first direction causes the securement member to travel along the biasing member toward an engaged position in which the securement member is configured to secure to the implant, and relative rotation between the engagement member and the biasing member in a second direction opposite the first direction causes the securement member to travel along the biasing member toward a disengaged position in which the securement member is configured to receive the implant,
    wherein the transverse direction is perpendicular to each of the longitudinal direction and the lateral direction; and
    wherein the securement member defines a recess proximal to the collar such that the collar is between the recess and the at least one guide rail with respect to the longitudinal direction, the recess being configured to receive a portion of the coupler of the implant.

2. The insertion instrument of claim 1, wherein at least a portion of the collar is aligned with a portion of the drive member along the lateral direction.

3. The insertion instrument of claim 2, wherein the drive member is configured to be disposed between the at least one guide rail and the collar with respect to the longitudinal direction.

4. The insertion instrument of claim 1, wherein the securement member comprises first and second securement plates, and the at least one guide rail comprises a first guide rail that projects from the first securement plate toward the second securement plate, and a second guide rail the projects from the second securement plate toward the first securement plate.

5. The insertion instrument of claim 4, wherein the drive member extends between the first and second securement plates along the lateral direction.

6. The insertion instrument of claim 4, wherein the first and second securement plates have respective heights along the transverse direction, and the first and second guide rails extend along respective entireties of the heights of the first and second securement plates, respectively.

7. The insertion instrument of claim 4, wherein, in the engaged position, the biasing member applies a biasing force to the first and second securement plates that urge the first and second securement plates toward each other along the lateral direction, and in the disengaged position, the biasing force is removed from the first and second securement plates.

8. The insertion instrument of claim 7, wherein the biasing force is sufficient to retain the first and second guide rails in respective first and second guide channels of the implant both when the implant is in the collapsed configuration and when the implant is in the expanded configuration.

9. The insertion instrument of claim 8, wherein the securement member comprises opposed first and second bearing members that are spaced from each other along the lateral direction and extend from the first and second securement plates, respectively, and the biasing member is configured to bear against the bearing members as it travels toward the engaged position, such that the biasing force is applied to the bearing members.

10. The insertion instrument of claim 9, wherein the first and second bearing members define respective first and second bearing surfaces that flare away from each other as they extend toward the first and second securement plates, respectively, and the biasing member is configured to bear against the bearing surfaces as it travels toward the engaged position, such that the biasing force is applied to the bearing surfaces.

11. The insertion instrument of claim 1, wherein the drive shaft extends into both the engagement member and the securement member.

12. The insertion instrument of claim 11, wherein the engagement member extends into the biasing member.

13. The insertion instrument of claim 8, wherein the securement member comprises a securement shaft, such that the first and second securement plates extend from the securement shaft, wherein the first and second securement plates are resiliently forked so as to be naturally spaced apart a first distance when the biasing member is in the disengaged position, and the first and second securement plates are spaced apart a second distance less than the first distance when the biasing member is in the engaged position.

14. The insertion instrument of claim 8, wherein the securement member further comprises at least one collar that extends from at least one of the first and second securement plates toward the other of the first and second securement plates, wherein the collar is configured to seat in a groove of the driven member.

15. The insertion instrument of claim 14, wherein the collar includes a first collar that extends from the first securement plate toward the second securement plate, and a second collar that extends from the second securement plate toward the first securement plate.

16. The insertion instrument of claim 15, wherein the biasing force is further configured to urge the first and second collars into the groove of the driven member.

17. The insertion instrument of claim 1, wherein:
the drive shaft has a proximal end, and the distal end offset from the proximal end of the drive shaft along a distal direction that is oriented along the longitudinal direction; and
the drive shaft is configured such that, when an impaction force is applied by an impaction instrument to the proximal end of the drive shaft, the impaction force causes the drive shaft to move in the distal direction from an extended configuration, wherein the proximal end of the drive shaft extends out of the engagement member in a proximal direction that is oriented along the longitudinal direction, opposite the distal direction, to a retracted configuration, wherein the proximal end of the drive shaft is at least partially retracted into the engagement member, so that the impaction force is applied to the engagement member.

18. An intervertebral implant system comprising:
the insertion instrument of claim 1; and
the intervertebral implant of claim 1.

19. The intervertebral implant system as recited in claim 18,
wherein the securement member comprises first and second securement plates, and the at least one guide rail comprises a first guide rail that projects from the first securement plate toward the second securement plate, and a second guide rail the projects from the second securement plate toward the first securement plate, and
wherein the securement plates are no wider or taller than the intervertebral implant when the implant is in the collapsed configuration.

20. An insertion instrument configured to implant an expandable intervertebral implant in an intervertebral space, the insertion instrument comprising:
a biasing member,
a securement member configured to couple to both an inferior endplate and a superior endplate of the intervertebral implant;
an engagement member coupled to the securement member such that rotation of the engagement member in a first direction causes the securement member to move along the biasing member towards an engaged position in which the securement member is configured to secure to the implant, and rotation of the engagement member in a second direction causes the securement member to move along the biasing member towards a disengaged position in which the securement member is configured to receive the implant; and
a driver having:
a drive shaft having a proximal drive shaft portion, and a distal drive shaft portion that is offset from the proximal drive portion along distal direction, the distal drive shaft portion being translatably fixed along the distal direction relative to the securement member, and
a drive member disposed at the distal end of the distal drive shaft portion, the drive member arranged relative to the securement member such that the drive member is configured to 1) couple to a complementary driven member of the intervertebral implant when the securement member couples to the intervertebral implant, and 2) rotate relative to the securement member so as to iterate the intervertebral implant from a collapsed configuration to an expanded configuration,
wherein the drive shaft is configured such that, when an impaction force is applied by an impaction instrument to the proximal drive shaft portion, the impaction force causes the proximal drive shaft portion to translate in the distal direction relative to the distal drive shaft portion and the engagement member from an extended configuration, wherein a proximal end of the drive shaft extends out of the engagement member in a proximal direction, opposite the distal direction, to a retracted configuration, wherein the proximal end of the drive shaft is at least partially retracted into the engagement member, so that the impaction force is applied to the engagement member and not to the distal drive shaft portion.

21. The insertion instrument of claim 20, wherein the proximal and distal drive shaft portions are rotatably coupled to one another.

22. The insertion instrument of claim 20, wherein the distal drive shaft portion is configured to couple to the securement member such that the distal drive shaft portion rotates relative to the securement member and is translatably fixed relative to the securement member with respect to the proximal and distal directions.

23. The insertion instrument of claim 20, wherein the driver includes a biasing element that biases the proximal drive shaft portion to the extended configuration.

* * * * *